US009321701B2

(12) United States Patent
Burk et al.

(10) Patent No.: US 9,321,701 B2
(45) Date of Patent: Apr. 26, 2016

(54) MICROORGANISMS AND METHODS FOR THE BIOSYNTHESIS OF BUTADIENE

(75) Inventors: Mark J. Burk, San Diego, CA (US); Anthony P. Burgard, Bellefonte, PA (US); Jun Sun, San Diego, CA (US); Robin E. Osterhout, San Diego, CA (US); Priti Pharkya, San Diego, CA (US)

(73) Assignee: Genomatica, Inc., San Diego, CA (US)

( * ) Notice: Subject to any disclaimer, the term of this patent is extended or adjusted under 35 U.S.C. 154(b) by 0 days.

(21) Appl. No.: 13/365,132

(22) Filed: Feb. 2, 2012

(65) Prior Publication Data

US 2012/0225466 A1  Sep. 6, 2012

Related U.S. Application Data

(60) Provisional application No. 61/438,947, filed on Feb. 2, 2011.

(51) Int. Cl.
*C12P 5/02* (2006.01)
*C12N 1/20* (2006.01)
*C12N 1/00* (2006.01)
*C07H 21/04* (2006.01)
*C07C 1/24* (2006.01)
*C12P 7/04* (2006.01)

(52) U.S. Cl.
CPC ... *C07C 1/24* (2013.01); *C12P 7/04* (2013.01); *C07C 2521/04* (2013.01); *C07C 2521/12* (2013.01); *C07C 2521/16* (2013.01); *C07C 2523/10* (2013.01); *C07C 2523/28* (2013.01); *C07C 2523/31* (2013.01); *C07C 2523/745* (2013.01); *C07C 2527/167* (2013.01); *C07C 2527/173* (2013.01)

(58) Field of Classification Search
CPC .............. C12P 7/04; C12P 7/16; C12P 5/026; C12P 7/00; C12P 2203/00; C12N 15/52; C12N 9/0008; C12N 9/0006; C12N 9/001; C12N 15/70; C12N 15/81; C12N 1/20; C12N 9/1025; C12N 15/63; C07C 1/24; C07C 11/167; C07C 2521/04; C07C 2527/167; C07C 2527/173
See application file for complete search history.

(56) References Cited

U.S. PATENT DOCUMENTS

| | | | |
|---|---|---|---|
| 5,413,922 | A | 5/1995 | Matsuyama et al. |
| 5,849,970 | A | 12/1998 | Fall et al. |
| 7,127,379 | B2 | 10/2006 | Palsson et al. |
| 7,947,483 | B2 | 5/2011 | Burgard et al. |
| 8,580,543 | B2 | 11/2013 | Burk et al. |
| 2002/0012939 | A1 | 1/2002 | Palsson |
| 2002/0168654 | A1 | 11/2002 | Maranas et al. |
| 2003/0059792 | A1 | 3/2003 | Palsson et al. |
| 2003/0224363 | A1 | 12/2003 | Park et al. |
| 2003/0233218 | A1 | 12/2003 | Schilling |
| 2004/0009466 | A1 | 1/2004 | Maranas et al. |
| 2004/0029149 | A1 | 2/2004 | Palsson et al. |
| 2004/0072723 | A1 | 4/2004 | Palsson et al. |
| 2009/0047719 | A1 | 2/2009 | Burgard et al. |
| 2010/0003716 | A1 | 1/2010 | Cervin et al. |
| 2010/0330635 | A1 | 12/2010 | Burgard et al. |
| 2011/0300597 | A1* | 12/2011 | Burk et al. ................... 435/167 |
| 2013/0011891 | A1* | 1/2013 | Burk et al. ................... 435/157 |
| 2014/0155567 | A1 | 6/2014 | Burk et al. |

FOREIGN PATENT DOCUMENTS

| | | |
|---|---|---|
| GB | 525198 | 8/1940 |
| WO | WO 02/055995 | 7/2002 |
| WO | WO 03/106998 | 12/2003 |
| WO | WO 2007/141208 | 12/2007 |
| WO | WO 2008/115840 | 9/2008 |
| WO | WO 2010/006076 | 1/2010 |
| WO | WO 2010/031079 | 3/2010 |
| WO | WO 2011/052718 | 5/2011 |
| WO | 2011140171 | 11/2011 |

OTHER PUBLICATIONS

Egloff et al. Conversion of oxygen derivatives of hydrocarbons into butadiene, Chem. Rev., (1945), 36(1), 63-141.*
Aberhart and Hsu, "Stereospecific hydrogen loss in the conversion of [2H7] isobutyrate to β-hydroxyisobutyrate in Pseudomonas putida. The stereochemistry of β-hydroxyisobutyrate dehydrogenase," *J. Chem. Soc. [Perkin1]* 6:1404-1406 (1979).
Adams, "Exploratory Catalytic Oxidations with Bismuth Molybdate," *J. Catal.* 10:355-361 (1968).
Ajjawi et al., "Thiamin pyrophosphokinase is required for thiamin cofactor activation in Arabidopsis," *Plant Mol. Biol.* 65(1-2):151-162 (2007). (Epub Jul. 5, 2007).
Alber et al., "Malonyl-Coenzyme A reductase in the modified 3-hydroxypropionate cycle for autotrophic carbon fixation in archaeal *Metallosphaera* and *Sulfolobus* spp.," *J. Bacteriol.* 188(24):8551-8559 (2006).
Alber et al., "Study of an alternate glyoxylate cycle for acetate assimilation by Rhodobacter sphaeroides," *Mol. Microbiol.* 61(2):297-309 (2006).
Altincicek et al., "LytB protein catalyzes the terminal step of the 2-C-methyl-D-erythritol-4-phosphate pathway of isoprenoid biosynthesis," *FEBS Lett.* 532(3):437-440 (2002).
Anderson et al., "Isopentenyl diphosphate:dimethylallyl diphosphate isomerase. An improved purification of the enzyme and isolation of the gene from *Saccharomyces cerevisiae*," *J. Biol. Chem.* 264(32):19169-19175 (1989).
Atsumi et al., "Metabolic engineering of *Escherichia coli* for 1-butanol production," *Metab. Eng.* 10(6):305-311 (2008).
Atsumi et al., "Non-fermentative pathways for synthesis of branched-chain higher alcohols as biofuels," *Nature* 451(7174):86-89 (2008).

(Continued)

*Primary Examiner* — Iqbal H Chowdhury
(74) *Attorney, Agent, or Firm* — Jones Day

(57) ABSTRACT

The invention provides non-naturally occurring microbial organisms having a butadiene pathway. The invention additionally provides methods of using such organisms to produce butadiene.

20 Claims, 4 Drawing Sheets

(56) References Cited

OTHER PUBLICATIONS

Basson et al., "*Saccharomyces cerevisiae* contains two functional genes encoding 3-hydroxy-3-methylglutaryl-coenzyme A reductase," *Proc. Natl. Acad. Sci. U. S. A.* 83(15):5563-5567 (1986).
Beatrix et al., "The biotin-dependent sodium ion pump glutaconyl-CoA decarboxylase from *Fusobactevium nucleatum* (subsp. *nucleatum*). Comparison with the glutaconyl-CoA decarboxylases from gram-positive bacteria," *Arch. Microbiol.* 154(4):362-369 (1990).
Berg et al., "A 3-Hydroxypropionate/4-Hydroxybutyrate Autotrophic Carbon Dioxide Assimilation Pathway in Archaea," *Science* 318(5857) 1782-1786 (2007).
Bergquist and Gibbs, "Degenerate oligonucleotide gene shuffling," *Meth. Mol. Biol.* 352:191-204 (2007).
Bergquist et al., "Degenerate oligonucleotide gene shuffling (DOGS) and random drift mutagenesis (RNDM): Two complementary techniques for enzyme evolution," *Biomol. Eng.* 22:63-72 (2005).
Binstock and Schulz, "Fatty acid oxidation complex from *Escherichia coli*," *Methods Enzymol.* 71(Pt C):403-411 (1981).
Blazquez et al., "Identification and analysis of a glutaryl-CoA dehydrogenase-encoding gene and its cognate transcriptional regulator from *Azoarcus* sp. CIB," *Environ. Microbiol.* 10(2):474-482 (2008).
Bochar et al., "3-hydroxy-3-methylglutaryl coenzyme A reductase of *Sulfolobus solfataricus*: DNA sequence, phylogeny, expression in *Escherichia coli* of the hmgA gene, and purification and kinetic characterization of the gene product," *J. Bacteriol.* 179(11):3632-3638 (1997).
Boiangiu et al., "Sodium Ion Pumps and Hydrogen Production in Glutamate Fermenting Anaerobic Bacteria," *J. Mol. Microbiol. Biotechnol.* 10:105-119 (2005).
Bonner and Bloch, "Purification and properties of fatty acyl thioesterase I from *Escherichia coli*," *J. Biol. Chem.* 247(10):3123-3133 (1972).
Botella-Pavia et al., "Regulation of carotenoid biosynthesis in plants: evidence for a key role of hydroxymethylbutenyl diphosphate reductase in controlling the supply of plastidial isoprenoid precursors," *Plant J.* 40(2):188-199 (2004).
Bower et al., "Cloning, sequencing, and characterization of the Bacillus subtilis biotin biosynthetic operon," *J. Bacteriol.* 178(14):4122-4130 (1996).
Boynton et al., "Cloning, sequencing, and expression of clustered genes encoding β-hydroxybutyryl-Coenzyme A (CoA) dehydrogenase, crotonase, and butyryl-CoA dehydrogenase from *Clostridium acetobutylicum* ATCC 824," *J. Bacteriol.* 178(11):3015-3024 (1996).
Bräsen and Schönheit, "Unusual ADP-forming acetyl-Coenzyme A synthetases from the mesophilic halophilic euryarchaeon Haloarcula marismortui and from the hyperthermophilic crenarchaeon Pyrobaculum aerophilum," *Arch. Microbiol.* 182(4):277-287 (2004).
Braune et al., "The sodium ion translocating glutaconyl-CoA decarboxylase from *Acidaminococcus fermentans*: cloning and function on the genes forming a second operon," *Mol. Microbiol.* 31(2):473-487 (1999).
Bravo et al., "Reliable, sensitive, rapid and quantitative enzyme-based assay for gamma-hydroxybutyric acid (GHB)," *J. Forensic Sci.* 49:379-387 (2004).
Breitkruez et al., "A novel γ-hydroxybutyrate dehydrogenase: Identification and expression of an Arabidopsis cDNA and potential role under oxygen deficiency," *J. Biol. Chem.* 278:41552-41556 (2003).
Buck et al., "Primary structure of the succinyl-CoA synthetase of *Escherichia coli*," *Biochemistry* 24(22):6245-6252 (1985).
Buckel et al., "Glutaconate CoA-Transferase from *Acidaminococcus fermentans*," *Eur. J. Biochem.* 118:315-321 (1981).
Buckel, "Sodium ion-translocating decarboxylases," *Biochimica. Biophysica. Acta* 1505:15-27 (2001).
Burgard et al., "Minimal Reaction Sets for *Escherichia coli* Metabolism under Different Growth Requirements and Uptake Environments," *Biotechnol. Prog.* 17:791-797 (2001).
Burgard et al., "Optknock: a bilevel programming framework for identifying gene knockout strategies for microbial strain optimization," *Biotechnol. Bioeng.* 84(6):647-657 (2003).
Buu et al., "Functional characterization and localization of acetyl-CoA hydrolase, Ach1p, in *Saccharomyces cerevisiae*," *J. Biol. Chem.* 278:17203-17209 (2003).
Byres et al., "Crystal structures of *Trypanosoma brucei* and *Staphylococcus aureus* mevalonate diphosphate decarboxylase inform on the determinants of specificity and reactivity," *J. Mol. Biol.* 371(2):540-553 (2007). (Epub Jun. 4, 2007).
Cahyanto et al., "Regulation of aspartokinase, asparate semialdehyde dehydrogenase, dihydrodipicolinate synthease and dihydropdipicolinate reductase in *Lactobacillus plantarum*," *Microbiology* 152 (Pt 1): 105-112 (2006).
Cane et al., "Molecular cloning, expression and characterization of the first three genes in the mevalonate-independent isoprenoid pathway in *Streptomyces coelicolor*," *Bioorg. Med. Chem.* 9(6):1467-1477 (2001).
Cary et al., "Cloning and Expression of *Clostridium acetobutylicum* ATCC 824 Acetoacetyl-Coenzyme A:Acetate/Butyrate:Coenzyme A-Transferase in *Escherichia coli*," *App. Environ. Microbiol.* 56(6):1576-1583 (1990).
Charrier et al., "A novel class of CoA-transferase involved in short-chain fatty acid metabolism in butyrate-producing human colonic bacteria," *Microbiology* 152:179-185 (2006).
Chowdhury et al., "3-Hydroxyisobutyrate dehydrogenase from *Pseudomonas putida* E23: purification and characterization," *Biosci. Biotechnol. Biochem.* 60(12):2043-2047 (1996).
Chowdhury et al., "Cloning and overexpression of the 3-hydroxyisobutyrate dehydrogenase gene from *pseudomonas putida* E23," *Biosci. Biotechnol. Biochem.* 67(2):438-441 (2003).
Coco et al., "DNA shuffling method for generating highly recombined genes and evolved enzymes," *Nat. Biotechnol.* 19:354-359 (2001).
Colby and Chen, "Purification and properties of 3-hydroxybutyryl-Coenzyme A dehydrogenase from *Clostridium beijerinckii* ("*Clostridium butylicum*") NRRL B593," *Appl. Environ. Microbiol.* 58:3297-3302 (1992).
Colonna et al., "Synthesis and radiocarbon evidence of terephthalate polyesters completely prepared from renewable resources," *Green Chemistry* 13:2543-2548 (2011).
Corthesy-Theulaz et al., "Cloning and Characterization of Helicobacter pylori Succinyl CoA:Acetoacetate CoA-transferase, a Novel Prokaryotic Member of the CoA-transferase Family," *J. Biol. Chem.* 272(41):25659-25667 (1997).
Crans et al., "Glycerol Kinase: Substrate Specificity," *J. Am. Chem. Soc.* 107:7008-7018 (2010).
Currie et al., "Authentication and dating of biomass components of industrial materials; links to sustainable technology," *Nucl. Instrum. Methods Phys. Res., Sect. B* 172:281-287 (2000).
de Ruyck et al., "Structural role for Tyr-104 in *Escherichia coli* isopentenyl-diphosphate isomerase: site-directed mutagenesis, enzymology, and protein crystallography," *J. Biol. Chem.* 281(26):17864-17869 (2006). (Epub Apr. 15, 2006).
Deana, "Substrate specificity of a dicarboxyl-CoA: dicarboxylic acid Coenzyme A transferase from rat liver mitochondria," *Biochem. Int.* 26(4):767-773 (1992).
Desai et al., "A metabolic bypass of the triosephosphate isomerase reaction," *Biochemistry* 47(31):7983-7985 (2008). (Epub Jul. 12, 2008).
Di Gennaro, "Styrene lower catabolic pathway in *Pseudomonas fluorescens* ST: identification and characterization of genes for phenylacetic acid degradation," *Arch. Microbiol.* 188(2):117-125 (2007).
Doten et al., "Cloning and Genetic Organization of the pca Gene cluster from *Acinetobacter calcoaceticus*," *J. Bacteriol.* 169(7):3168-3174 (1987).
Doun et al., "Enterococcus faecalis phosphomevalonate kinase," *Protein Sci.* 14(5):1134-1139 (2005). (Epub Mar. 31, 2005).
Drake, "Acetogenesis, acetogenic bacteria, and the acetyl-CoA "Wood/Ljungdahl" pathway: past and current perspectives," in *Acetogenesis*, H. L. Drake, (ed.), Chapman & Hall, New York, p. 3-60 (1994).

(56) References Cited

OTHER PUBLICATIONS

Duncan et al., "Acetate utilization and butyryl Coenzyme A (CoA):acetate-CoA transferase in butyrate-producing bacteria from the human large intestine," *Appl. Environ. Microbiol.* 68(10):5186-5190 (2002).

Dwyer et al., "Proton Abstraction reaction, Steady-State kinetics, and Oxidation-Reduction Potential of Human Glutaryl-CoA Dehydrogenase," *Biochemistry* 39:11488-11499 (2000).

Fernandes et al., "Kinetic characterization of *Synechocystis* sp. PCC6803 1-deoxy-D-xylulose 5-phosphate reductoisomerase mutants," *Biochim. Biophys. Acta* 1764(2):223-229 (2006). (Epub Sep. 23, 2005).

Fernandes et al., "Mutation in the flexible loop of 1-deoxy-D-xylulose 5-phosphate reductoisomerase broadens substrate utilization," *Arch. Biochem. Biophys.* 444(2):159-164 (2005). (Epub Oct. 27, 2005).

Fontaine et al., "Molecular charcterization and transcriptional analysis of adhE2, the gene encoding the NADH-dependent aldehyde/alcohol dehydrogenase responsible for butanol production in alcohologenic cultures of Clostridium acetobutylicum ATCC 824," *J. Bacteriol.* 184:821-830 (2002).

Ford et al., "Molecular properties of the lystl+ gene and the regulation of α-aminoadipate reductase in *Schizosaccharomyces pombe*," *Curr. Genet.* 28:131-137 (1995).

Freidrich et al., "The complete stereochemistry of the enzymatic dehydration of 4-hydroxybutyryl Coenzyme A to crotonyl Coenzyme A," *Angew. Chem. Int. Ed.* 47:3254-3257 (2008).

Fu et al., "Crystal structures of human glutaryl-CoA dehydrogenase with and without an alternate substrate: structural bases of dehydrogenation and decarboxylation reactions," *Biochemistry* 43(30):9674-9684 (2004).

Fujii et al., "Error-prone rolling circle amplification: the simplest random mutagenesis protocol," *Nat. Protoc.* 1:2493-2497 (2006).

Fujii et al., "One-step random mutagenesis by error-prone rolling circle amplification," *Nucleic Acids Res.* 32:e145 (2004).

Gabrielsen et al., "Hexameric assembly of the bifunctional methylerythritol 2,4-cyclodiphosphate synthase and protein-protein associations in the deoxy-xylulose-dependent pathway of isoprenoid precursor biosynthesis," *J. Biol. Chem.* 279(50):52753-52761 (2004). (Epub Oct. 2, 2004).

Gibbs et al., "Degenerate olignucleotide gene shuffling (DOGS): a method for enhancing the frequence of recombination with family shuffling," *Gene* 271:13-20 (2001).

Grawert et al., "IspH protein of *Escherichia coli*: studies on iron-sulfur cluster implementation and catalysis," *J. Am. Chem. Soc.* 126(40):12847-12855 (2004).

Guo and Bhattacharjee, "Posttranslational activation, site-directed mutation and phylogenetic analyses of the lysine biosynthesis enzymes a-aminoadipate reductase Lyslp (AAR) and the phosphopantetheinyl transferase Lys7p (PPTase) from *Schizosaccharomyces pombe*," *Yeast* 21:1279-1288 (2004).

Guo and Bhattacharjee, "Site-directed mutational analysis of the novel catalytic domains of a-aminoadipate reductase (Lys2p) from candida albicans," *Mol. Gen. Gemonics* 269:271-279 (2003).

Hajny et al., "Erythritol Production by a Yeastlike Fungus," *Appl. Microbiol.* 12:240-246 (1964).

Haller et al., "Discovering new enzymes and metabolic pathways: conversion of succinate to propionate by *Escherichia coli*," *Biochem.* 39(16):4622-4629 (2000).

Hanai et al., "Engineered synthetic pathway for isopropanol production in *Escherichia coli*," *Appl. Environ. Microbiol.* 73(24):7814-7818 (2007).

Harrison and Harwood, "The pimFABCDE operon from Rhodopseudomonas palustris mediates dicarboxylic acid degradation and participates in anaerobic benzoate degradation," *Microbiology* 151:727-736 (2005).

Hartel et al., "Purification of glutaryl-CoA dehydrogenase from *Pseudomonas* sp., an enzyme involved in the anaerobic degradation of benzoate," *Arch. Mirobiol.* 159:174-181 (1993).

Harwood et al., "Identification of the pcaRKF Gene cluster from Pseudomonas putida: Involvement in Chemotaxis, Biodegradation, and Transport of 4-Hydroxybenzoate," *J. Bacteriol.* 176(21):6479-6488 (1994).

Hasegawa et al., "Transcriptional regulation of ketone body-utilizing enzyme, acetoacetyl-CoA synthetase, by C/EBPa during adipocyte differentiatiion," *Biochimica. Biophysica. Acta* 1779:414-419 (2008).

Hashimoto et al., "The occurrence of a reductase of delta2-carboxylic acids in Clostridium kluyveri with a stereospecificity different from that of butyryl-CoA dehydrogenase," *Hoppe Seylers Z Physiol. Chem.* 356(8):1203-1208 (1975). (English Abstract Only).

Hawes et al., "Mammalian 3-hydroxyisobutyrate dehydrogenase," *Methods Enzymol.* 324:218-228 (2000).

Hayashi et al., "Purification and properties of glycerol kinase from *Escherichia coli*," *J. Biol. Chem.* 242(5):1030-1035 (1967).

Hayes et al., "Combining computational and experimental screening for rapid optimization of protein properties," *Proc. Natl. Acad. Sci. U.S.A.* 99(25):15926-15931 (2002).

Haywood et al., "Characterization of two 3-ketothiolases possessing differing substrate specificities in the polyhydroxyalkanoate synthesizing organism Alcaligenes eutrophus," *FEMS Microbiol. Lett.* 52:91-96 (1988).

Henriksson et al., "Structures of *Mycobacterium tuberculosis* 1-Deoxy-D-xylulose-5-phosphate Reductoisomerase provide new insights into catalysis," *J. Biol. Chem.* 282(27):19905-19916 (2007). (Epub May 9, 2007).

Henriksson et al., "The 1.9 Å resolution structure of *Mycobacterium tuberculosis* 1-deoxy-D-xylulose 5-phosphate reductoisomerase, a potential drug target," *Acta. Crystallogr. D. Biol. Crystallogr.* 62(Pt 7):807-813 (2006).

Hibbert et al., "Directed evolution of biocatalytic processes," *Biomol. Eng.* 22:11-19 (2005).

Hijarrubia et al., "Domain Structure Characterization of the Multifunctional α-Aminoadipate Reductase from Penicillium chrysogenum by Limited Proteolysis," *J. Biol. Chem.* 278(10):8250-8256 (2003).

Hillmer and Gottschalk, "Particulate Nature of Enzymes Involved in the Fermentation of Ethanol and Acetate by Clostridium Kluyveri," *FEBS Lett.* 21(3):351-354 (1972).

Hillmer and Gottschalk, "Solubilization and partial characterization of particulate dehydrogenases from Clostridium kluyveri," *Biochim. Biophys. Acta.* 334:12-23 (1974).

Hiser et al., "ERG10 from *Saccharomyces cerevisiae* encodes acetoacetyl-CoA thiolase," *J. Biol. Chem.* 269:31383-31389 (1994).

Hoffmeister et al., "Mitochondrial trans-2-enoyl-CoA reductase of wax ester fermentation from Euglena gracilis defines a new family of enzymes involved in lipid synthesis," *J. Biol. Chem.* 280(6):4329-4338 (2005).

Hove-Jenson et al., "Phosphoribosylpyrophosphate synthetase of *Escherichia coli*. Properties of the purified enzyme and primary structure of the prs gene," *J. Biol. Chem.* 261(15):6765-6771 (1986).

Hugler et al., "Malonyl-Coenzyme A Reductase from Chloroflexus aurantiacus, a Key Enzyme of the 3-Hydroxypropionate Cycle for Autotrophic CO2 Fixation," *J. Bacteriol.* 184(9):2404-2410 (2002).

Huisman and Lalonde, "Enzyme evolution for chemical process applications," In R.N. Patel (ed.), *Biocatalysis in the pharmaceutical and biotechnology industries*, CRC Press, p. 717-742 (2007).

Huo and Viola, "Functional group characterization of homoserine kinase from *Escherichia coli*," *Arch. Biochem. Biophys.* 330(2):373-379 (1996).

Huo and Viola, "Substrate Specificity and Identification of Functional Groups of Homoserine Kinase from *Escherichia coli*," *Biochemistry* 35:16180-16185 (1996).

Husain and Steenkamp, "Partial purification and characterization of glutaryl-Coenzyme A dehydrogenase, electron transfer flavoprotein, and electron transfer flavoprotein-Q oxidoreductase from Paracoccus denitrificans," *J. Bacteriol.* 163:709-715 (1985).

Ishige et al., "Wax ester production from n-alkanes by *Acinetobacter* sp. strain M-1: ultrastructure of cellular inclusions and role of acyl Coenzyme A reductase," *Appl. Environ. Microbiol.* 68(3):1192-1195 (2002).

(56) References Cited

OTHER PUBLICATIONS

Ismaiel et al., "Purification and Characterization of a Primary-Secondary Alcohol Dehydrogenase from Two Strains of Clostridium beijerinckii," *J. Bacteriol.* 175(16):5097-5105 (1993).
Ismail et al., "Functional genomics by NMR spectroscopy. Phenylacetate catabolism in *Escherichia coli*," *Eur. J. Biochem.* 270(14):3047-3054 (2003).
Itoh et al., "Continuous production of chiral 1,3-butanediol using immobilized biocatalysts in a packed bed reactor: promising biocatalysis method with an asymmetric hydrogen-transfer bioreduction," *Appl. Microbiol. Biotechnol.* 75(6):1249-1256 (2007). (Epub Apr. 19, 2007).
Jacques et al., "Characterization of yeast homoserine dehydrogenase, an antifungal target: the invariant histidine 309 is important for enzyme integrity," *Biochem. Biophys. Acta* 1544:28-41 (2001).
James and Viola, "Production and characterization of bifunctional enzymes. Domain swapping to produce new bifunctional enzymes in the aspartate pathway," *Biochemistry* 41(11) 3720-3725 (2002).
Jeon et al., "Heterologous expression of the alcohol dehydrogenase (adhI) gene from Geobacillius thermoglucosidasius strain M10EXG," *J. Biotechnol.* 135:127-133 (2008).
Jones and Woods, "Acetone-butanol fermentation revisited," *Microbiol. Rev.* 50(4):484-524 (1986).
Julsing et al., "Functional analysis of genes involved in the biosynthesis of isoprene in Bacillus subtilis," *Appl. Microbiol. Biotechnol.* 75:1377-1384 (2007).
Kajiwara et al., "Expression of an exogenous isopentenyl diphosphate isomerase gene enhances isoprenoid biosynthesis in *Escherichia coli*," *Biochem J.* 324 ( Pt 2):421-426 (1997).
Karlen et al., "Absolute determination of the activity of two $C^{14}$ dating standards," *Arkiv Geofysik* 4:465-471 (1968).
Kaschabek et al., "Degradation of aromatics and chloroaromatics by *Pseudomonas* sp. strain B13: purification and characterization of 3-oxoadipate:succinyl-Coenzyme A (CoA) transferase and 3-oxoadipyl-CoA thiolase," *J. Bacteriol.* 184(1):207-215 (2002).
Kazahaya et al, "Aerobic Dissimilation of Glucose by Heterolactic Bacteria III. Aldehyde dehydrogenase and alcohol dehydrogenase of luconostoc mesenteroides" *J. Gen. Appl. Microbiol.* 18(1):43-55 (1972).
Kemp et al., "Crystallization and preliminary X-ray diffraction studies of recombinant *Escherichia coli* 4-diphosphocytidyl-2-C-methyl-D-erythritol synthetase," *Acta Crystallogr. D Biol. Crystallogr.* 57(Pt 8):1189-1191 (2001). (Epub Jul. 23, 2001).
Kemp et al., "Structure of a tetragonal crystal form of *Escherichia coli* 2-C-methyl-D-erythritol 4-phosphate cytidylyltransferase," *Acta Crystallogr. D Biol. Crystallogr.* 59(Pt 3):607-610 (2003). (Epub Feb. 21, 2003).
Kessler et al., "Pyruvate-formate-lyase-deactivase and acetyl-CoA reductase activities of *Escherichia coli* reside on a polymeric protein particle encoded by adhE," *FEBS Lett.* 281(1-2):59-63 (1991).
Kinoshita, "Purification of two alcohol dehydrogenases from Zymomonas mobilis and their properties," *Appl. Microbiol. Biotechnol.* 22:249-254 (1985).
Kishida et al., "Structure and catalytic mechanism of 2-C-methyl-D-erythritol 2,4-cyclodiphosphate (MECDP) synthase, an enzyme in the non-mevalonate pathway of isoprenoid synthesis," *Acta Crystallogr. D Biol. Crystallogr.* 59(Pt 1):23-31 (2003). (Epub Dec. 19, 2002).
Klatt et al., "Comparative genomics provides evidence for the 3-hydroxypropionate autotrophic pathway in filamentous anoxygenic phototrophic bacteria and in hot spring microbial mats," *Environ. Microbiol.* 9:2067-2078 (2007).
Koh et al., "Scale-up of erythritol production by an osmophilic mutant of Candida magnoliae," *Biotechnol. Lett.* 25(24):2103-2105 (2003).
Kollas et al., "Functional characterization of GcpE, an essential enzyme of the non-mevalonate pathway of isoprenoid biosynthesis," *FEBS Lett.* 532(3):432-436 (2002).

Koo et al., "Cloning and characterization of the bifunctional alcohol/acetaldehyde dehydrogenase gene (adhE) in Leuconostoc mesenteroides isolated from kimchi," *Biotechnol. Lett.* 27(7):505-510 (2005).
Korolev et al., "Autotracing of *Escherichia coli* acetate CoA-transferase a-subunit structure using 3.4 Å MAD and 1.9 Å native data," *Acta. Crystallogr. D. Biol. Crystallogr.* 58(Pt 12):2116-2121 (2002).
Kosaka et al., "Characterization of the sol operon in butanol-hyperproducing Clostridium saccharoperbutylacetonicum strain N1-4 and its degeneration mechanism," *Biosci. Biotechnol. Biochem.* 71:58-68 (2007).
Kosjek et al., "Purification and characterization of a chemotolerant alcohol dehydrogenase applicable to coupled redox reactions," *Biotechnol. Bioeng.* 86(1):55-62 (2004).
Kowalchuk et al., "Contrasting patterns of evolutionary divergence within the Acinetobacter calcoaceticus pca operon," *Gene* 146:23-30 (1994).
Kreimeyer et al., "Identification of the Last Unknown Genes in the Fermentation Pathway of Lysine," *J. Biol. Chem.* 282(10):7191-7197 (2007).
Kretz et al., "Gene Site Saturation Mutagenesis: A Comprehensive Mutagenesis Approach," *Methods Enzymol.* 388:3-11 (2004).
Kuznetsova et al., "Enzyme genomics: Application of general enzymatic screens to discover new enzymes," *FEMS Microbiol. Rev.* 29(2):263-279 (2005).
Lamas-Maceiras et al., "Amplification and disruption of the phenylacetyl-CoA ligase gene of Penicillium chrysogenum encoding an aryl-capping enzyme that supplies phenylacetic acid to the isopenicillin N-acyltransferase," *Biochem. J.* 395(1):147-155 (2006).
Lamed and Zeikus, "Novel NADP-linked alcohol-aldehyde/ketone oxidoreductase in thermophilic ethanologenic bacteria," *Biochem. J.* 195:183-190 (1981).
Laupitz et al., "Biochemical characterization of Bacillus subtilis type II isopentenyl diphosphate isomerase, and phylogenetic distribution of isoprenoid biosynthesis pathways," *Eur. J. Biochem.* 271(13):2658-2669 (2004).
Learned et al., "3-Hydroxy-3-methylglutaryl-coenzyme A reductase from Arabidopsis thaliana is structurally distinct from the yeast and animal enzymes," *Proc. Natl. Acad. Sci. U. S. A.* 86(8):2779-2783 (1989).
Leduc et al., "The hotdog thioesterase EntH (YbdB) plays a role in vivo in optimal enterobactin biosynthesis by interacting with the ArCP domain of EntB," *J. Bacteriol.* 189(19):7112-7126 (2007).
Lee et al., "A new approach to directed gene evolution by recombined extension on truncated templates (RETT)," *J. Molec. Catalysis* 26:119-129 (2003).
Lee et al., "Fumarate-mediated inhibition of erythrose reductase, a key enzyme for erythritol production by Torula corallina," *Appl. Environ. Microbiol.* 68(9):4534-4538 (2002).
Lee et al., "Purification and characterization of a novel erythrose reductase from Candida magnoliae," *Appl. Environ. Microbiol.* 69(7):3710-3718 (2003).
Lee et al., "Purification and properties of a NADPH-dependent erythrose reductase from the newly isolated Torula corallina," *Biotechnol. Prog.* 19(2):495-500 (2003).
Lehmann et al., "Structure of 2C-methyl-D-erythrol-2,4-cyclodiphosphate synthase from Haemophilus influenzae: activation by conformational transition," *Proteins* 49(1):135-138 (2002).
Li et al., "Coupled Ferredoxin and Crotonyl Coenzyme A (CoA) Reduction with NADH Catalyzed by the Butyryl-CoA Dehydrogenase/Etf Complex from Clostridium kluyveri," *J. Bacteriol.* 190(3):843-850. (2008). (Epub Nov. 9, 2007).
Lillo et al., "Functional expression and characterization of EryA, the erythritol kinase of Brucella abortus, and enzymatic synthesis of L-erythritol-4-phosphate," *Bioorg. Med. Chem. Lett.* 13(4):737-739 (2003).
Lin et al., "Fed-batch culture of a metabolically engineered *Escherichia coli* strain designed for high-level succinate production and yield under aerobic conditions," *Biotechnol. Bioeng.* 90:775-779 (2005).

(56) References Cited

OTHER PUBLICATIONS

Lindberg et al., "Engineering a platform for photosynthetic isoprene production in cyanobacteria, using Synechocystis as the model organism," *Metab. Eng.* 12(1):70-79 (2010). (Epub Oct. 13, 2009).
Lokanath et al., "Crystal structure of novel NADP-dependent 3-hydroxyisobutyrate dehydrogenase from Thermus thermophilus HB8," *J. Mol. Biol.* 352(4):905-917 (2005).
Low et al., "Mimicking somatic hypermutation: Affinity maturation of antibodies displayed on bacteriophage using a bacterial mutator strain," *J. Mol. Biol.* 260(3):359-368 (1996).
Lutz et al., "Creating multiple-crossover DNA libraries independent of sequence identity," *Proc. Natl. Acad. Sci. U.S.A.* 98:11248-11253 (2001).
Lutz et al., "Rapid generation of incremental truncation libraries for protein enginering using α-phosphothioate nucleotides," *Nucleic Acids Res.* 29:E16 (2001).
Mac Sweeney et al., "The crystal structure of *E.coli* 1-deoxy-D-xylulose-5-phosphate reductoisomerase in a ternary complex with the antimalarial compound fosmidomycin and NADPH reveals a tight-binding closed enzyme conformation," *J. Mol. Biol.* 345(1):115-127 (2005).
Mack and Buckel, "Conversion of glutaconate CoA-transferase from Acidaminococcus fermentans into an acyl-CoA hydrolase by site-directed mutagenesis," *FEBS Lett.* 405(2):209-212 (1997).
Mack et al., "Location of the two genes encoding glutaconate Coenzyme A-transferase at the beginning of the hydroxyglutarate operon in Acidaminococcus fermentans," *Eur. J. Biochem.* 226:41-51 (1994).
Mann, "An International Reference Material for Radiocarbon Dating," *Radiocarbon* 25(2):519-527 (1983).
Manning and Pollitt, "Tracer studies of the interconversion of R- and S-methylmalonic semialdehydes in man," *Biochem. J.* 231(2):481-484 (1985).
Marks et al., "Molecular cloning and characterization of (R)-3-hydroxybutyrate dehydrogenase from human heart," *J. Biol. Chem.* 267(22):15459-15463 (1992).
Martin et al., "Engineering a mevalonate pathway in *Escherichia coli* for production of terpenoids," *Nat. Biotechnol.* 21:796-802 (2003).
Martínez-Blanco, et al, "Purification and biochemical characterization of phenylacetyl-CoA ligase from Pseudomonas putida. A specific enzyme for the catabolism of phenylacetic acid," *J. Biol. Chem.* 265(12):7084-7090 (1990).
Matthies and Schink, "Reciprocal Isomerization of Butyrate and Isobutyrate by the Strictly Anaerobic Bacterium Strain WoG13 and Methanogenic Isobutyrate Degradation by a Defined Triculture," *Appl. Environ. Microbiol.* 58(5):1435-1439 (1992).
McElwain et al., International Journal of Systematic Bacteriology, 38:417-423 (1988).
Metz et al., "Purification of a jojoba embryo fatty acyl-Coenzyme A reductase and expression of its cDNA in high erucic acid rapeseed," *Plant Phys.* 122:635-644 (2000).
Miallau et al., "Biosynthesis of isoprenoids: crystal structure of 4-diphosphocytidyl-2C-methyl-D-erythritol kinase," *Proc. Natl. Acad. Sci. U. S. A.* 100(16):9173-9178 (2003). (Epub Jul. 23, 2003).
Miller et al., "First isolation of an isoprene synthase gene from poplar and successful expression of the gene in *Escherichia coli*," *Planta* 213(3):483-487 (2001).
Moon et al., "Biotechnological production of erythritol and its applications," *Appl. Microbiol. Biotechnol.* 86(4):1017-1025 (2010). (Epub Feb. 26, 2010).
Morris and Jinks-Robertson, "Nucleotide sequence of the LYS2 gene of *Saccharomyces cerevisiae*: homology to Bacillus brevis tyrocidine synthetase 1," *Gene* 98:141-145 (1991).
Mouttaki et al., "Cyclohexane Carboxylate and Benzoate Formation from Crotonate in Syntrophus aciditrophicus," *Appl. Environl. Microbiol.* 73(3):930-938 (2007).
Müh et al., "4-Hydroxybutyryl-CoA dehydratase from Clostridium aminobutyricum: characterization of FAD and iron-sulfur clusters involved in an overall non-redox reaction," *Biochemistry* 35:11710-11718 (1996).

Müh et al., "Mössbauer study of 4-hydroxybutyryl-CoA dehydratase probing the role of an iron-sulfur cluster in an overall non-redox reaction," *Eur. J. Biochem.* 248:380-384 (1997).
Muller et al., "Nucleotide exchange and excisiion technology (NExT) DNA shuffling; a robust method for DNA fragmentation and directed evolution," *Nucleic Acids Res.* 33:e117 (2005).
Musfeldt and Schönheit, "Novel type of ADP-forming acetyl Coenzyme A synthetase in hyperthermophilic archaea: heterologous expression and characterization of isoenzymes from the sulfate reducer Archaeoglobus fulgidus and the methanogen Methanococcus jannaschii," *J. Bacteriol.* 184(3):636-644 (2002).
Naggert et al., "Cloning, sequencing, and characterization of *Escherichia coli* thioesterase II," *J. Biol. Chem.* 266(17):11044-11050 (1991).
Nelson et al., "Evidence for lateral gene transfer between Archaea and bacteria from genome sequence of Thermotoga maritima," *Nature* 399(6734):323-329 (1999).
Ness et al., "Synthetic shuffling expands functional protein diversity by allowing amino acids to recombine independently," *Nat. Biotechnol.* 20:1251-1255 (2002).
Nogales et al., "Characterization of the last step of the aerobic phenylacetic acid degradation pathway," *Microbiology* 153(Pt 2):357-365 (2007).
Oh et al., "Increased erythritol production in fed-batch cultures of *Torula* sp. by controlling glucose concentration," *J. Ind. Microbiol. Biotechnol.* 26(4):248-252 (2001).
Ohgami et al., "Expression of acetoacetyl-CoA synthetase, a novel cytosolic ketone body-utilizing enzyme, in human brain," *Biochem. Pharmacol.* 65:989-994 (2003).
Okada et al, "Cyanobacterial non-mevalonate pathway: (E)-4-hydroxy-3-methylbut-2-enyl diphosphate synthase interacts with ferredoxin in Thermosynechococcus elongatus BP-1," *J. Biol. Chem.* 280(21):20672-20679 (2005). (Epub Mar. 25, 2005).
Olivera et al., "Molecular characterization of the phenylacetic acid catabolic pathway in Pseudomonas putida U: the phenylacetyl-CoA catabolon," *Proc. Natl. Acad. Sci. U.S.A.* 95(11):6419-6424 (1998).
Ostermeier et al., "A Combinatorial approach to hybrid enzymes independent of DNA homology," *Nat. Biotechnol.* 17:1205-1209 (1999).
Ostermeier et al., "Combinatorial protein engineering by incremental truncation," *Proc. Natl. Acad. Sci. U.S.A.* 96:3562-3567 (1999).
Otten and Quax, "Directed evolution:selecting today's biocatalysts," *Biomol. Eng.* 22:1-9 (2005).
Park and Lee, "Biosynthesis of poly(3-hydroxybutyrate- co-3-hydroxyalkanoates) by metabolically engineered *Escherichia coli* strains," *Appl. Biochem. Biotechnol.* 113-116:335-346 (2004).
Park and Lee, "Identification and characterization of a new enoyl Coenzyme A hydratase involved in biosynthesis of medium-chain-length polyhydroxyalkanoates in recombinant *Escherichia coli*," *J. Bacteriol.* 185(18):5391-5397 (2003).
Park and Lee, "New FadB homologous enzymes and their use in enhanced biosynthesis of medium-chain-length polyhydroxyalkanoates in FadB mutant *Escherichia coli*," *Biotechnol. Bioeng.* 86(6):681-686 (2004).
Peoples and Sinskey, "Fine structural analysis of the Zoogloea ramigera phbA-phbB locus encoding β-ketothiolase and acetoacetyl-CoA reductase: nucleotide sequence of phbB," *Mol. Microbiol.* 3:349-357 (1989).
Peretz and Burstein, "Amino acid sequence of alcohol dehydrogenase from the thermophilic bacterium Thermoanaerobium brockii," *Biochemistry* 28(16):6549-6555 (1989).
Perez et al., "*Escherichia coli* YqhD exhibits aldehyde reductase activity and protects from the harmful effect of lipid peroxidation-derived aldehydes," *J. Biol. Chem.* 283(12):7346-7353 (2008).
Pilloff et al., "The kinetic mechanism of phosphomevalonate kinase," *J. Biol. Chem.* 278(7):4510-4515 (2003). (Epub Nov. 6, 2002).
Ploux et al., "The NADPH-linked acetoacetyl-CoA reductase from Zoogloea ramigera, Characterization and mechanistic studies of the cloned enzyme over-produced in *Escherichia coli*," *Eur. J. Biochem.* 174:177-182 (1988).
Powlowski et al., "Purification and properties of the physically associated meta-cleavage pathway enzymes 4-hydroxy-2-ketovalerate

(56) References Cited

OTHER PUBLICATIONS aldolase and aldehyde dehydrogenase (acylating) from *Pseudomonas* sp. strain CF600," *J. Bacteriol.* 175(2):377-385 (1993).
Pritchard et al., "A general model of error-prone PCR," *J. Theor. Biol.* 234:497-509 (2005).
Rajpal et al., "A general method for greatly improving the affinity of antibodies by using combinatorial libraries," *Proc. Natl. Acad. Sci. U.S.A.* 102:8466-8471 (2005).
Rathinasabapathi, "Propionate, a source of β-alanine, is an inhibitor of β-alanine methylation in Limonium latifoilium Plunbaginaces," *J. Plant Physiol.* 159:671-674 (2002).
Reetz and Carballeira, "Iterative saturation mutagenesis (ISM) for rapid directed evolution of functional enzymes," *Nat. Protoc.* 2:891-903 (2007).
Reetz et al., "Directed Evolution of an Enantioselective Enzyme through Combinatorial Multiple-Cassette Mutagenesis," *Angew. Chem. Int. Ed. Engl.* 40:3589-3591 (2001).
Reetz et al., "Iterative saturation mutagenesis on the basis of B factors as a strategy for incresing protein thermostability," *Angew. Chem. Int. Ed.* 45:7745-7751 (2006).
Reidhaar-Olson and Sauer, "Combinatorial cassette mutagenesis as a probe of the informational content of protein sequences," *Science* 241:53-57 (1988).
Reidhaar-Olson et al., "Random mutagenesis of protein sequences using oligonucleotide cassettes," *Methods Enzymmol.* 208:564-586 (1991).
Reiser and Somerville, "Isolation of mutants of Acinetobacter calcoaceticus deficient in wax ester synthesis and complementation of one mutation with a gene encoding a fatty acyl Coenzyme A reductase," *J. Bacteriol.* 179(9):2969-2975 (1997).
Richard et al., "Structure and mechanism of 2-C-methyl-D-erythritol 2,4-cyclodiphosphate synthase. An enzyme in the mevalonate-independent isoprenoid biosynthetic pathway," *J. Biol. Chem.* 277(10):8667-8672 (2002). (Epub Jan. 10, 2002).
Richard et al., "Structure of 4-diphosphocytidyl-2-C-methylerythritol synthetase involved in mevalonate- independent isoprenoid biosynthesis," *Nat. Struct. Biol.* 8(7):641-648 (2001).
Riviere et al., "Acetyl:succinate CoA-transferase in procyclic Trypanosoma brucei. Gene identification and role in carbohydrate metabolism." *J. Biol. Chem.* 279:45337-45346 (2004).
Roberts et al., "The Role of Enoyl-CoA Hydratase in the Metabolism of Isoleucine by Pseudomonas putida," *Arch. Microbiol.* 117:99-108 (1978).
Robinson et al., "Studies on Rat Brain Acyl-Coenzyme A Hydrolase (Short Chain)," *Biochem. Biophys. Res. Commun.* 71(4):959-965 (1976).
Rodríguez-Concepción et al., "Genetic evidence of branching in the isoprenoid pathway for the production of isopentenyl diphosphate and dimethylallyl diphosphate in *Escherichia coli*," *FEBS Lett.* 473(3):328-332 (2000).
Sasaki et al., "Gene expression and characterization of isoprene synthase from Populus alba," *FEBS Lett.* 579(11):2514-2518 (2005).
Sawada et al., "Key role for transketolase activity in erythritol production by Trichosporonoides megachiliensis SN-G42," *J. Biosci. Bioeng.* Nov. 2009;108(5):385-390 (2009). (Epub Jul. 29, 2009).
Scherf and Buckel, "Purification and properties of an iron-sulfur and FAD-containing 4-hydroxybutyryl-CoA dehadratase/vinylacetyl-CoA $\Delta^3$ - $\Delta^2$-isomerase from Clostridium aminobutricum," *Eur. J. Biochem.* 215:421-429 (1993).
Scherf et al, "Succinate-ethanol fermentation in clostridium kluyveri: purification and characterisation of 4-hydroxybutyryl-CoA dehydratase/vinylacetyl-CoA $\Delta^3$ - $\Delta^2$-isomerase," *Arch. Microbiol.* 161(3):239-245 (1994).
Schweiger and Buckel, "On the dehydration of (R)-lactate in the fermentation of alanine to propionat by Clostridium propionicum" *FEBS Lett.* 171:79-84 (1984).
Seemann et al., "Isoprenoid biosynthesis in chloroplasts via the methylerythritol phosphate pathway: the (E)-4-hydroxy-3-methylbut-2-enyl diphosphate synthase (GcpE) from Arabidopsis thaliana is a [4Fe-4S] protein," *J. Biol. Inorg. Chem.* 10(2):131-137 (2005). (Epub Jan. 14, 2005).
Selifonova et al., "Rapid evolution of novel traits in microorganisms," *Appl. Environ. Microbiol.* 67:3645-3649 (2001).
Selmer et al., "Propionate CoA-transferase from Clostridium propionicum. Cloning of gene identification of glutamate 324 at the active site," *Eur. J. Biochem.* 269:372-380 (2002).
Sen et al., "Developments in directed evolution for improving enzyme functins," *Appl. Biochem. Biotechnol.* 143:212-223 (2007).
Sgraja et al., "Characterization of Aquifex aeolicus 4-diphosphocytidyl-2C-methyl-d-erythritol kinase—ligand recognition in a template for antimicrobial drug discovery," *FEBS J.* 275(11):2779-2794 (2008). (Epub Apr. 16, 2008).
Shao et al., "Random-priming in vitro recombination: an effective tool for directed evolution," *Nucleic Acids Res.* 26:681-683 (1998).
Sharkey et al., "Evolution of the isoprene biosynthetic pathway in kudzu," *Plant Physiol.* 137(2):700-712 (2005). (Epub Jan. 14, 2005).
Shi et al., "Biosynthesis of isoprenoids: characterization of a functionally active recombinant 2-C-methyl-D-erythritol 4-phosphate cytidyltransferase (IspD) from *Mycobacterium tuberculosis* H37Rv," *J. Biochem. Mol. Biol.* 40(6):911-920 (2007).
Shimomura et al., "3-hydroxyisobutyryl-CoA hydrolase," *Methods Enzymol.* 324:229-240 (2000).
Shimomura et al., "Purification and partial characterization of 3-hydroxyisobutyryl-Coenzyme A hydrolase of rat liver," *J. Biol. Chem.* 269(19):14248-14253 (1994).
Sibilli et al., "Two regions of the bifunctional protein aspartokinase I-homoserine dehydrogenase I are connected by a short hinge," *J. Biol. Chem.* 256 (20):10228-10230 (1981).
Sieber et al., "Libraries of hybrid proteins from distantly related sequences," *Nat. Biotechnol.* 19:456-460 (2001).
Slater et al., "Multiple β-ketothiolases mediate poly(β-hydroxyalkanoate) copolymer synthesis in Ralstonia eutropha," *J. Bacteriol.* 180(8):1979-1987 (1998).
Söhling and Gottschalk, "Molecular analysis of the anaerobic succinate degradation pathway in Clostridium kluyveri," *J. Bacteriol.* 178:871-880 (1996).
Söhling and Gottschalk, "Purification and characterization of a Coenzyme-A-dependent succinate-semialdehyde dehydrogenase from Clostridium kluyveri," *Eur. J. Biochem.* 212:121-127 (1993).
Song et al., "Structure, function, and mechanism of the phenylacetate pathway hot dog-fold thioesterase PaaI," *J. Biol. Chem.* 281(16):11028-11038 (2006).
Sperry et al., "Erythritol catabolism by Brucella abortus," *J. Bacteriol.* 121(2):619-630 (1975).
Stadtman, "The enzyme synthesis of β-alanyl Coenzyme A," *J. Plant Chem. Soc.* 77:5765-5766 (1955).
Starnes et al., "Threonine-sensitive aspartokinase-homoserine dehydrogenase complex, amino acid composition, molecular weight, and subunit composition of the complex," *Biochemistry* 11:677-687 (1973).
Steinbacher et al., "Structure of 2C-methyl-d-erythritol-2,4-cyclodiphosphate synthase involved in mevalonate-independent biosynthesis of isoprenoids," *J. Mol. Biol.* 316(1):79-88 (2002).
Steinbüchel and Schlegel, "NAD-linked L(+)-lactate dehydrogenase from the strict aerobe alcaligenes eutrophus. 2. Kinetic properties and inhibition by oxaloacetate," *Eur. J. Biochem.* 130(2):329-334 (1983).
Stemmer, "DNA shuffling by random fragmentation and reassembly: in vitro recombination for molecular evolution," *Proc. Natl. Acad. Sci. U.S.A.* 91:10747-10751 (1994).
Stemmer, "Rapid evolution of a protein in vitro by DNA shuffling," *Nature* 370:389-391 (1994).
Stols et al., "New vectors for co-expression of proteins: Structure of Bacillus subtilis ScoAB obtained by High-throughput protocols," *Protein Expr. Purif.* 53:396-403 (2007).
Strauss and Fuchs, "Enzymes of a novel autotrophic CO2 fixation pathway in the phototrophic bacterium Chloroflexus aurantiacus, the 3-hydroxypropionate cycle," *Eur. J. Biochem.* 215:633-643 (1993).
Suda et al., "Purification and properties of α-ketoadipate reductase, a newly discovered enzyme from human placenta," *Arch. Biochem. Biophys.* 176(2):610-620 (1976).

(56) References Cited

OTHER PUBLICATIONS

Suda et al., "Subcellular localization and tissue distribution of α-ketoadipate reduction and oxidation in the rat," *Biochem. Biophys. Res. Commun.* 77(2):586-591 (1977).

Sulzenbacher et al., "Crystal structure of *E.coli* alcohol dehydrogenase YqhD: evidence of a covalently modified NADP Coenzyme," *J. Mol. Biol.* 342(2):489-502 (2004).

Suzuki et al., "GriC and GriD Constitute a carboxylic acid reductase involved in grixazone biosynthesis in *Streptomyces griseus*," *J. Antibiot.* 60(6):380-387 (2007).

Takahashi and Yamada, "Metabolic pathways for cytoxic and end product formation from glutamate- and aspartate-containing peptides by Porphyromonas gingivalis," *J. Bacteriol.* 182:4704-4710 (2000).

Tani et al., "Thermostable NADP+-dependent medium-chain alcohol dehydrogenase from *Acinetobacter* sp. strain M-1: purification and characterization and gene expression in *Escherichia coli*," *Appl. Environ. Microbiol.* 66(12):5231-5235 (2000).

Thauer, "Microbiology. A Fifth Pathway of Carbon Fixation," *Science* 318:1732-1733 (2007).

Toth et al., "Molecular cloning and expression of the cDNAs encoding human and yeast mevalonate pyrophosphate decarboxylase," *J. Biol. Chem.* 271(14):7895-7898 (1996).

Toth et al., "The ald Gene, Encoding a Coenzyme A—Acylating Aldehyde Dehydrogenase, Distinguishes Clostridium beijerinckii and Two Other Solvent-Producing Clostridia from Clostridium acetobutylicum," *App. Environ. Microbiol.* 65(11):4973-4980 (1999).

Toussaint et al., "Production of Butadiene from Alcohol," *Ind. Eng. Chem.* 39(2):120-125 (1947).

Tsay and Robinson, "Cloning and characterization of ERG8, an essential gene of *Saccharomyces cerevisiae* that encodes phosphomevalonate kinase," *Mol. Cell Biol.* 11(2):620-631 (1991).

Vamecq et al., "The microsomal dicarboxylyl-CoA synthetase," *Biochem. J.* 230(3):683-693 (1985).

van der Voorhorst et al., "Genetic and biochemcial characterization of a short-chain alcohol dehydrogenase from the hyperthermophilic archaeon Pyrococcus furiosus," *Eur. J. Biochem.* 268:3062-3068 (2001).

Van Ginkel et al., "Metabolism of trans-2-Butene and Butane in Nocardia TB1," *J. Gen. Microbiol.* 133:1713-1720 (1987).

van Grinsven et al., "Acetate:succinate CoA-transferase in the hydrogenosomes of Trichomonas vaginalis: identification and characterization," *J. Biol. Chem.* 283:1411-1418 (2008).

Vanderwinkel et al., "Growth of *Escherichia coli* on fatty acids: requirement for Coenzyme A transferase activity," *Biochem. Biophys. Res. Commun.* 33(6):902-908 (1968).

Veiga-da-Cunha et al., "Pathway and regulation of erythritol formation in Leuconostoc oenos," *J. Bacteriol.* 175(13):3941-3948 (1993).

Venkitasubramanian et al. in *Biocatalysis in the Pharmaceutical and Biotechnology Industries*, ed. R.N. Patel, Chapter 15, pp. 425-440, CRC Press LLC, Boca Raton, FL. 2007.

Venkitasubramanian et al., "Reduction of Carboxylic Acids by Nocardia Aldehyde Oxidoreductase Requires a Phosphopantetheinylated Enzyme," *J. Biol. Chem.* 282(1):478-485 (2007).

Volkov et al., "Random chimeragenesis by heteroduplex recombination," *Methods Enzymol.* 328:456-463 (2000).

Volkov et al., "Recombination and chimeragenesis by in vitro heteroduplex formation and in vivo repair," *Nucleic Acids Res.* 27:e18 (1999).

Wada et al., "Crystal structure of 4-(cytidine 5'-diphospho)-2-C-methyl-D-erythritol kinase, an enzyme in the non-mevalonate pathway of isoprenoid synthesis," *J. Biol. Chem.* 278(32):30022-30027 (2003). (Epub May 27, 2003).

Wakil et al., "Studies on the fatty acid oxidizing system of animal tissues. VI. β-Hydroxyacyl Coenzyme A dehydrogenase," *J. Biol. Chem.* 207(2):631-638 (1954).

Walter et al., "Molecular characterization of two Clostridium acetobutylicum ATCC 824 butanol dehydrogenase isozyme genes," *J. Bacteriol.* 174(22):7149-7158 (1992).

Wang et al, "Molecular cloning and functional identification of a novel phenylacetyl-CoA ligase gene from Penicillium chrysogenum," *Biochem. Biopyhs. Res. Commun.* 360(2):453-458 (2007).

Westin et al., "The identification of a succinyl-CoA thioesterase suggests a novel pathway for succinate production in peroxisomes," *J. Biol. Chem.* 280(46):38125-38132 (2005).

Wilding et al., "Identification, evolution, and essentiality of the mevalonate pathway for isopentenyl diphosphate biosynthesis in gram-positive cocci," *J. Bacteriol.* 182(15):4319-4327 (2000).

Winzer et al., "Differential regulation of two thiolase genes from Clostridium acetobutylicum DSM 792," *J. Mol. Microbiol. Biotechnol.* 2(4):531-541 (2000).

Wolff and Kenealy, "Purification and characterization of the oxygen-sensitive 4-hydroxybutanoate dehydrogenase from Clostridium kluyveri," *Protein Expr. Purif.* 6:206-212 (1995).

Wolff et al., "Isoprenoid biosynthesis via the methylerythritol phosphate pathway: the (E)-4-hydroxy-3-methylbut-2-enyl diphosphate reductase (LytB/IspH) from *Escherichia coli* is a [4Fe-4S] protein," *FEBS Lett.* 541(1-3):115-120 (2003).

Wong et al., "Sequence saturation mutagenesis (SeSaM): a novel method for directed evolution," *Nucleic Acids Res.* 32:e26 (2004).

Wong et al., "Sequence saturation mutagenesis with tunable mutation frequencies," *Anal. Biochem.* 341:187-189 (2005).

Wong et al., "Transversion-enriched sequence saturation mutagenesis (SeSaM-Tv+): a random mutagenesis method with consecutive nucleotide exchanges that complements the bias of error-prone PCR," *Biotechnol. J.* 3:74-82 (2008).

Yajima et al., "Structure of 1-deoxy-D-xylulose 5-phosphate reductoisomerase in a quaternary complex with a magnesium ion, NADPH and the antimalarial drug fosmidomycin," *Acta Crystallogr. Sect. F Struct. Biol. Cryst. Commun.* 63(Pt 6):466-470 (2007). (Epub May 31, 2007).

Yamashita et al., "Type 2 isopentenyl diphosphate isomerase from a thermoacidophilic archaeon Sulfolobus shibatae," *Eur. J. Biochem.* 2271(6):1087-1093 (2004).

Youngleson et al., "Homology between hydroxybutyryl and hydroxyacyl Coenzyme A dehydrogenase enzymes from Clostridium acetobutylicum fermentation and vertebrate fatty acid β-oxidation pathways," *J. Bacteriol.* 171(12):6800-6807 (1989).

Zeiher and Randall, "Identification and characterization of Mitochondrial Acetyl-Coenzyme A Hydrolase from *Pisum sativum* L. Seedlings," *Plant. Physiol.* 94:20-27 (1990).

Zepeck et al., "Biosynthesis of isoprenoids. purification and properties of IspG protein from *Escherichia coli*," *J. Org. Chem.* 70(23):9168-9174 (2005).

Zhao et al., "Molecular evolution by staggered extension process (StEP) in vitro recombination," *Nat. Biotechnol.* 16:258-261 (1998).

Zhuang, et al., "The YbgC protein encoded by the ybgC gene of the tol-pal gene cluster of Haemophilus influenzae catalyzes acyl-Coenzyme A thioester hydrolysis," *FEBS Lett.* 516(1-3):161-163 (2002).

Public domain data on 3-aminobutyryl-CoA deaminase at Explor-Enz. 1999. [retrieved on Apr. 23, 2012]. Retrieved from internet URL <http://www.enzyme-database.org/query.php?ec=4.3.1.14>.

Public domain data on glutaconyl-CoA decarboxylase at EMBL-EBI. 2003. [retrieved on Apr. 24, 2012]. Retrieved from internet URL <http://www.ebi.ac.uk/intenz/query?cmd=SearchEC&ec=4.1.1.70>.

Public domain data on glutaryl-CoA dehydrogenase at NCBI MESH. Jun. 30, 2005 [retrieved on Apr. 23, 2012]. Retrieved from internet URL <http://www.nlm.nih.gov/cgi/mesh/2011/MB_cgi?mode=&term=Glutaryl-CoA+dehydrogenase>.

Adams, "Selectivity effects in some catalytic oxidation processes," Industrial and Engineering Chemistry, 61(6):30-38 (1969).

\* cited by examiner

US 9,321,701 B2

MICROORGANISMS AND METHODS FOR THE BIOSYNTHESIS OF BUTADIENE

This application claims the benefit of priority of U.S. Provisional application Ser. No. 61/438,947, filed Feb. 2, 2011, the entire contents of which are incorporated herein by reference.

BACKGROUND OF THE INVENTION

The present invention relates generally to biosynthetic processes, and more specifically to organisms having butadiene biosynthetic capability.

Over 25 billion pounds of butadiene (1,3-butadiene, BD) are produced annually and is applied in the manufacture of polymers such as synthetic rubbers and ABS resins, and chemicals such as hexamethylenediamine and 1,4-butanediol. Butadiene is typically produced as a by-product of the steam cracking process for conversion of petroleum feedstocks such as naphtha, liquefied petroleum gas, ethane or natural gas to ethylene and other olefins. The ability to manufacture butadiene from alternative and/or renewable feedstocks would represent a major advance in the quest for more sustainable chemical production processes One possible way to produce butadiene renewably involves fermentation of sugars or other feedstocks to produce diols, such as 1,4-butanediol or 1,3-butanediol, which are separated, purified, and then dehydrated to butadiene in a second step involving metal-based catalysis. Direct fermentative production of butadiene from renewable feedstocks would obviate the need for dehydration steps and butadiene gas (bp −4.4° C.) would be continuously emitted from the fermenter and readily condensed and collected. Developing a fermentative production process would eliminate the need for fossil-based butadiene and would allow substantial savings in cost, energy, and harmful waste and emissions relative to petrochemically-derived butadiene.

Microbial organisms and methods for effectively producing butadiene from cheap renewable feedstocks such as molasses, sugar cane juice, and sugars derived from biomass sources, including agricultural and wood waste, as well as C1 feedstocks such as syngas and carbon dioxide, are described herein and include related advantages.

SUMMARY OF THE INVENTION

The invention provides non-naturally occurring microbial organisms containing butadiene pathways comprising at least one exogenous nucleic acid encoding a butadiene pathway enzyme expressed in a sufficient amount to produce butadiene. The invention additionally provides methods of using such microbial organisms to produce butadiene, by culturing a non-naturally occurring microbial organism containing butadiene pathways as described herein under conditions and for a sufficient period of time to produce butadiene.

In some aspects, embodiments disclosed herein relate to a process for the production of butadiene that includes (a) culturing by fermentation in a sufficient amount of nutrients and media a non-naturally occurring microbial organism that produces crotyl alcohol; and (b) converting crotyl alcohol, produced by culturing the non-naturally occurring microbial organism, to butadiene.

DETAILED DESCRIPTION OF THE INVENTION

The present invention is directed to the design and production of cells and organisms having biosynthetic production capabilities for butadiene. The invention, in particular, relates to the design of microbial organism capable of producing butadiene by introducing one or more nucleic acids encoding a butadiene pathway enzyme.

In one embodiment, the invention utilizes in silico stoichiometric models of *Escherichia coli* metabolism that identify metabolic designs for biosynthetic production of butadiene. The results described herein indicate that metabolic pathways can be designed and recombinantly engineered to achieve the biosynthesis of butadiene in *Escherichia coli* and other cells or organisms. Biosynthetic production of butadiene, for example, for the in silico designs can be confirmed by construction of strains having the designed metabolic genotype. These metabolically engineered cells or organisms also can be subjected to adaptive evolution to further augment butadiene biosynthesis, including under conditions approaching theoretical maximum growth.

In certain embodiments, the butadiene biosynthesis characteristics of the designed strains make them genetically stable and particularly useful in continuous bioprocesses. Separate strain design strategies were identified with incorporation of different non-native or heterologous reaction capabilities into *E. coli* or other host organisms leading to butadiene producing metabolic pathways from acetyl-CoA, glutaconyl-CoA, glutaryl-CoA, 3-aminobutyryl-CoA, 4-hydroxybutyryl-CoA, erythrose-4-phosphate or malonyl-CoA plus acetyl-CoA. In silico metabolic designs were identified that resulted in the biosynthesis of butadiene in microorganisms from each of these substrates or metabolic intermediates.

Strains identified via the computational component of the platform can be put into actual production by genetically engineering any of the predicted metabolic alterations, which lead to the biosynthetic production of butadiene or other intermediate and/or downstream products. In yet a further embodiment, strains exhibiting biosynthetic production of these compounds can be further subjected to adaptive evolution to further augment product biosynthesis. The levels of product biosynthesis yield following adaptive evolution also can be predicted by the computational component of the system.

The maximum theoretical butadiene yield from glucose is 1.09 mol/mol (0.33 g/g).

$$11C_6H_{12}O_6 = 12C_4H_6 + 18CO_2 + 30H_2O$$

Figure 2:
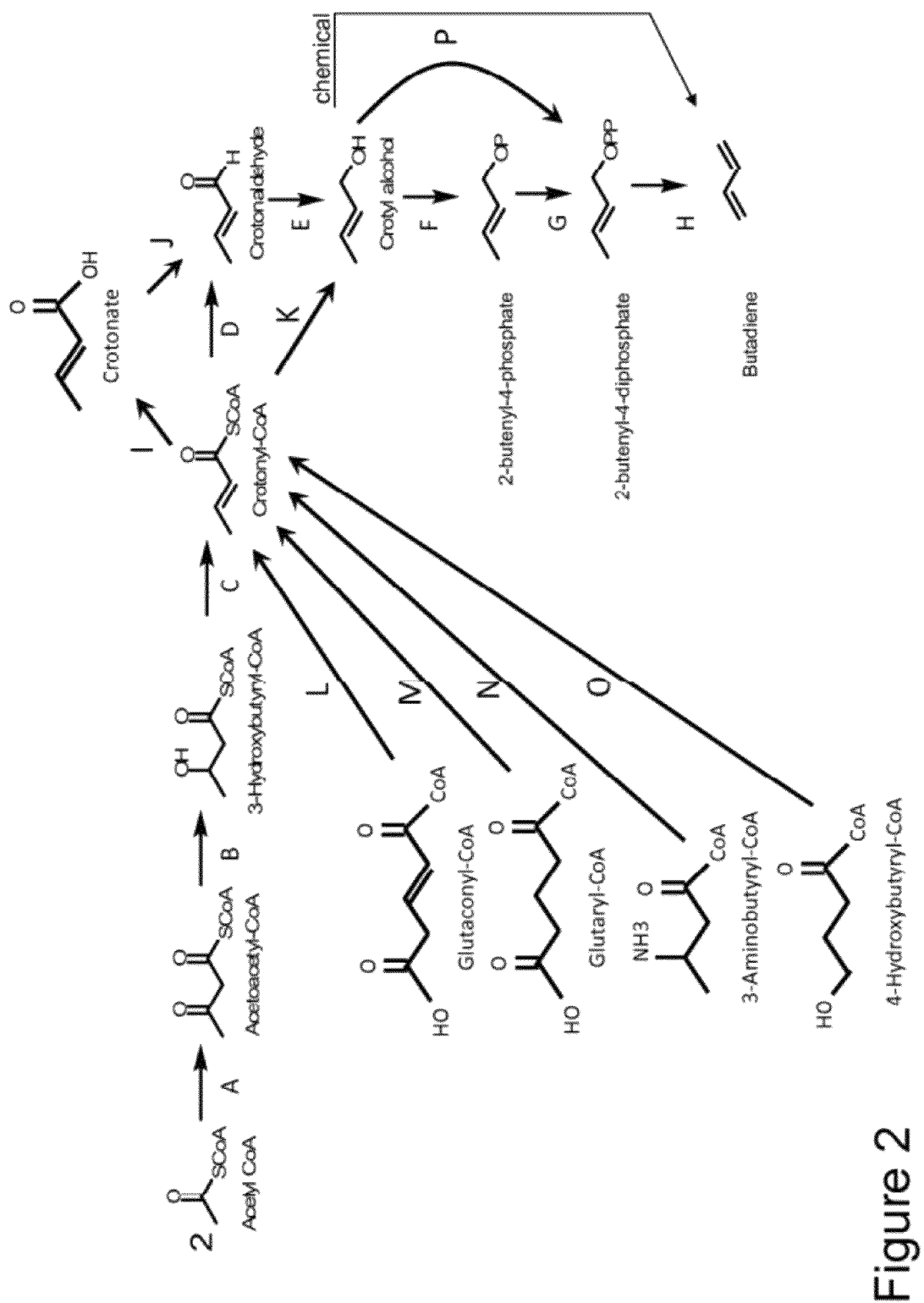
FIG. 2 shows exemplary pathways for production of butadiene from acetyl-CoA, glutaconyl-CoA, glutaryl-CoA, 3-aminobutyryl-CoA or 4-hydroxybutyryl-CoA via crotyl alcohol. Enzymes for transformation of the identified substrates to products include: A. acetyl-CoA:acetyl-CoA acyltransferase, B. acetoacetyl-CoA reductase, C. 3-hydroxybutyryl-CoA dehydratase, D. crotonyl-CoA reductase (aldehyde forming), E. crotonaldehyde reductase (alcohol forming), F. crotyl alcohol kinase, G. 2-butenyl-4-phosphate kinase, H. butadiene synthase, I. crotonyl-CoA hydrolase, synthetase, transferase, J. crotonate reductase, K. crotonyl-CoA reductase (alcohol forming), L. glutaconyl-CoA decarboxylase, M., glutaryl-CoA dehydrogenase, N. 3-aminobutyryl-CoA deaminase, O. 4-hydroxybutyryl-CoA dehydratase, P. crotyl alcohol diphosphokinase. The chemical pathway to butadiene utilizes dehydration processes.
Figure 3:
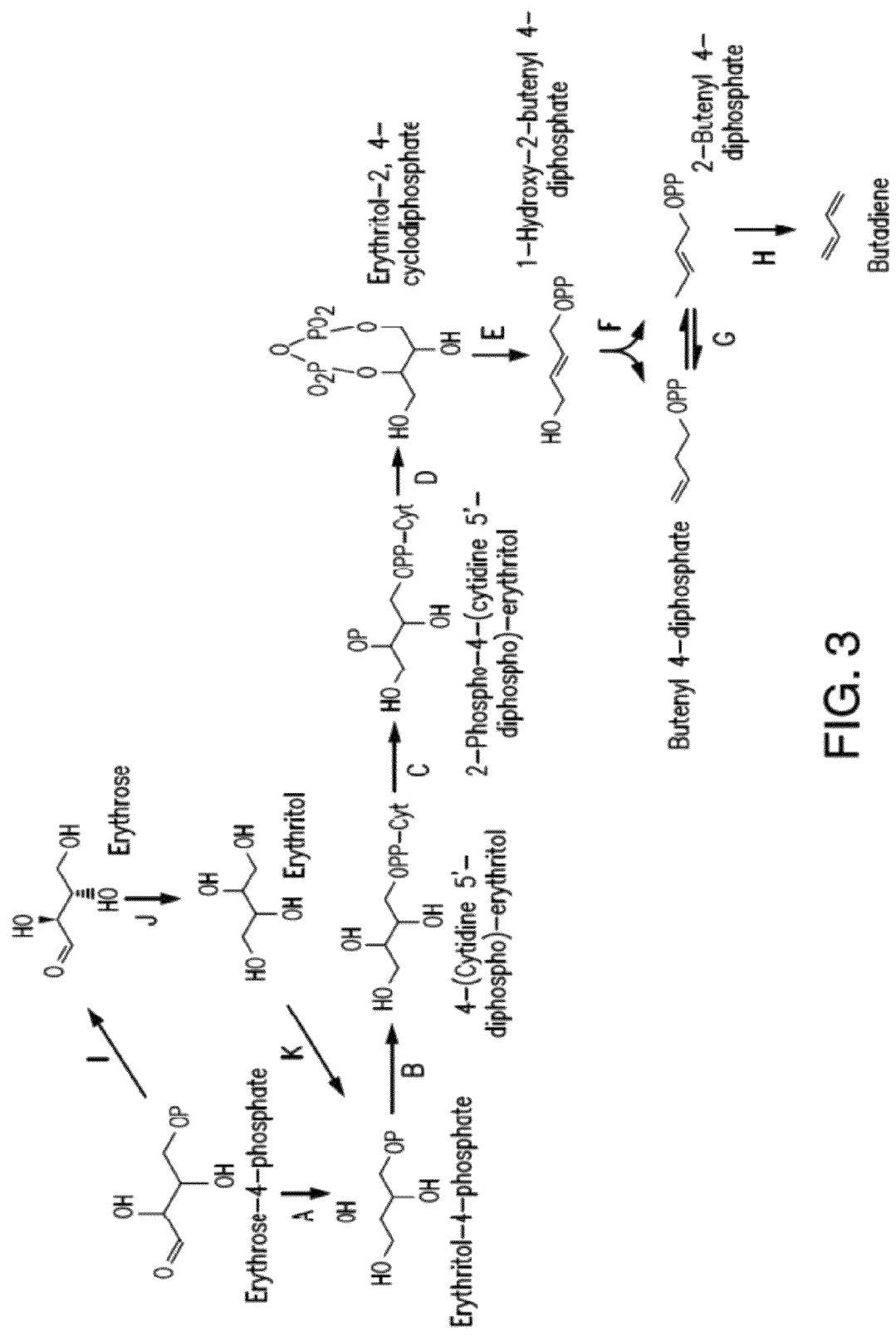
FIG. 3 shows exemplary pathways for production of butadiene from erythrose-4-phosphate. Enzymes for transformation of the identified substrates to products include: A. Erythrose-4-phosphate reductase, B. Erythritol-4-phospate cytidylyltransferase, C. 4-(cytidine 5'-diphospho)-erythritol kinase, D. Erythritol 2,4-cyclodiphosphate synthase, E. 1-Hydroxy-2-butenyl 4-diphosphate synthase, F. 1-Hydroxy-2-butenyl 4-diphosphate reductase, G. Butenyl 4-diphosphate isomerase, H. Butadiene synthase I. Erythrose-4-phosphate kinase, J. Erythrose reductase, K. Erythritol kinase.
Figure 4:
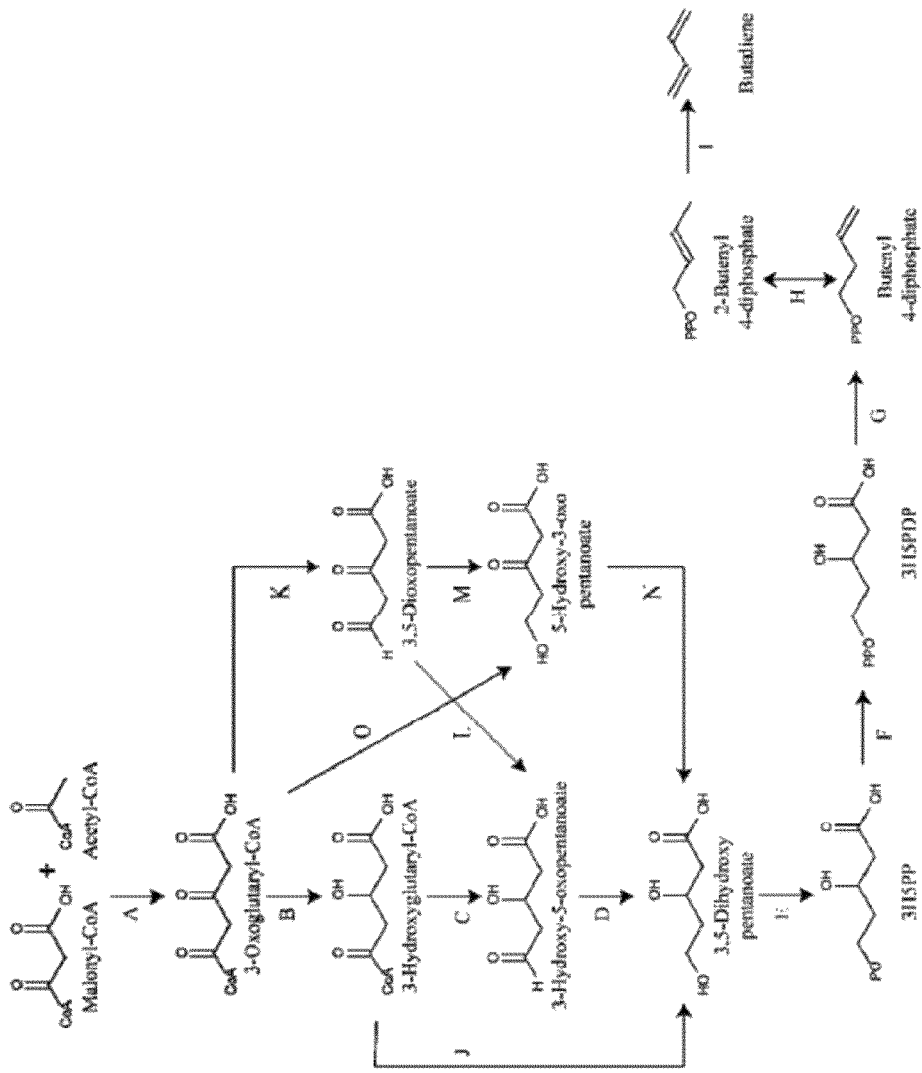
FIG. 4 shows an exemplary pathway for production of butadiene from malonyl-CoA plus acetyl-CoA. Enzymes for transformation of the identified substrates to products include: A. malonyl-CoA:acetyl-CoA acyltransferase, B. 3-oxoglutaryl-CoA reductase (ketone-reducing), C. 3-hydroxyglutaryl-CoA reductase (aldehyde forming), D. 3-hydroxy-5-oxopentanoate reductase, E. 3,5-dihydroxypentanoate kinase, F. 3H5PP kinase, G. 3H5PDP decarboxylase, H. butenyl 4-diphosphate isomerase, I. butadiene synthase, J. 3-hydroxyglutaryl-CoA reductase (alcohol forming), K. 3-oxoglutaryl-CoA reductase (aldehyde forming), L. 3,5-dioxopentanoate reductase (ketone reducing), M. 3,5-dioxopentanoate reductase (aldehyde reducing), N. 5-hydroxy-3-oxopentanoate reductase, O. 3-oxo-glutaryl-CoA reductase (CoA reducing and alcohol forming). Compound abbreviations include: 3H5PP=3-Hydroxy-5-phosphonatooxypentanoate and 3H5PDP=3-Hydroxy-5-[hydroxy(phosphonooxy)phosphoryl]oxy pentanoate.

The pathways presented in FIGS. 2 and 4 achieve a yield of 1.0 moles butadiene per mole of glucose utilized. Increasing product yields to theoretical maximum value is possible if cells are capable of fixing $CO_2$ through pathways such as the reductive (or reverse) TCA cycle or the Wood-Ljungdahl pathway. Organisms engineered to possess the pathway depicted in FIG. 3 are also capable of reaching near theoretical maximum yields of butadiene.

As used herein, the term "non-naturally occurring" when used in reference to a microbial organism or microorganism of the invention is intended to mean that the microbial organism has at least one genetic alteration not normally found in a naturally occurring strain of the referenced species, including wild-type strains of the referenced species. Genetic alterations include, for example, modifications introducing expressible nucleic acids encoding metabolic polypeptides, other nucleic acid additions, nucleic acid deletions and/or other functional disruption of the microbial organism's genetic material. Such modifications include, for example, coding regions and functional fragments thereof, for heterologous, homologous or both heterologous and homologous polypeptides for the referenced species. Additional modifications include, for example, non-coding regulatory regions in which the modifications alter expression of a gene or operon. Exemplary metabolic polypeptides include enzymes or proteins within a butadiene biosynthetic pathway.

A metabolic modification refers to a biochemical reaction that is altered from its naturally occurring state. Therefore, non-naturally occurring microorganisms can have genetic modifications to nucleic acids encoding metabolic polypeptides, or functional fragments thereof. Exemplary metabolic modifications are disclosed herein.

As used herein, the term "butadiene," having the molecular formula $C_4H_6$ and a molecular mass of 54.09 g/mol (see FIGS. 2-4) (IUPAC name Buta-1,3-diene) is used interchangeably throughout with 1,3-butadiene, biethylene, erythrene, divinyl, vinylethylene. Butadiene is a colorless, non corrosive liquefied gas with a mild aromatic or gasoline-like odor. Butadiene is both explosive and flammable because of its low flash point.

As used herein, the term "isolated" when used in reference to a microbial organism is intended to mean an organism that is substantially free of at least one component as the referenced microbial organism is found in nature. The term includes a microbial organism that is removed from some or all components as it is found in its natural environment. The term also includes a microbial organism that is removed from some or all components as the microbial organism is found in non-naturally occurring environments. Therefore, an isolated microbial organism is partly or completely separated from other substances as it is found in nature or as it is grown, stored or subsisted in non-naturally occurring environments. Specific examples of isolated microbial organisms include partially pure microbes, substantially pure microbes and microbes cultured in a medium that is non-naturally occurring.

As used herein, the terms "microbial," "microbial organism" or "microorganism" are intended to mean any organism that exists as a microscopic cell that is included within the domains of archaea, bacteria or eukarya. Therefore, the term is intended to encompass prokaryotic or eukaryotic cells or organisms having a microscopic size and includes bacteria, archaea and eubacteria of all species as well as eukaryotic microorganisms such as yeast and fungi. The term also includes cell cultures of any species that can be cultured for the production of a biochemical.

As used herein, the term "CoA" or "coenzyme A" is intended to mean an organic cofactor or prosthetic group (nonprotein portion of an enzyme) whose presence is required for the activity of many enzymes (the apoenzyme) to form an active enzyme system. Coenzyme A functions in certain condensing enzymes, acts in acetyl or other acyl group transfer and in fatty acid synthesis and oxidation, pyruvate oxidation and in other acetylation.

As used herein, the term "substantially anaerobic" when used in reference to a culture or growth condition is intended to mean that the amount of oxygen is less than about 10% of saturation for dissolved oxygen in liquid media. The term also is intended to include sealed chambers of liquid or solid medium maintained with an atmosphere of less than about 1% oxygen.

"Exogenous" as it is used herein is intended to mean that the referenced molecule or the referenced activity is introduced into the host microbial organism. The molecule can be introduced, for example, by introduction of an encoding nucleic acid into the host genetic material such as by integration into a host chromosome or as non-chromosomal genetic material such as a plasmid. Therefore, the term as it is used in reference to expression of an encoding nucleic acid refers to introduction of the encoding nucleic acid in an expressible form into the microbial organism. When used in reference to a biosynthetic activity, the term refers to an activity that is introduced into the host reference organism. The source can be, for example, a homologous or heterologous encoding nucleic acid that expresses the referenced activity following introduction into the host microbial organism. Therefore, the term "endogenous" refers to a referenced molecule or activity that is present in the host. Similarly, the term when used in reference to expression of an encoding nucleic acid refers to expression of an encoding nucleic acid contained within the microbial organism. The term "heterologous" refers to a molecule or activity derived from a source other than the referenced species whereas "homologous" refers to a molecule or activity derived from the host microbial organism. Accordingly, exogenous expression of an encoding nucleic acid of the invention can utilize either or both a heterologous or homologous encoding nucleic acid.

It is understood that when more than one exogenous nucleic acid is included in a microbial organism that the more than one exogenous nucleic acids refers to the referenced encoding nucleic acid or biosynthetic activity, as discussed above. It is further understood, as disclosed herein, that such more than one exogenous nucleic acids can be introduced into the host microbial organism on separate nucleic acid molecules, on polycistronic nucleic acid molecules, or a combination thereof, and still be considered as more than one exogenous nucleic acid. For example, as disclosed herein a microbial organism can be engineered to express two or more exogenous nucleic acids encoding a desired pathway enzyme or protein. In the case where two exogenous nucleic acids encoding a desired activity are introduced into a host microbial organism, it is understood that the two exogenous nucleic acids can be introduced as a single nucleic acid, for example, on a single plasmid, on separate plasmids, can be integrated into the host chromosome at a single site or multiple sites, and still be considered as two exogenous nucleic acids. Similarly, it is understood that more than two exogenous nucleic acids can be introduced into a host organism in any desired combination, for example, on a single plasmid, on separate plasmids, can be integrated into the host chromosome at a single site or multiple sites, and still be considered as two or more exogenous nucleic acids, for example three exogenous nucleic acids. Thus, the number of referenced exogenous nucleic acids or biosynthetic activities refers to the number of encoding nucleic acids or the number of biosynthetic activities, not the number of separate nucleic acids introduced into the host organism.

The non-naturally occurring microbial organisms of the invention can contain stable genetic alterations, which refers to microorganisms that can be cultured for greater than five generations without loss of the alteration. Generally, stable genetic alterations include modifications that persist greater than 10 generations, particularly stable modifications will persist more than about 25 generations, and more particularly, stable genetic modifications will be greater than 50 generations, including indefinitely.

Those skilled in the art will understand that the genetic alterations, including metabolic modifications exemplified herein, are described with reference to a suitable host organism such as *E. coli* and their corresponding metabolic reactions or a suitable source organism for desired genetic material such as genes for a desired metabolic pathway. However, given the complete genome sequencing of a wide variety of organisms and the high level of skill in the area of genomics, those skilled in the art will readily be able to apply the teachings and guidance provided herein to essentially all other organisms. For example, the *E. coli* metabolic alterations exemplified herein can readily be applied to other species by incorporating the same or analogous encoding nucleic acid from species other than the referenced species. Such genetic alterations include, for example, genetic alterations of species homologs, in general, and in particular, orthologs, paralogs or nonorthologous gene displacements.

An ortholog is a gene or genes that are related by vertical descent and are responsible for substantially the same or identical functions in different organisms. For example, mouse epoxide hydrolase and human epoxide hydrolase can be considered orthologs for the biological function of hydrolysis of epoxides. Genes are related by vertical descent when, for example, they share sequence similarity of sufficient amount to indicate they are homologous, or related by evolution from a common ancestor. Genes can also be considered orthologs if they share three-dimensional structure but not necessarily sequence similarity, of a sufficient amount to indicate that they have evolved from a common ancestor to the extent that the primary sequence similarity is not identifiable. Genes that are orthologous can encode proteins with sequence similarity of about 25% to 100% amino acid sequence identity. Genes encoding proteins sharing an amino acid similarity less that 25% can also be considered to have arisen by vertical descent if their three-dimensional structure also shows similarities. Members of the serine protease family of enzymes, including tissue plasminogen activator and elastase, are considered to have arisen by vertical descent from a common ancestor.

Orthologs include genes or their encoded gene products that through, for example, evolution, have diverged in structure or overall activity. For example, where one species encodes a gene product exhibiting two functions and where such functions have been separated into distinct genes in a second species, the three genes and their corresponding products are considered to be orthologs. For the production of a biochemical product, those skilled in the art will understand that the orthologous gene harboring the metabolic activity to be introduced or disrupted is to be chosen for construction of the non-naturally occurring microorganism. An example of orthologs exhibiting separable activities is where distinct activities have been separated into distinct gene products between two or more species or within a single species. A specific example is the separation of elastase proteolysis and plasminogen proteolysis, two types of serine protease activity, into distinct molecules as plasminogen activator and elastase. A second example is the separation of mycoplasma 5'-3' exonuclease and *Drosophila* DNA polymerase III activity. The DNA polymerase from the first species can be considered an ortholog to either or both of the exonuclease or the polymerase from the second species and vice versa.

In contrast, paralogs are homologs related by, for example, duplication followed by evolutionary divergence and have similar or common, but not identical functions. Paralogs can originate or derive from, for example, the same species or from a different species. For example, microsomal epoxide hydrolase (epoxide hydrolase I) and soluble epoxide hydrolase (epoxide hydrolase II) can be considered paralogs because they represent two distinct enzymes, co-evolved from a common ancestor, that catalyze distinct reactions and have distinct functions in the same species. Paralogs are proteins from the same species with significant sequence similarity to each other suggesting that they are homologous, or related through co-evolution from a common ancestor. Groups of paralogous protein families include HipA homologs, luciferase genes, peptidases, and others.

A nonorthologous gene displacement is a nonorthologous gene from one species that can substitute for a referenced gene function in a different species. Substitution includes, for example, being able to perform substantially the same or a similar function in the species of origin compared to the referenced function in the different species. Although generally, a nonorthologous gene displacement will be identifiable as structurally related to a known gene encoding the referenced function, less structurally related but functionally similar genes and their corresponding gene products nevertheless will still fall within the meaning of the term as it is used herein. Functional similarity requires, for example, at least some structural similarity in the active site or binding region of a nonorthologous gene product compared to a gene encoding the function sought to be substituted. Therefore, a nonorthologous gene includes, for example, a paralog or an unrelated gene.

Therefore, in identifying and constructing the non-naturally occurring microbial organisms of the invention having butadiene biosynthetic capability, those skilled in the art will understand with applying the teaching and guidance provided herein to a particular species that the identification of metabolic modifications can include identification and inclusion or inactivation of orthologs. To the extent that paralogs and/or nonorthologous gene displacements are present in the referenced microorganism that encode an enzyme catalyzing a similar or substantially similar metabolic reaction, those skilled in the art also can utilize these evolutionarily related genes.

Orthologs, paralogs and nonorthologous gene displacements can be determined by methods well known to those skilled in the art. For example, inspection of nucleic acid or amino acid sequences for two polypeptides will reveal sequence identity and similarities between the compared sequences. Based on such similarities, one skilled in the art can determine if the similarity is sufficiently high to indicate the proteins are related through evolution from a common ancestor. Algorithms well known to those skilled in the art, such as Align, BLAST, Clustal W and others compare and determine a raw sequence similarity or identity, and also determine the presence or significance of gaps in the sequence which can be assigned a weight or score. Such algorithms also are known in the art and are similarly applicable for determining nucleotide sequence similarity or identity. Parameters for sufficient similarity to determine relatedness are computed based on well known methods for calculating statistical similarity, or the chance of finding a similar match in a random polypeptide, and the significance of the match determined. A computer comparison of two or more sequences can, if desired, also be optimized visually by those skilled in the art. Related gene products or proteins can be expected to have a high similarity, for example, 25% to 100% sequence identity. Proteins that are unrelated can have an identity which is essentially the same as would be expected to occur by chance, if a database of sufficient size is scanned (about 5%). Sequences between 5% and 24% may or may not represent sufficient homology to conclude that the compared sequences are related. Additional statistical analysis to determine the significance of such matches given the size of the data set can be carried out to determine the relevance of these sequences.

Exemplary parameters for determining relatedness of two or more sequences using the BLAST algorithm, for example, can be as set forth below. Briefly, amino acid sequence alignments can be performed using BLASTP version 2.0.8 (Jan. 5, 1999) and the following parameters: Matrix: 0 BLOSUM62; gap open: 11; gap extension: 1; x_dropoff: 50; expect: 10.0; wordsize: 3; filter: on. Nucleic acid sequence alignments can be performed using BLASTN version 2.0.6 (Sep. 16, 1998) and the following parameters: Match: 1; mismatch: −2; gap open: 5; gap extension: 2; x_dropoff: 50; expect: 10.0; wordsize: 11; filter: off. Those skilled in the art will know what modifications can be made to the above parameters to either increase or decrease the stringency of the comparison, for example, and determine the relatedness of two or more sequences.

In some embodiments, the invention provides a non-naturally occurring microbial organism, including a microbial organism having a butadiene pathway having at least one exogenous nucleic acid encoding a butadiene pathway enzyme expressed in a sufficient amount to produce butadiene, the butadiene pathway including an acetyl-CoA:acetyl-CoA acyltransferase, an acetoacetyl-CoA reductase, a 3-hydroxybutyryl-CoA dehydratase, a crotonyl-CoA reductase (aldehyde forming), a crotonaldehyde reductase (alcohol forming), a crotyl alcohol kinase, a 2-butenyl-4-phosphate kinase, a butadiene synthase, a crotonyl-CoA hydrolase, synthetase, or transferase, a crotonate reductase, a crotonyl-CoA reductase (alcohol forming), a glutaconyl-CoA decarboxylase, a glutaryl-CoA dehydrogenase, a 3-aminobutyryl-CoA deaminase, a 4-hydroxybutyryl-CoA dehydratase or a crotyl alcohol diphosphokinase (FIG. 2). In one aspect, the non-naturally occurring microbial organism includes a microbial organism having a butadiene pathway having at least one exogenous nucleic acid encoding butadiene pathway enzymes expressed in a sufficient amount to produce butadiene, the butadiene pathway including an acetyl-CoA:acetyl-CoA acyltransferase, an acetoacetyl-CoA reductase, a 3-hydroxybutyryl-CoA dehydratase, a crotonyl-CoA reductase (aldehyde forming), a crotonaldehyde reductase (alcohol forming), a crotyl alcohol kinase, a 2-butenyl-4-phosphate kinase and a butadiene synthase (FIG. 2, steps A-H). In one aspect, the non-naturally occurring microbial organism includes a microbial organism having a butadiene pathway having at least one exogenous nucleic acid encoding butadiene pathway enzymes expressed in a sufficient amount to produce butadiene, the butadiene pathway including an acetyl-CoA:acetyl-CoA acyltransferase, an acetoacetyl-CoA reductase, a 3-hydroxybutyryl-CoA dehydratase, a crotyl alcohol kinase, a 2-butenyl-4-phosphate kinase, a butadiene synthase and crotonyl-CoA reductase (alcohol forming) (FIG. 2, steps A-C, K, F, G, H). In one aspect, the non-naturally occurring microbial organism includes a microbial organism having a butadiene pathway having at least one exogenous nucleic acid encoding butadiene pathway enzymes expressed in a sufficient amount to produce butadiene, the butadiene pathway including an acetyl-CoA:acetyl-CoA acyltransferase, an acetoacetyl-CoA reductase, a 3-hydroxybutyryl-CoA dehydratase, a butadiene synthase, a crotonyl-CoA reductase (alcohol forming) and a crotyl alcohol diphosphokinase (FIG. 2, steps A-C, K, P, H). In one aspect, the non-naturally occurring microbial organism includes a microbial organism having a butadiene pathway having at least one exogenous nucleic acid encoding butadiene pathway enzymes expressed in a sufficient amount to produce butadiene, the butadiene pathway including an acetyl-CoA:acetyl-CoA acyltransferase, an acetoacetyl-CoA reductase, a 3-hydroxybutyryl-CoA dehydratase, a crotonaldehyde reductase (alcohol forming), a crotyl alcohol kinase, a 2-butenyl-4-phosphate kinase, a butadiene synthase, a crotonyl-CoA hydrolase, synthetase, or transferase and a crotonate reductase, (FIG. 2, steps A-C, I, J, E, F, G, H). In one aspect, the non-naturally occurring microbial organism includes a microbial organism having a butadiene pathway having at least one exogenous nucleic acid encoding butadiene pathway enzymes expressed in a sufficient amount to produce butadiene, the butadiene pathway including an acetyl-CoA:acetyl-CoA acyltransferase, an acetoacetyl-CoA reductase, a 3-hydroxybutyryl-CoA dehydratase, a crotonaldehyde reductase (alcohol forming), a butadiene synthase, a crotonyl-CoA hydrolase, synthetase or transferase, a crotonate reductase and a crotyl alcohol diphosphokinase (FIG. 2, steps A-C, I, J, E, P, H). In one aspect, the non-naturally occurring microbial organism includes a microbial organism having a butadiene pathway having at least one exogenous nucleic acid encoding butadiene pathway enzymes expressed in a sufficient amount to produce butadiene, the butadiene pathway including an acetyl-CoA:acetyl-CoA acyltransferase, an acetoacetyl-CoA reductase, a 3-hydroxybutyryl-CoA dehydratase, a crotonyl-CoA reductase (aldehyde forming), a crotonaldehyde reductase (alcohol forming), a butadiene synthase and a crotyl alcohol diphosphokinase (FIG. 2, steps A-E, P, H). In one aspect, the non-naturally occurring microbial organism includes a microbial organism having a butadiene pathway having at least one exogenous nucleic acid encoding butadiene pathway enzymes expressed in a sufficient amount to produce butadiene, the butadiene pathway including a glutaconyl-CoA decarboxylase, a crotonyl-CoA reductase (aldehyde forming), a crotonaldehyde reductase (alcohol forming), a crotyl alcohol kinase, a 2-butenyl-4-phosphate kinase and a butadiene synthase (FIG. 2, steps L, D-H). In one aspect, the non-naturally occurring microbial organism includes a microbial organism having a butadiene pathway having at least one exogenous nucleic acid encoding butadiene pathway enzymes expressed in a sufficient amount to produce butadiene, the butadiene pathway including a glutaconyl-CoA decarboxylase, a crotyl alcohol kinase, a 2-butenyl-4-phosphate kinase, a butadiene synthase and crotonyl-CoA reductase (alcohol forming) (FIG. 2, steps L, K, F, G, H). In one aspect, the non-naturally occurring microbial organism includes a microbial organism having a butadiene pathway having at least one exogenous nucleic acid encoding butadiene pathway enzymes expressed in a sufficient amount to produce butadiene, the butadiene pathway including a glutaconyl-CoA decarboxylase, a butadiene synthase, a crotonyl-CoA reductase (alcohol forming) and a crotyl alcohol diphosphokinase (FIG. 2, steps L, K, P, H). In one aspect, the non-naturally occurring microbial organism includes a microbial organism having a butadiene pathway having at least one exogenous nucleic acid encoding butadiene pathway enzymes expressed in a sufficient amount to produce butadiene, the butadiene pathway including a glutaconyl-CoA decarboxylase, a crotonaldehyde reductase (alcohol forming), a crotyl alcohol kinase, a 2-butenyl-4-phosphate kinase, a butadiene synthase, a crotonyl-CoA hydrolase, synthetase, or transferase and a crotonate reductase (FIG. 2, steps L, I, J, E, F, G, H). In one aspect, the non-naturally occurring microbial organism includes a microbial organism having a butadiene pathway having at least one exogenous nucleic acid encoding butadiene pathway enzymes expressed in a sufficient amount to produce butadiene, the butadiene pathway including a glutaconyl-CoA decarboxylase, a crotonaldehyde reductase (alcohol forming), a butadiene synthase, a crotonyl-CoA hydrolase, synthetase or transferase, a crotonate reductase and a crotyl alcohol diphosphokinase (FIG. 2, steps L, I, J, E, P, H). In one aspect, the non-naturally occurring microbial organism includes a microbial organism having a butadiene pathway having at least one exogenous nucleic acid encoding butadiene pathway enzymes expressed in a sufficient amount to produce butadiene, the butadiene pathway including a 3-hydroxybutyryl-CoA dehydratase, a crotonyl-CoA reductase (aldehyde forming), a crotonaldehyde reductase (alcohol forming), a butadiene a glutaconyl-CoA decarboxylase and a crotyl alcohol diphosphokinase (FIG. 2, steps L, C, D, E, P, H). In one aspect, the non-naturally occurring microbial organism includes a microbial organism having a butadiene pathway having at least one exogenous nucleic acid encoding butadiene pathway enzymes expressed in a sufficient amount to produce butadiene, the butadiene pathway including a glutaryl-CoA dehydrogenase, a crotonyl-CoA reductase (aldehyde forming), a crotonaldehyde reductase (alcohol forming), a crotyl alcohol kinase, a 2-butenyl-4-phosphate kinase and a butadiene synthase (FIG. 2, steps M, D-H). In one aspect, the non-naturally occurring microbial organism includes a microbial organism having a butadiene pathway having at least one exogenous nucleic acid encoding butadiene pathway enzymes expressed in a sufficient amount to produce butadiene, the butadiene pathway including a glutaryl-CoA dehydrogenase, a crotyl alcohol kinase, a 2-butenyl-4-phosphate kinase, a butadiene synthase and crotonyl-CoA reductase (alcohol forming) (FIG. 2, steps M, K, F, G, H). In one aspect, the non-naturally occurring microbial organism includes a microbial organism having a butadiene pathway having at least one exogenous nucleic acid encoding butadiene pathway enzymes expressed in a sufficient amount to produce butadiene, the butadiene pathway including a glutaryl-CoA dehydrogenase, a butadiene synthase, a crotonyl-CoA reductase (alcohol forming) and a crotyl alcohol diphosphokinase (FIG. 2, steps M, K, P, H). In one aspect, the non-naturally occurring microbial organism includes a microbial organism having a butadiene pathway having at least one exogenous nucleic acid encoding butadiene pathway enzymes expressed in a sufficient amount to produce butadiene, the butadiene pathway including a glutaryl-CoA dehydrogenase, a crotonaldehyde reductase (alcohol forming), a crotyl alcohol kinase, a 2-butenyl-4-phosphate kinase, a butadiene synthase, a crotonyl-CoA hydrolase, synthetase, or transferase and a crotonate reductase (FIG. 2, steps M, I, J, E, F, G, H). In one aspect, the non-naturally occurring microbial organism includes a microbial organism having a butadiene pathway having at least one exogenous nucleic acid encoding butadiene pathway enzymes expressed in a sufficient amount to produce butadiene, the butadiene pathway including a glutaryl-CoA dehydrogenase, a crotonaldehyde reductase (alcohol forming), a butadiene synthase, a crotonyl-CoA hydrolase, synthetase or transferase, a crotonate reductase and a crotyl alcohol diphosphokinase (FIG. 2, steps M, I, J, E, P, H). In one aspect, the non-naturally occurring microbial organism includes a microbial organism having a butadiene pathway having at least one exogenous nucleic acid encoding butadiene pathway enzymes expressed in a sufficient amount to produce butadiene, the butadiene pathway including a 3-hydroxybutyryl-CoA dehydratase, a crotonyl-CoA reductase (aldehyde forming), a crotonaldehyde reductase (alcohol forming), a butadiene synthase, a glutaryl-CoA dehydrogenase and a crotyl alcohol diphosphokinase (FIG. 2, steps M, C, D, E, P, H). In one aspect, the non-naturally occurring microbial organism includes a microbial organism having a butadiene pathway having at least one exogenous nucleic acid encoding butadiene pathway enzymes expressed in a sufficient amount to produce butadiene, the butadiene pathway including a 3-aminobutyryl-CoA deaminase, a crotonyl-CoA reductase (aldehyde forming), a crotonaldehyde reductase (alcohol forming), a crotyl alcohol kinase, a 2-butenyl-4-phosphate kinase and a butadiene synthase (FIG. 2, steps N, D-H). In one aspect, the non-naturally occurring microbial organism includes a microbial organism having a butadiene pathway having at least one exogenous nucleic acid encoding butadiene pathway enzymes expressed in a sufficient amount to produce butadiene, the butadiene pathway including a 3-aminobutyryl-CoA deaminase, a crotyl alcohol kinase, a 2-butenyl-4-phosphate kinase, a butadiene synthase and crotonyl-CoA reductase (alcohol forming) (FIG. 2, steps N, K, F, G, H). In one aspect, the non-naturally occurring microbial organism includes a microbial organism having a butadiene pathway having at least one exogenous nucleic acid encoding butadiene pathway enzymes expressed in a sufficient amount to produce butadiene, the butadiene pathway including a 3-aminobutyryl-CoA deaminase, a butadiene synthase, a crotonyl-CoA reductase (alcohol forming) and a crotyl alcohol diphosphokinase (FIG. 2, steps N, K, P, H). In one aspect, the non-naturally occurring microbial organism includes a microbial organism having a butadiene pathway having at least one exogenous nucleic acid encoding butadiene pathway enzymes expressed in a sufficient amount to produce butadiene, the butadiene pathway including a 3-aminobutyryl-CoA deaminase, a crotonaldehyde reductase (alcohol forming), a crotyl alcohol kinase, a 2-butenyl-4-phosphate kinase, a butadiene synthase, a crotonyl-CoA hydrolase, synthetase, or transferase and a crotonate reductase (FIG. 2, steps N, I, J, E, F, G, H). In one aspect, the non-naturally occurring microbial organism includes a microbial organism having a butadiene pathway having at least one exogenous nucleic acid encoding butadiene pathway enzymes expressed in a sufficient amount to produce butadiene, the butadiene pathway including a 3-aminobutyryl-CoA deaminase, a crotonaldehyde reductase (alcohol forming), a butadiene synthase, a crotonyl-CoA hydrolase, synthetase or transferase, a crotonate reductase and a crotyl alcohol diphosphokinase (FIG. 2, steps N, I, J, E, P, H). In one aspect, the non-naturally occurring microbial organism includes a microbial organism having a butadiene pathway having at least one exogenous nucleic acid encoding butadiene pathway enzymes expressed in a sufficient amount to produce butadiene, the butadiene pathway including a 3-hydroxybutyryl-CoA dehydratase, a crotonyl-CoA reductase (aldehyde forming), a crotonaldehyde reductase (alcohol forming), a butadiene synthase, a 3-aminobutyryl-CoA deaminase and a crotyl alcohol diphosphokinase (FIG. 2, steps N, C, D, E, P, H). In one aspect, the non-naturally occurring microbial organism includes a microbial organism having a butadiene pathway having at least one exogenous nucleic acid encoding butadiene pathway enzymes expressed in a sufficient amount to produce butadiene, the butadiene pathway including a 4-hydroxybutyryl-CoA dehydratase, a crotonyl-CoA reductase (aldehyde forming), a crotonaldehyde reductase (alcohol forming), a crotyl alcohol kinase, a 2-butenyl-4-phosphate kinase and a butadiene synthase (FIG. 2, steps O, D-H). In one aspect, the non-naturally occurring microbial organism includes a microbial organism having a butadiene pathway having at least one exogenous nucleic acid encoding butadiene pathway enzymes expressed in a sufficient amount to produce butadiene, the butadiene pathway including a 4-hydroxybutyryl-CoA dehydratase, a crotyl alcohol kinase, a 2-butenyl-4-phosphate kinase, a butadiene synthase and crotonyl-CoA reductase (alcohol forming) (FIG. 2, steps O, K, F, G, H). In one aspect, the non-naturally occurring microbial organism includes a microbial organism having a butadiene pathway having at least one exogenous nucleic acid encoding butadiene pathway enzymes expressed in a sufficient amount to produce butadiene, the butadiene pathway including a 4-hydroxybutyryl-CoA dehydratase, a butadiene synthase, a crotonyl-CoA reductase (alcohol forming) and a crotyl alcohol diphosphokinase (FIG. 2, steps O, K, P, H). In one aspect, the non-naturally occurring microbial organism includes a microbial organism having a butadiene pathway having at least one exogenous nucleic acid encoding butadiene pathway enzymes expressed in a sufficient amount to produce butadiene, the butadiene pathway including a 4-hydroxybutyryl-CoA dehydratase, a crotonaldehyde reductase (alcohol forming), a crotyl alcohol kinase, a 2-butenyl-4-phosphate kinase, a butadiene synthase, a crotonyl-CoA hydrolase, synthetase, or transferase and a crotonate reductase (FIG. 2, steps O, I, J, E, F, G, H). In one aspect, the non-naturally occurring microbial organism includes a microbial organism having a butadiene pathway having at least one exogenous nucleic acid encoding butadiene pathway enzymes expressed in a sufficient amount to produce butadiene, the butadiene pathway including a 4-hydroxybutyryl-CoA dehydratase, a crotonaldehyde reductase (alcohol forming), a butadiene synthase, a crotonyl-CoA hydrolase, synthetase or transferase, a crotonate reductase and a crotyl alcohol diphosphokinase (FIG. 2, steps O, I, J, E, P, H). In one aspect, the non-naturally occurring microbial organism includes a microbial organism having a butadiene pathway having at least one exogenous nucleic acid encoding butadiene pathway enzymes expressed in a sufficient amount to produce butadiene, the butadiene pathway including a 3-hydroxybutyryl-CoA dehydratase, a crotonyl-CoA reductase (aldehyde forming), a crotonaldehyde reductase (alcohol forming), a butadiene synthase, a 4-hydroxybutyryl-CoA dehydratase and a crotyl alcohol diphosphokinase (FIG. 2, steps L, C, D, E, P, H).

In some embodiments, the invention provides a non-naturally occurring microbial organism comprising a crotyl alcohol pathway. The crotyl alcohol pathway includes at least one exogenous nucleic acid encoding a crotyl alcohol pathway enzyme expressed in a sufficient amount to produce crotyl alcohol. The crotyl alcohol pathway includes an acetyl-CoA:acetyl-CoA acyltransferase, an acetoacetyl-CoA reductase, a 3-hydroxybutyryl-CoA dehydratase, a crotonyl-CoA reductase (aldehyde forming), a crotonaldehyde reductase (alcohol forming), a crotonyl-CoA hydrolase, synthetase, or transferase, a crotonate reductase, a crotonyl-CoA reductase (alcohol forming), a glutaconyl-CoA decarboxylase, a glutaryl-CoA dehydrogenase, a 3-aminobutyryl-CoA deaminase, or a 4-hydroxybutyryl-CoA dehydratase.

In some embodiments, the microbial organism comprises two exogenous nucleic acids each encoding a crotyl alcohol pathway enzyme, in other embodiments, the microbial organism includes three exogenous nucleic acids each encoding a crotyl alcohol pathway enzyme, in still further embodiments the microbial organism includes four exogenous nucleic acids each encoding a crotyl alcohol pathway enzyme.

In some embodiments, the crotyl alcohol pathway includes an acetyl-CoA:acetyl-CoA acyltransferase, an acetoacetyl-CoA reductase, a 3-hydroxybutyryl-CoA dehydratase, a crotonyl-CoA reductase (aldehyde forming), and a crotonaldehyde reductase (alcohol forming). In some embodiments, the crotyl alcohol pathway includes an acetyl-CoA:acetyl-CoA acyltransferase, an acetoacetyl-CoA reductase, a 3-hydroxybutyryl-CoA dehydratase, and a crotonyl-CoA reductase (alcohol forming). In some embodiments, the crotyl alcohol pathway includes an acetyl-CoA:acetyl-CoA acyltransferase, an acetoacetyl-CoA reductase, a 3-hydroxybutyryl-CoA dehydratase, a crotonaldehyde reductase (alcohol forming), a crotonyl-CoA hydrolase, synthetase or transferase and a crotonate reductase. In some embodiments, the crotyl alcohol pathway includes a glutaconyl-CoA decarboxylase, a crotonyl-CoA reductase (aldehyde forming), and a crotonaldehyde reductase (alcohol forming). In some embodiments, the crotyl alcohol pathway includes a glutaconyl-CoA decarboxylase and crotonyl-CoA reductase (alcohol forming). In some embodiments, the crotyl alcohol pathway includes a glutaconyl-CoA decarboxylase, a crotonaldehyde reductase (alcohol forming), a crotonyl-CoA hydrolase, synthetase, or transferase and a crotonate reductase. In some embodiments, the crotyl alcohol pathway includes a glutaryl-CoA dehydrogenase, a crotonyl-CoA reductase (aldehyde forming), and a crotonaldehyde reductase (alcohol forming). In some embodiments, the crotyl alcohol pathway includes a glutaryl-CoA dehydrogenase and crotonyl-CoA reductase (alcohol forming). In some embodiments, the crotyl alcohol pathway includes a glutaryl-CoA dehydrogenase, a crotonaldehyde reductase (alcohol forming), a crotonyl-CoA hydrolase, synthetase, or transferase and a crotonate reductase. In some embodiments, the crotyl alcohol pathway includes a 3-aminobutyryl-CoA deaminase, a crotonyl-CoA reductase (aldehyde forming), and a crotonaldehyde reductase (alcohol forming). In some embodiments, the crotyl alcohol pathway includes a 3-aminobutyryl-CoA deaminase and crotonyl-CoA reductase (alcohol forming). In some embodiments, the crotyl alcohol pathway includes a 3-aminobutyryl-CoA deaminase, a crotonaldehyde reductase (alcohol forming), a crotonyl-CoA hydrolase, synthetase or transferase and a crotonate reductase. In some embodiments, the crotyl alcohol pathway includes a 4-hydroxybutyryl-CoA dehydratase, a crotonyl-CoA reductase (aldehyde forming), and a crotonaldehyde reductase (alcohol forming). In some embodiments, the crotyl alcohol pathway includes a 4-hydroxybutyryl-CoA dehydratase and crotonyl-CoA reductase (alcohol forming). In some embodiments, the crotyl alcohol pathway includes a 4-hydroxybutyryl-CoA dehydratase, a crotonaldehyde reductase (alcohol forming), a crotonyl-CoA hydrolase, synthetase or transferase and a crotonate reductase. In some embodiments, the non-naturally occurring microbial organism having a crotyl alcohol pathway has at least one exogenous nucleic acid that is a heterologous nucleic acid. In some embodiments, the non-naturally occurring microbial organism having a crotyl alcohol pathway is in a substantially anaerobic culture medium.

In some embodiments, the invention provides a non-naturally occurring microbial organism, including a microbial organism having a butadiene pathway having at least one exogenous nucleic acid encoding a butadiene pathway enzyme expressed in a sufficient amount to produce butadiene, the butadiene pathway including an erythrose-4-phosphate reductase, an erythritol-4-phospate cytidylyltransferase, a 4-(cytidine 5'-diphospho)-erythritol kinase, an erythritol 2,4-cyclodiphosphate synthase, a 1-hydroxy-2-butenyl 4-diphosphate synthase, a 1-hydroxy-2-butenyl 4-diphosphate reductase, a butenyl 4-diphosphate isomerase, a butadiene synthase, an erythrose-4-phosphate kinase, an erythrose reductase or an erythritol kinase (FIG. 3). In one aspect, the non-naturally occurring microbial organism includes a microbial organism having a butadiene pathway having at least one exogenous nucleic acid encoding butadiene pathway enzymes expressed in a sufficient amount to produce butadiene, the butadiene pathway including an erythrose-4-phosphate reductase, an erythritol-4-phospate cytidylyltransferase, a 4-(cytidine 5'-diphospho)-erythritol kinase, an erythritol 2,4-cyclodiphosphate synthase, a 1-hydroxy-2-butenyl 4-diphosphate synthase, a 1-hydroxy-2-butenyl 4-diphosphate reductase and a butadiene synthase (FIG. 3, steps A-F, and H). In one aspect, the non-naturally occurring microbial organism includes a microbial organism having a butadiene pathway having at least one exogenous nucleic acid encoding butadiene pathway enzymes expressed in a sufficient amount to produce butadiene, the butadiene pathway including an erythrose-4-phosphate reductase, an erythritol-4-phospate cytidylyltransferase, a 4-(cytidine 5'-diphospho)-erythritol kinase, an erythritol 2,4-cyclodiphosphate synthase, a 1-hydroxy-2-butenyl 4-diphosphate synthase, a 1-hydroxy-2-butenyl 4-diphosphate reductase, a butenyl 4-diphosphate isomerase and butadiene synthase (FIG. 3, steps A-H). In one aspect, the non-naturally occurring microbial organism includes a microbial organism having a butadiene pathway having at least one exogenous nucleic acid encoding butadiene pathway enzymes expressed in a sufficient amount to produce butadiene, the butadiene pathway including an erythritol-4-phospate cytidylyltransferase, a 4-(cytidine 5'-diphospho)-erythritol kinase, an erythritol 2,4-cyclodiphosphate synthase, a 1-hydroxy-2-butenyl 4-diphosphate synthase, a 1-hydroxy-2-butenyl 4-diphosphate reductase, a butadiene synthase, an erythrose-4-phosphate kinase, an erythrose reductase and a erythritol kinase (FIG. 3, steps I, J, K, B-F, H). In one aspect, the non-naturally occurring microbial organism includes a microbial organism having a butadiene pathway having at least one exogenous nucleic acid encoding butadiene pathway enzymes expressed in a sufficient amount to produce butadiene, the butadiene pathway including an erythritol-4-phospate cytidylyltransferase, a 4-(cytidine 5'-diphospho)-erythritol kinase, an erythritol 2,4-cyclodiphosphate synthase, a 1-hydroxy-2-butenyl 4-diphosphate synthase, a 1-hydroxy-2-butenyl 4-diphosphate reductase, a butenyl 4-diphosphate isomerase, a butadiene synthase, an erythrose-4-phosphate kinase, an erythrose reductase and an erythritol kinase (FIG. 3, steps I, J, K, B-H).

In some embodiments, the invention provides a non-naturally occurring microbial organism, including a microbial organism having a butadiene pathway having at least one exogenous nucleic acid encoding a butadiene pathway enzyme expressed in a sufficient amount to produce butadiene, the butadiene pathway including a malonyl-CoA:acetyl-CoA acyltransferase, a 3-oxoglutaryl-CoA reductase (ketone-reducing), a 3-hydroxyglutaryl-CoA reductase (aldehyde forming), a 3-hydroxy-5-oxopentanoate reductase, a 3,5-dihydroxypentanoate kinase, a 3-hydroxy-5-phosphonatooxypentanoate kinase, a 3-hydroxy-5-[hydroxy(phosphonooxy)phosphoryl]oxy pentanoate decarboxylase, a butenyl 4-diphosphate isomerase, a butadiene synthase, a 3-hydroxyglutaryl-CoA reductase (alcohol forming), a 3-oxoglutaryl-CoA reductase (aldehyde forming), a 3,5-dioxopentanoate reductase (ketone reducing), a 3,5-dioxopentanoate reductase (aldehyde reducing), a 5-hydroxy-3-oxopentanoate reductase or a 3-oxo-glutaryl-CoA reductase (CoA reducing and alcohol forming) (FIG. 4). In one aspect, the non-naturally occurring microbial organism includes a microbial organism having a butadiene pathway having at least one exogenous nucleic acid encoding butadiene pathway enzymes expressed in a sufficient amount to produce butadiene, the butadiene pathway including a malonyl-CoA:acetyl-CoA acyltransferase, a 3-oxoglutaryl-CoA reductase (ketone-reducing), a 3-hydroxyglutaryl-CoA reductase (aldehyde forming), a 3-hydroxy-5-oxopentanoate reductase, a 3,5-dihydroxypentanoate kinase, a 3-hydroxy-5-phosphonatooxypentanoate kinase, a 3-hydroxy-5-[hydroxy(phosphonooxy)phosphoryl]oxy pentanoate decarboxylase, a butenyl 4-diphosphate isomerase and a butadiene synthase (FIG. 4, steps A-I). In one aspect, the non-naturally occurring microbial organism includes a microbial organism having a butadiene pathway having at least one exogenous nucleic acid encoding butadiene pathway enzymes expressed in a sufficient amount to produce butadiene, the butadiene pathway including a malonyl-CoA:acetyl-CoA acyltransferase, a 3,5-dihydroxypentanoate kinase, a 3-hydroxy-5-phosphonatooxypentanoate kinase, a 3-hydroxy-5-[hydroxy(phosphonooxy)phosphoryl]oxy pentanoate decarboxylase, a butenyl 4-diphosphate isomerase, a butadiene synthase, a 3-oxoglutaryl-CoA reductase (aldehyde forming), a 3,5-dioxopentanoate reductase (aldehyde reducing) and a 5-hydroxy-3-oxopentanoate reductase. (FIG. 4, steps A, K, M, N, E, F, G, H, I). In one aspect, the non-naturally occurring microbial organism includes a microbial organism having a butadiene pathway having at least one exogenous nucleic acid encoding butadiene pathway enzymes expressed in a sufficient amount to produce butadiene, the butadiene pathway including a malonyl-CoA:acetyl-CoA acyltransferase, a 3-hydroxy-5-oxopentanoate reductase, a 3,5-dihydroxypentanoate kinase, a 3-Hydroxy-5-phosphonatooxypentanoate kinase, a 3-Hydroxy-5-[hydroxy(phosphonooxy)phosphoryl]oxy pentanoate decarboxylase, a butenyl 4-diphosphate isomerase, a butadiene synthase, a 3-oxoglutaryl-CoA reductase (aldehyde forming) and a 3,5-dioxopentanoate reductase (ketone reducing). (FIG. 4, steps A, K, L, D, E, F, G, H, I). In one aspect, the non-naturally occurring microbial organism includes a microbial organism having a butadiene pathway having at least one exogenous nucleic acid encoding butadiene pathway enzymes expressed in a sufficient amount to produce butadiene, the butadiene pathway including a malonyl-CoA:acetyl-CoA acyltransferase, a 3,5-dihydroxypentanoate kinase, a 3-hydroxy-5-phosphonatooxypentanoate kinase, a 3-hydroxy-5-[hydroxy(phosphonooxy)phosphoryl] oxy pentanoate decarboxylase, a butenyl 4-diphosphate isomerase, a butadiene synthase, a 5-hydroxy-3-oxopentanoate reductase and a 3-oxo-glutaryl-CoA reductase (CoA reducing and alcohol forming). (FIG. 4, steps A, O, N, E, F, G, H, I). In one aspect, the non-naturally occurring microbial organism includes a microbial organism having a butadiene pathway having at least one exogenous nucleic acid encoding butadiene pathway enzymes expressed in a sufficient amount to produce butadiene, the butadiene pathway including a malonyl-CoA:acetyl-CoA acyltransferase, a 3-oxoglutaryl-CoA reductase (ketone-reducing), a 3,5-dihydroxypentanoate kinase, a 3-hydroxy-5-phosphonatooxypentanoate kinase, a 3-hydroxy-5-[hydroxy(phosphonooxy)phosphoryl] oxy pentanoate decarboxylase, a butenyl 4-diphosphate isomerase, a butadiene synthase and a 3-hydroxyglutaryl-CoA reductase (alcohol forming). (FIG. 4, steps A, B, J, E, F, G, H, I).

In an additional embodiment, the invention provides a non-naturally occurring microbial organism having a butadiene pathway, wherein the non-naturally occurring microbial organism comprises at least one exogenous nucleic acid encoding an enzyme or protein that converts a substrate to a product selected from the group consisting of acetyl-CoA to acetoacetyl-CoA, acetoacetyl-CoA to 3-hydroxybutyryl-CoA, 3-hydroxybutyryl-CoA to crotonyl-CoA, crotonyl-CoA to crotonaldehyde, crotonaldehyde to crotyl alcohol, crotyl alcohol to 2-betenyl-phosphate, 2-betenyl-phosphate to 2-butenyl-4-diphosphate, 2-butenyl-4-diphosphate to butadiene, erythrose-4-phosphate to erythritol-4-phosphate, erythritol-4-phosphate to 4-(cytidine 5'-diphospho)-erythritol, 4-(cytidine 5'-diphospho)-erythritol to 2-phospho-4-(cytidine 5'-diphospho)-erythritol, 2-phospho-4-(cytidine 5'-diphospho)-erythritol to erythritol-2,4-cyclodiphosphate, erythritol-2,4-cyclodiphosphate to 1-hydroxy-2-butenyl 4-diphosphate, 1-hydroxy-2-butenyl 4-diphosphate to butenyl 4-diphosphate, butenyl 4-diphosphate to 2-butenyl 4-diphosphate, 1-hydroxy-2-butenyl 4-diphosphate to 2-butenyl 4-diphosphate, 2-butenyl 4-diphosphate to butadiene, malonyl-CoA and acetyl-CoA to 3-oxoglutaryl-CoA, 3-oxoglutaryl-CoA to 3-hydroxyglutaryl-CoA to 3-hydroxy-5-oxopentanoate, 3-hydroxy-5-oxopentanoate to 3,5-dihydroxy pentanoate, 3,5-dihydroxy pentanoate to 3-hydroxy-5-phosphonatooxypentanoate, 3-hydroxy-5-phosphonatooxypentanoate to 3-hydroxy-5-[hydroxy(phosphonooxy)phosphoryl]oxy pentanoate, 3-hydroxy-5-[hydroxy(phosphonooxy)phosphoryl]oxy pentanoate to butenyl 4-biphosphate, glutaconyl-CoA to crotonyl-CoA, glutaryl-CoA to crotonyl-CoA, 3-aminobutyryl-CoA to crotonyl-CoA, 4-hydroxybutyryl-CoA to crotonyl-CoA, crotonyl-CoA to crotonate, crotonate to crotonaldehyde, crotonyl-CoA to crotyl alcohol, crotyl alcohol to 2-butenyl-4-diphosphate, erythrose-4-phosphate to erythrose, erythrose to erythritol, erythritol to erythritol-4-phosphate, 3-oxoglutaryl-CoA to 3,5-dioxopentanoate, 3,5-dioxopentanoate to 5-hydroxy-3-oxopentanoate, 5-hydroxy-3-oxopentanoate to 3,5-dihydroxypentanoate, 3-oxoglutaryl-CoA to 5-hydroxy-3-oxopentanoate, 3,5-dioxopentanoate to 3-hydroxy-5-oxopentanoate and 3-hydroxyglutaryl-CoA to 3,5-dihydroxypentanoate. One skilled in the art will understand that these are merely exemplary and that any of the substrate-product pairs disclosed herein suitable to produce a desired product and for which an appropriate activity is available for the conversion of the substrate to the product can be readily determined by one skilled in the art based on the teachings herein. Thus, the invention provides a non-naturally occurring microbial organism containing at least one exogenous nucleic acid encoding an enzyme or protein, where the enzyme or protein converts the substrates and products of a butadiene pathway, such as that shown in FIGS. 2-4.

While generally described herein as a microbial organism that contains a butadiene pathway, it is understood that the invention additionally provides a non-naturally occurring microbial organism comprising at least one exogenous nucleic acid encoding a butadiene pathway enzyme expressed in a sufficient amount to produce an intermediate of a butadiene pathway. For example, as disclosed herein, a butadiene pathway is exemplified in FIGS. 2-4. Therefore, in addition to a microbial organism containing a butadiene pathway that produces butadiene, the invention additionally provides a non-naturally occurring microbial organism comprising at least one exogenous nucleic acid encoding a butadiene pathway enzyme, where the microbial organism produces a butadiene pathway intermediate, for example, acetoacetyl-CoA, 3-hydroxybutyryl-CoA, crotonyl-CoA, crotonaldehyde, crotyl alcohol, 2-betenyl-phosphate, 2-butenyl-4-diphosphate, erythritol-4-phosphate, 4-(cytidine 5'-diphospho)-erythritol, 2-phospho-4-(cytidine 5'-diphospho)-erythritol, erythritol-2,4-cyclodiphosphate, 1-hydroxy-2-butenyl 4-diphosphate, butenyl 4-diphosphate, 2-butenyl 4-diphosphate, 3-oxoglutaryl-CoA, 3-hydroxyglutaryl-CoA, 3-hydroxy-5-oxopentanoate, 3,5-dihydroxy pentanoate, 3-hydroxy-5-phosphonatooxypentanoate, 3-hydroxy-5-[hydroxy(phosphonooxy) phosphoryl]oxy pentanoate, crotonate, erythrose, erythritol, 3,5-dioxopentanoate or 5-hydroxy-3-oxopentanoate.

It is understood that any of the pathways disclosed herein, as described in the Examples and exemplified in the Figures, including the pathways of FIGS. 2-4, can be utilized to generate a non-naturally occurring microbial organism that produces any pathway intermediate or product, as desired. As disclosed herein, such a microbial organism that produces an intermediate can be used in combination with another microbial organism expressing downstream pathway enzymes to produce a desired product. However, it is understood that a non-naturally occurring microbial organism that produces a butadiene pathway intermediate can be utilized to produce the intermediate as a desired product.

In some embodiments, access to butadiene can be accomplished by biosynthetic production of crotyl alcohol and subsequent chemical dehydration to butadiene. In some embodiments, the invention provides a process for the production of butadiene that includes (a) culturing by fermentation in a sufficient amount of nutrients and media a non-naturally occurring microbial organism that produces crotyl alcohol; and (b) converting crotyl alcohol produced by culturing the non-naturally occurring microbial organism to butadiene.

The dehydration of alcohols are known in the art and can include various thermal processes, both catalyzed and non-catalyzed. In some embodiments, a catalyzed thermal dehydration employs a metal oxide catalyst or silica. In some embodiments, step (b) of the process is performed by chemical dehydration in the presence of a catalyst. For example, it has been indicated that crotyl alcohol can be dehydrated over bismuth molybdate (Adams, C. R. *J. Catal.* 10:355-361, 1968) to afford 1,3-butadiene.

Dehydration can be achieved via activation of the alcohol group and subsequent elimination by standard elimination mechanisms such as E1 or E2 elimination. Activation can be achieved by way of conversion of the alcohol group to a halogen such as iodide, chloride, or bromide. Activation can also be accomplished by way of a sulfonyl, phosphate or other activating functionality that convert the alcohol into a good leaving group. In some embodiments, the activating group is a sulfate or sulfate ester selected from a tosylate, a mesylate, a nosylate, a brosylate, and a triflate. In some embodiments, the leaving group is a phosphate or phosphate ester. In some such embodiments, the dehydrating agent is phosphorus pentoxide.

In some embodiments, processes of the invention that rely on bioproduction of crotyl alcohol utilize non-naturally occurring microbial organism that include a crotyl alcohol pathway having at least one exogenous nucleic acid encoding a crotyl alcohol pathway enzyme expressed in a sufficient amount to produce crotyl alcohol. The crotyl alcohol pathway includes an acetyl-CoA:acetyl-CoA acyltransferase, an acetoacetyl-CoA reductase, a 3-hydroxybutyryl-CoA dehydratase, a crotonyl-CoA reductase (aldehyde forming), a crotonaldehyde reductase (alcohol forming), a crotonyl-CoA hydrolase, synthetase, or transferase, a crotonate reductase, a crotonyl-CoA reductase (alcohol forming), a glutaconyl-CoA decarboxylase, a glutaryl-CoA dehydrogenase, a 3-aminobutyryl-CoA deaminase, or a 4-hydroxybutyryl-CoA dehydratase.

In some embodiments, processes of the invention that rely on bioproduction of crotyl alcohol utilize a microbial organism that includes two exogenous nucleic acids each encoding a crotyl alcohol pathway enzyme. In some embodiments, processes of the invention that rely on bioproduction of crotyl alcohol utilize a microbial organism that includes three exogenous nucleic acids each encoding a crotyl alcohol pathway enzyme. In some embodiments, processes of the invention that rely on bioproduction of crotyl alcohol utilize a microbial organism that includes four exogenous nucleic acids each encoding a crotyl alcohol pathway enzyme.

In some embodiments, processes of the invention that rely on bioproduction of crotyl alcohol utilize a microbial organism having a crotyl alcohol pathway that includes an acetyl-CoA:acetyl-CoA acyltransferase, an acetoacetyl-CoA reductase, a 3-hydroxybutyryl-CoA dehydratase, a crotonyl-CoA reductase (aldehyde forming), and a crotonaldehyde reductase (alcohol forming). In some embodiments, processes of the invention that rely on bioproduction of crotyl alcohol utilize a microbial organism having a crotyl alcohol pathway that includes an acetyl-CoA:acetyl-CoA acyltransferase, an acetoacetyl-CoA reductase, a 3-hydroxybutyryl-CoA dehydratase, and a crotonyl-CoA reductase (alcohol forming). In some embodiments, processes of the invention that rely on bioproduction of crotyl alcohol utilize a microbial organism having a crotyl alcohol pathway that includes an acetyl-CoA: acetyl-CoA acyltransferase, an acetoacetyl-CoA reductase, a 3-hydroxybutyryl-CoA dehydratase, a crotonaldehyde reductase (alcohol forming), a crotonyl-CoA hydrolase, synthetase or transferase and a crotonate reductase.

In some embodiments, processes of the invention that rely on bioproduction of crotyl alcohol utilize a microbial organism having a crotyl alcohol pathway that includes a glutaconyl-CoA decarboxylase, a crotonyl-CoA reductase (aldehyde forming), and a crotonaldehyde reductase (alcohol forming). In some embodiments, processes of the invention that rely on bioproduction of crotyl alcohol utilize a microbial organism having a crotyl alcohol pathway that includes a glutaconyl-CoA decarboxylase and crotonyl-CoA reductase (alcohol forming). In some embodiments, processes of the invention that rely on bioproduction of crotyl alcohol utilize a microbial organism having a crotyl alcohol pathway that includes a glutaconyl-CoA decarboxylase, a crotonaldehyde reductase (alcohol forming), a crotonyl-CoA hydrolase, synthetase, or transferase and a crotonate reductase. In some embodiments, processes of the invention that rely on bioproduction of crotyl alcohol utilize a microbial organism having a crotyl alcohol pathway that includes a 3-hydroxybutyryl-CoA dehydratase, a crotonyl-CoA reductase (aldehyde forming), a crotonaldehyde reductase (alcohol forming), and a glutaconyl-CoA decarboxylase.

In some embodiments, processes of the invention that rely on bioproduction of crotyl alcohol utilize a microbial organism having a crotyl alcohol pathway that includes a glutaryl-CoA dehydrogenase, a crotonyl-CoA reductase (aldehyde forming), and a crotonaldehyde reductase (alcohol forming). In some embodiments, processes of the invention that rely on bioproduction of crotyl alcohol utilize a microbial organism having a crotyl alcohol pathway that includes a glutaryl-CoA dehydrogenase and crotonyl-CoA reductase (alcohol forming). In some embodiments, processes of the invention that rely on bioproduction of crotyl alcohol utilize a microbial organism having a crotyl alcohol pathway that includes a glutaryl-CoA dehydrogenase, a crotonaldehyde reductase (alcohol forming), a crotonyl-CoA hydrolase, synthetase, or transferase and a crotonate reductase. In some embodiments, processes of the invention that rely on bioproduction of crotyl alcohol utilize a microbial organism having a crotyl alcohol pathway that includes a 3-hydroxybutyryl-CoA dehydratase, a crotonyl-CoA reductase (aldehyde forming), a crotonaldehyde reductase (alcohol forming), and a glutaryl-CoA dehydrogenase.

In some embodiments, processes of the invention that rely on bioproduction of crotyl alcohol utilize a microbial organism having a crotyl alcohol pathway that includes a 3-aminobutyryl-CoA deaminase, a crotonyl-CoA reductase (aldehyde forming), and a crotonaldehyde reductase (alcohol forming). In some embodiments, processes of the invention that rely on bioproduction of crotyl alcohol utilize a microbial organism having a crotyl alcohol pathway that includes a 3-aminobutyryl-CoA deaminase and crotonyl-CoA reductase (alcohol forming). In some embodiments, processes of the invention that rely on bioproduction of crotyl alcohol utilize a microbial organism having a crotyl alcohol pathway that includes a 3-aminobutyryl-CoA deaminase, a crotonaldehyde reductase (alcohol forming), a crotonyl-CoA hydrolase, synthetase or transferase and a crotonate reductase. In some embodiments, processes of the invention that rely on bioproduction of crotyl alcohol utilize a microbial organism having a crotyl alcohol pathway that includes a 3-hydroxybutyryl-CoA dehydratase, a crotonyl-CoA reductase (aldehyde forming), a crotonaldehyde reductase (alcohol forming), and a 3-aminobutyryl-CoA deaminase.

In some embodiments, processes of the invention that rely on bioproduction of crotyl alcohol utilize a microbial organism having a crotyl alcohol pathway that includes a 4-hydroxybutyryl-CoA dehydratase, a crotonyl-CoA reductase (aldehyde forming), and a crotonaldehyde reductase (alcohol forming). In some embodiments, processes of the invention that rely on bioproduction of crotyl alcohol utilize a microbial organism having a crotyl alcohol pathway that includes a 4-hydroxybutyryl-CoA dehydratase and crotonyl-CoA reductase (alcohol forming). In some embodiments, processes of the invention that rely on bioproduction of crotyl alcohol utilize a microbial organism having a crotyl alcohol pathway that includes a 4-hydroxybutyryl-CoA dehydratase, a crotonaldehyde reductase (alcohol forming), a crotonyl-CoA hydrolase, synthetase or transferase and a crotonate reductase. In some embodiments, processes of the invention that rely on bioproduction of crotyl alcohol utilize a microbial organism having a crotyl alcohol pathway that includes a 3-hydroxybutyryl-CoA dehydratase, a crotonyl-CoA reductase (aldehyde forming), a crotonaldehyde reductase (alcohol forming), and a 4-hydroxybutyryl-CoA dehydratase.

In some embodiments, processes of the invention that rely on bioproduction of crotyl alcohol utilize a microbial organism having at least one exogenous nucleic acid is a heterologous nucleic acid. In some embodiments, processes of the invention that rely on bioproduction of crotyl alcohol utilize a non-naturally occurring microbial organism is in a substantially anaerobic culture medium.

Given the teachings and guidance provided herein, those skilled in the art will understand that other biosynthetic intermediates in a butadiene pathway can be targeted in further chemoenzymatic routes to 1,3-butadiene. For example, it has been indicated that crotonaldehyde is converted to 1,3-butadiene in the presence of ethanol over a silica catalyst (Toussaint et al., *Ind. Eng. Chem.*, 39(2):120-125, (1947)). In some embodiments, a process for the production of 1,3-butadiene includes a) culturing by fermentation in a sufficient amount of nutrients and media a non-naturally occurring microbial organism that produces crotonaldehyde; and (b) converting crotonaldehyde produced by culturing the non-naturally occurring microbial organism to butadiene. In some such chemoenzymatic processes of the invention, crotonaldehyde and ethanol can both be provided as fermentation products from a single non-naturally occurring organism, or from two separate organisms. The two fermentation products can be converted to 1,3-butadiene as described above using silica catalyst.

The invention is described herein with general reference to the metabolic reaction, reactant or product thereof, or with specific reference to one or more nucleic acids or genes encoding an enzyme associated with or catalyzing, or a protein associated with, the referenced metabolic reaction, reactant or product. Unless otherwise expressly stated herein, those skilled in the art will understand that reference to a reaction also constitutes reference to the reactants and products of the reaction. Similarly, unless otherwise expressly stated herein, reference to a reactant or product also references the reaction, and reference to any of these metabolic constituents also references the gene or genes encoding the enzymes that catalyze or proteins involved in the referenced reaction, reactant or product. Likewise, given the well known fields of metabolic biochemistry, enzymology and genomics, reference herein to a gene or encoding nucleic acid also constitutes a reference to the corresponding encoded enzyme and the reaction it catalyzes or a protein associated with the reaction as well as the reactants and products of the reaction.

As disclosed herein, the intermediate crotanate; 3,5-dioxopentanoate, 5-hydroxy-3-oxopentanoate, 3-hydroxy-5-oxopentanoate, 3-oxoglutaryl-CoA and 3-hydroxyglutaryl-CoA, as well as other intermediates, are carboxylic acids, which can occur in various ionized forms, including fully protonated, partially protonated, and fully deprotonated forms. Accordingly, the suffix "-ate," or the acid form, can be used interchangeably to describe both the free acid form as well as any deprotonated form, in particular since the ionized form is known to depend on the pH in which the compound is found.

It is understood that carboxylate products or intermediates includes ester forms of carboxylate products or pathway intermediates, such as O-carboxylate and S-carboxylate esters. O- and S-carboxylates can include lower alkyl, that is C1 to C6, branched or straight chain carboxylates. Some such O- or S-carboxylates include, without limitation, methyl, ethyl, n-propyl, n-butyl, i-propyl, sec-butyl, and tert-butyl, pentyl, hexyl O- or S-carboxylates, any of which can further possess an unsaturation, providing for example, propenyl, butenyl, pentyl, and hexenyl O- or S-carboxylates. O-carboxylates can be the product of a biosynthetic pathway. Exemplary O-carboxylates accessed via biosynthetic pathways can include, without limitation: methyl crotanate; methyl-3,5-dioxopentanoate; methyl-5-hydroxy-3-oxopentanoate; methyl-3-hydroxy-5-oxopentanoate; 3-oxoglutaryl-CoA, methyl ester; 3-hydroxyglutaryl-CoA, methyl ester; ethyl crotanate; ethyl-3,5-dioxopentanoate; ethyl-5-hydroxy-3-xopentanoate; ethyl-3-hydroxy-5-oxopentanoate; 3-oxoglutaryl-CoA, ethyl ester; 3-hydroxyglutaryl-CoA, ethyl ester; n-propyl crotanate; n-propyl-3,5-dioxopentanoate; n-propyl-5-hydroxy-3-oxopentanoate; n-propyl-3-hydroxy-5-oxopentanoate; 3-oxoglutaryl-CoA, n-propyl ester; and 3-hydroxyglutaryl-CoA, n-propyl ester. Other biosynthetically accessible O-carboxylates can include medium to long chain groups, that is C7-C22, O-carboxylate esters derived from fatty alcohols, such heptyl, octyl, nonyl, decyl, undecyl, lauryl, tridecyl, myristyl, pentadecyl, cetyl, palmitolyl, heptadecyl, stearyl, nonadecyl, arachidyl, heneicosyl, and behenyl alcohols, any one of which can be optionally branched and/or contain unsaturations. O-carboxylate esters can also be accessed via a biochemical or chemical process, such as esterification of a free carboxylic acid product or transesterification of an O- or S-carboxylate. S-carboxylates are exemplified by CoA S-esters, cysteinyl S-esters, alkylthioesters, and various aryl and heteroaryl thioesters.

The non-naturally occurring microbial organisms of the invention can be produced by introducing expressible nucleic acids encoding one or more of the enzymes or proteins participating in one or more butadiene biosynthetic pathways. Depending on the host microbial organism chosen for biosynthesis, nucleic acids for some or all of a particular butadiene biosynthetic pathway can be expressed. For example, if a chosen host is deficient in one or more enzymes or proteins for a desired biosynthetic pathway, then expressible nucleic acids for the deficient enzyme(s) or protein(s) are introduced into the host for subsequent exogenous expression. Alternatively, if the chosen host exhibits endogenous expression of some pathway genes, but is deficient in others, then an encoding nucleic acid is needed for the deficient enzyme(s) or protein(s) to achieve butadiene biosynthesis. Thus, a non-naturally occurring microbial organism of the invention can be produced by introducing exogenous enzyme or protein activities to obtain a desired biosynthetic pathway or a desired biosynthetic pathway can be obtained by introducing one or more exogenous enzyme or protein activities that, together with one or more endogenous enzymes or proteins, produces a desired product such as butadiene.

Host microbial organisms can be selected from, and the non-naturally occurring microbial organisms generated in, for example, bacteria, yeast, fungus or any of a variety of other microorganisms applicable to fermentation processes. Exemplary bacteria include species selected from *Escherichia coli, Klebsiella oxytoca, Anaerobiospirillum succiniciproducens, Actinobacillus succinogenes, Mannheimia succiniciproducens, Rhizobium etli, Bacillus subtilis, Corynebacterium glutamicum, Gluconobacter oxydans, Zymomonas mobilis, Lactococcus lactis, Lactobacillus plan-*

*tarum, Streptomyces coelicolor, Clostridium acetobutylicum, Pseudomonas fluorescens*, and *Pseudomonas putida*. Exemplary yeasts or fungi include species selected from *Saccharomyces cerevisiae, Schizosaccharomyces pombe, Kluyveromyces lactis, Kluyveromyces marxianus, Aspergillus terreus, Aspergillus niger, Pichia pastoris, Rhizopus arrhizus, Rhizobus oryzae, Yarrowia lipolytica*, and the like. *E. coli* is a particularly useful host organism since it is a well characterized microbial organism suitable for genetic engineering. Other particularly useful host organisms include yeast such as *Saccharomyces cerevisiae*. It is understood that any suitable microbial host organism can be used to introduce metabolic and/or genetic modifications to produce a desired product.

Depending on the butadiene biosynthetic pathway constituents of a selected host microbial organism, the non-naturally occurring microbial organisms of the invention will include at least one exogenously expressed butadiene pathway-encoding nucleic acid and up to all encoding nucleic acids for one or more butadiene biosynthetic pathways. For example, butadiene biosynthesis can be established in a host deficient in a pathway enzyme or protein through exogenous expression of the corresponding encoding nucleic acid. In a host deficient in all enzymes or proteins of a butadiene pathway, exogenous expression of all enzyme or proteins in the pathway can be included, although it is understood that all enzymes or proteins of a pathway can be expressed even if the host contains at least one of the pathway enzymes or proteins. For example, exogenous expression of all enzymes or proteins in a pathway for production of butadiene can be included, such as an acetyl-CoA:acetyl-CoA acyltransferase, an acetoacetyl-CoA reductase, a 3-hydroxybutyryl-CoA dehydratase, a crotonyl-CoA reductase (aldehyde forming), a crotonaldehyde reductase (alcohol forming), a crotyl alcohol kinase, a 2-butenyl-4-phosphate kinase and a butadiene synthase (FIG. 2, steps A-H).

Given the teachings and guidance provided herein, those skilled in the art will understand that the number of encoding nucleic acids to introduce in an expressible form will, at least, parallel the butadiene pathway deficiencies of the selected host microbial organism. Therefore, a non-naturally occurring microbial organism of the invention can have one, two, three, four, five, six, seven, eight, nine or ten, up to all nucleic acids encoding the enzymes or proteins constituting a butadiene biosynthetic pathway disclosed herein. In some embodiments, the non-naturally occurring microbial organisms also can include other genetic modifications that facilitate or optimize butadiene biosynthesis or that confer other useful functions onto the host microbial organism. One such other functionality can include, for example, augmentation of the synthesis of one or more of the butadiene pathway precursors such as acetyl-CoA, glutaconyl-CoA, glutaryl-CoA, 3-aminobutyryl-CoA, 4-hydroxybutyryl-CoA, erythrose-4-phosphate or malonyl-CoA.

Generally, a host microbial organism is selected such that it produces the precursor of a butadiene pathway, either as a naturally produced molecule or as an engineered product that either provides de novo production of a desired precursor or increased production of a precursor naturally produced by the host microbial organism. For example, acetyl-CoA, glutaconyl-CoA, glutaryl-CoA, 3-aminobutyryl-CoA, 4-hydroxybutyryl-CoA, erythrose-4-phosphate or malonyl-CoA are produced naturally in a host organism such as *E. coli*. A host organism can be engineered to increase production of a precursor, as disclosed herein. In addition, a microbial organism that has been engineered to produce a desired precursor can be used as a host organism and further engineered to express enzymes or proteins of a butadiene pathway.

In some embodiments, a non-naturally occurring microbial organism of the invention is generated from a host that contains the enzymatic capability to synthesize butadiene. In this specific embodiment it can be useful to increase the synthesis or accumulation of a butadiene pathway product to, for example, drive butadiene pathway reactions toward butadiene production. Increased synthesis or accumulation can be accomplished by, for example, overexpression of nucleic acids encoding one or more of the above-described butadiene pathway enzymes or proteins. Over expression the enzyme or enzymes and/or protein or proteins of the butadiene pathway can occur, for example, through exogenous expression of the endogenous gene or genes, or through exogenous expression of the heterologous gene or genes. Therefore, naturally occurring organisms can be readily generated to be non-naturally occurring microbial organisms of the invention, for example, producing butadiene, through overexpression of one, two, three, four, five, six, seven, eight, nine, or ten, that is, up to all nucleic acids encoding butadiene biosynthetic pathway enzymes or proteins. In addition, a non-naturally occurring organism can be generated by mutagenesis of an endogenous gene that results in an increase in activity of an enzyme in the butadiene biosynthetic pathway.

In particularly useful embodiments, exogenous expression of the encoding nucleic acids is employed. Exogenous expression confers the ability to custom tailor the expression and/or regulatory elements to the host and application to achieve a desired expression level that is controlled by the user. However, endogenous expression also can be utilized in other embodiments such as by removing a negative regulatory effector or induction of the gene's promoter when linked to an inducible promoter or other regulatory element. Thus, an endogenous gene having a naturally occurring inducible promoter can be up-regulated by providing the appropriate inducing agent, or the regulatory region of an endogenous gene can be engineered to incorporate an inducible regulatory element, thereby allowing the regulation of increased expression of an endogenous gene at a desired time. Similarly, an inducible promoter can be included as a regulatory element for an exogenous gene introduced into a non-naturally occurring microbial organism.

It is understood that, in methods of the invention, any of the one or more exogenous nucleic acids can be introduced into a microbial organism to produce a non-naturally occurring microbial organism of the invention. The nucleic acids can be introduced so as to confer, for example, a butadiene biosynthetic pathway onto the microbial organism. Alternatively, encoding nucleic acids can be introduced to produce an intermediate microbial organism having the biosynthetic capability to catalyze some of the required reactions to confer butadiene biosynthetic capability. For example, a non-naturally occurring microbial organism having a butadiene biosynthetic pathway can comprise at least two exogenous nucleic acids encoding desired enzymes or proteins, such as the combination of a crotyl alcohol kinase and a butadiene synthase, or alternatively a 4-(cytidine 5'-diphospho)-erythritol kinase and butadiene synthase, or alternatively a 1-hydroxy-2-butenyl 4-diphosphate synthase and a butadiene synthase, or alternatively a 3-hydroxy-5-phosphonatooxypentanoate kinase and a butadiene synthase, or alternatively a crotonyl-CoA hydrolase and a crotyl alcohol diphosphokinase, or alternatively a an erythrose reductase and butadiene synthase or alternatively a 3-oxo-glutaryl-CoA reductase (CoA reducing and alcohol forming) and 3-Hydroxy-5-[hydroxy(phosphonooxy)phosphoryl]oxy pentanoate decarboxylase, and the like. Thus, it is understood that any combination of two or more enzymes or proteins of a biosynthetic pathway can be included in a non-naturally occurring microbial organism of the invention. Similarly, it is understood that any combination of three or more enzymes or proteins of a biosynthetic pathway can be included in a non-naturally occurring microbial organism of the invention, for example, a crotyl alcohol kinase, a 2-butenyl-4-phosphate kinase and a butadiene synthase, or alternatively a 1-hydroxy-2-butenyl 4-diphosphate synthase, a 1-hydroxy-2-butenyl 4-diphosphate reductase, and butadiene synthase, or alternatively a 3-oxoglutaryl-CoA reductase, a 3-hydroxy-5-oxopentanoate reductase, and a butadiene synthase, or alternatively an acetyl-CoA:acetyl-CoA acyltransferase, a crotyl alcohol kinase and a butadiene synthase, or alternatively a glutaconyl-CoA decarboxylase, a crotonyl-CoA reductase (alcohol forming), and a crotyl alcohol diphosphokinase, or alternatively a an erythrose-4-phosphate kinase, a 4-(cytidine 5'-diphospho)-erythritol kinase and a 1-hydroxy-2-butenyl 4-diphosphate synthase, or alternatively a 3,5-dioxopentanoate reductase (aldehyde reducing), a butenyl 4-diphosphate isomerase, and a butadiene synthase, and so forth, as desired, so long as the combination of enzymes and/or proteins of the desired biosynthetic pathway results in production of the corresponding desired product. Similarly, any combination of four, such as a crotonaldehyde reductase (alcohol forming), a crotyl alcohol kinase, a 2-butenyl-4-phosphate kinase and a butadiene synthase, or alternatively a 1-hydroxy-2-butenyl 4-diphosphate synthase, a 1-hydroxy-2-butenyl 4-diphosphate reductase, a butenyl 4-diphosphate isomerase and butadiene synthase, or alternatively a 3-hydroxy-5-phosphonatooxypentanoate kinase, a 3-hydroxy-5-[hydroxy(phosphonooxy)phosphoryl]oxy pentanoate kinase, a butenyl 4-diphosphate isomerase and a butadiene synthase, or alternatively an erythrose-4-phosphate reductase, an erythritol-4-phospate cytidylyltransferase, a 4-(cytidine 5'-diphospho)-erythritol kinase and butadiene synthase, or alternatively a 3-aminobutyryl-CoA deaminase, a crotonyl-CoA reductase (alcohol forming), a crotyl alcohol diphosphokinase and a butadiene synthase, or alternatively an erythrose reductase, a 4-(cytidine 5'-diphospho)-erythritol kinase, an erythritol 2,4-cyclodiphosphate synthase and a 1-hydroxy-2-butenyl 4-diphosphate reductase, or alternatively a malonyl-CoA:acetyl-CoA acyltransferase, a 3-hydroxyglutaryl-CoA reductase (alcohol forming), a butenyl 4-diphosphate isomerase and a butadiene synthase, or more enzymes or proteins of a biosynthetic pathway as disclosed herein can be included in a non-naturally occurring microbial organism of the invention, as desired, so long as the combination of enzymes and/or proteins of the desired biosynthetic pathway results in production of the corresponding desired product.

In addition to the biosynthesis of butadiene as described herein, the non-naturally occurring microbial organisms and methods of the invention also can be utilized in various combinations with each other and with other microbial organisms and methods well known in the art to achieve product biosynthesis by other routes. For example, one alternative to produce butadiene other than use of the butadiene producers is through addition of another microbial organism capable of converting a butadiene pathway intermediate to butadiene. One such procedure includes, for example, the fermentation of a microbial organism that produces a butadiene pathway intermediate. The butadiene pathway intermediate can then be used as a substrate for a second microbial organism that converts the butadiene pathway intermediate to butadiene. The butadiene pathway intermediate can be added directly to another culture of the second organism or the original culture of the butadiene pathway intermediate producers can be depleted of these microbial organisms by, for example, cell separation, and then subsequent addition of the second organism to the fermentation broth can be utilized to produce the final product without intermediate purification steps.

In other embodiments, the non-naturally occurring microbial organisms and methods of the invention can be assembled in a wide variety of subpathways to achieve biosynthesis of, for example, butadiene. In these embodiments, biosynthetic pathways for a desired product of the invention can be segregated into different microbial organisms, and the different microbial organisms can be co-cultured to produce the final product. In such a biosynthetic scheme, the product of one microbial organism is the substrate for a second microbial organism until the final product is synthesized. For example, the biosynthesis of butadiene can be accomplished by constructing a microbial organism that contains biosynthetic pathways for conversion of one pathway intermediate to another pathway intermediate or the product. Alternatively, butadiene also can be biosynthetically produced from microbial organisms through co-culture or co-fermentation using two organisms in the same vessel, where the first microbial organism produces a butadiene intermediate and the second microbial organism converts the intermediate to butadiene.

Given the teachings and guidance provided herein, those skilled in the art will understand that a wide variety of combinations and permutations exist for the non-naturally occurring microbial organisms and methods of the invention together with other microbial organisms, with the co-culture of other non-naturally occurring microbial organisms having subpathways and with combinations of other chemical and/or biochemical procedures well known in the art to produce butadiene.

Sources of encoding nucleic acids for a butadiene pathway enzyme or protein can include, for example, any species where the encoded gene product is capable of catalyzing the referenced reaction. Such species include both prokaryotic and eukaryotic organisms including, but not limited to, bacteria, including archaea and eubacteria, and eukaryotes, including yeast, plant, insect, animal, and mammal, including human. Exemplary species for such sources include, for example, *Escherichia coli, Acidaminococcus fermentans, Acinetobacter baylyi, Acinetobacter calcoaceticus, Acinetobacter* sp. ADP1, *Acinetobacter* sp. Strain M-1, *Aquifex aeolicus, Arabidopsis thaliana, Arabidopsis thaliana* col, *Arabidopsis thaliana* col, *Archaeoglobus fulgidus* DSM 4304, *Azoarcus* sp. CIB, *Bacillus cereus, Bacillus subtilis, Bos Taurus, Brucella melitensis, Burkholderia ambifaria* AMMD, *Burkholderia phymatum, Campylobacter jejuni, Candida albicans, Candida magnoliae, Chloroflexus aurantiacus, Citrobacter youngae* ATCC 29220, *Clostridium acetobutylicum, Clostridium aminobutyricum, Clostridium beijerinckii, Clostridium beijerinckii* NCIMB 8052, *Clostridium beijerinckii* NRRL B593, *Clostridium botulinum* C str. Eklund, *Clostridium kluyveri, Clostridium kluyveri* DSM 555, *Clostridium novyi* NT, *Clostridium propionicum, Clostridium saccharoperbutylacetonicum, Corynebacterium glutamicum* ATCC 13032, *Cupriavidus taiwanensis, Cyanobium* PCC7001, *Dictyostelium discoideum* AX4, *Enterococcus faecalis, Erythrobacter* sp. NAP1, *Escherichia coli* K12, *Escherichia coli* str. K-12 substr. MG1655, *Eubacterium rectale* ATCC 33656, *Fusobacterium nucleatum, Fusobacterium nucleatum* subsp. *nucleatum* ATCC 25586, *Geobacillus thermoglucosidasius, Haematococcus pluvialis, Haemophilus influenzae, Haloarcula marismortui* ATCC 43049, *Helicobacter pylori, Homo sapiens, Klebsiella pneumoniae, Lactobacillus plantarum, Leuconostoc mesenteroides,* marine gamma proteobacterium HTCC2080, *Metallosphaera sedula, Methanocaldococcus jannaschii, Mus musculus,*

*Mycobacterium avium* subsp. *paratuberculosis* K-10, *Mycobacterium bovis* BCG, *Mycobacterium marinum* M, *Mycobacterium smegmatis* MC2 155, *Mycobacterium tuberculosis*, *Mycoplasma pneumoniae* M129, *Nocardia farcinica* IFM 10152, *Nocardia iowensis* (sp. NRRL 5646), *Oryctolagus cuniculus*, *Paracoccus denitrificans*, *Penicillium chrysogenum*, *Populus alba*, *Populus tremula×Populus alba*, *Porphyromonas gingivalis*, *Porphyromonas gingivalis* W83, *Pseudomonas aeruginosa*, *Pseudomonas aeruginosa* PAO1, *Pseudomonas fluorescens*, *Pseudomonas fluorescens* Pf-5, *Pseudomonas knackmussii* (B13), *Pseudomonas putida*, *Pseudomonas putida* E23, *Pseudomonas putida* KT2440, *Pseudomonas* sp, *Pueraria Montana*, *Pyrobaculum aerophilum* str. IM2, *Pyrococcus furiosus*, *Ralstonia eutropha*, *Ralstonia eutropha* H16, *Ralstonia eutropha* H16, *Ralstonia metallidurans*, *Rattus norvegicus*, *Rhodobacter spaeroides*, *Rhodococcus rubber*, *Rhodopseudomonas palustris*, *Roseburia intestinalis* L1-82, *Roseburia inulinivorans* DSM 16841, *Roseburia* sp. A2-183, *Roseiflexus castenholzii*, *Saccharomyces cerevisiae*, *Saccharopolyspora rythraea* NRRL 2338, *Salmonella enterica* subsp. *arizonae serovar*, *Salmonella typhimurium*, *Schizosaccharomyces pombe*, *Simmondsia chinensis*, *Sinorhizobium meliloti*, *Staphylococcus*, *ureus*, *Streptococcus pneumoniae*, *Streptomyces coelicolor*, *Streptomyces griseus* subsp. *griseus*, BRC 13350, *Streptomyces* sp. ACT-1, *Sulfolobus acidocaldarius*, *Sulfolobus shibatae*, *Sulfolobus solfataricus*, *Sulfolobus tokodaii*, *Synechocystis* sp. strain PCC6803, *Syntrophus*, *ciditrophicus*, *Thermoanaerobacter brockii* HTD4, *Thermoanaerobacter tengcongensis* MB4, *Thermosynechococcus elongates*, *Thermotoga maritime* MSB8, *Thermus thermophilus*, *Thermus*, *hermophilus* HB8, *Trichomonas vaginalis* G3, *Trichosporonoides megachiliensis*, *Trypanosoma brucei*, *Tsukamurella paurometabola* DSM 20162, *Yersinia intermedia* ATCC 29909, *Zoogloea ramigera*, *Zygosaccharomyces rouxii*, *Zymomonas mobilis*, as well as other exemplary species disclosed herein are available as source organisms for corresponding genes. However, with the complete genome sequence available for now more than 550 species (with more than half of these available on public databases such as the NCBI), including 395 microorganism genomes and a variety of yeast, fungi, plant, and mammalian genomes, the identification of genes encoding the requisite butadiene biosynthetic activity for one or more genes in related or distant species, including for example, homologues, orthologs, paralogs and nonorthologous gene displacements of known genes, and the interchange of genetic alterations between organisms is routine and well known in the art. Accordingly, the metabolic alterations allowing biosynthesis of butadiene described herein with reference to a particular organism such as *E. coli* can be readily applied to other microorganisms, including prokaryotic and eukaryotic organisms alike. Given the teachings and guidance provided herein, those skilled in the art will know that a metabolic alteration exemplified in one organism can be applied equally to other organisms.

In some instances, such as when an alternative butadiene biosynthetic pathway exists in an unrelated species, butadiene biosynthesis can be conferred onto the host species by, for example, exogenous expression of a paralog or paralogs from the unrelated species that catalyzes a similar, yet non-identical metabolic reaction to replace the referenced reaction. Because certain differences among metabolic networks exist between different organisms, those skilled in the art will understand that the actual gene usage between different organisms may differ. However, given the teachings and guidance provided herein, those skilled in the art also will understand that the teachings and methods of the invention can be applied to all microbial organisms using the cognate metabolic alterations to those exemplified herein to construct a microbial organism in a species of interest that will synthesize butadiene.

Methods for constructing and testing the expression levels of a non-naturally occurring butadiene-producing host can be performed, for example, by recombinant and detection methods well known in the art. Such methods can be found described in, for example, Sambrook et al., *Molecular Cloning: A Laboratory Manual*, Third Ed., Cold Spring Harbor Laboratory, New York (2001); and Ausubel et al., *Current Protocols in Molecular Biology*, John Wiley and Sons, Baltimore, Md. (1999).

Exogenous nucleic acid sequences involved in a pathway for production of butadiene can be introduced stably or transiently into a host cell using techniques well known in the art including, but not limited to, conjugation, electroporation, chemical transformation, transduction, transfection, and ultrasound transformation. For exogenous expression in *E. coli* or other prokaryotic cells, some nucleic acid sequences in the genes or cDNAs of eukaryotic nucleic acids can encode targeting signals such as an N-terminal mitochondrial or other targeting signal, which can be removed before transformation into prokaryotic host cells, if desired. For example, removal of a mitochondrial leader sequence led to increased expression in *E. coli* (Hoffmeister et al., *J. Biol. Chem.* 280: 4329-4338 (2005)). For exogenous expression in yeast or other eukaryotic cells, genes can be expressed in the cytosol without the addition of leader sequence, or can be targeted to mitochondrion or other organelles, or targeted for secretion, by the addition of a suitable targeting sequence such as a mitochondrial targeting or secretion signal suitable for the host cells. Thus, it is understood that appropriate modifications to a nucleic acid sequence to remove or include a targeting sequence can be incorporated into an exogenous nucleic acid sequence to impart desirable properties. Furthermore, genes can be subjected to codon optimization with techniques well known in the art to achieve optimized expression of the proteins.

An expression vector or vectors can be constructed to include one or more butadiene biosynthetic pathway encoding nucleic acids as exemplified herein operably linked to expression control sequences functional in the host organism. Expression vectors applicable for use in the microbial host organisms of the invention include, for example, plasmids, phage vectors, viral vectors, episomes and artificial chromosomes, including vectors and selection sequences or markers operable for stable integration into a host chromosome. Additionally, the expression vectors can include one or more selectable marker genes and appropriate expression control sequences. Selectable marker genes also can be included that, for example, provide resistance to antibiotics or toxins, complement auxotrophic deficiencies, or supply critical nutrients not in the culture media. Expression control sequences can include constitutive and inducible promoters, transcription enhancers, transcription terminators, and the like which are well known in the art. When two or more exogenous encoding nucleic acids are to be co-expressed, both nucleic acids can be inserted, for example, into a single expression vector or in separate expression vectors. For single vector expression, the encoding nucleic acids can be operationally linked to one common expression control sequence or linked to different expression control sequences, such as one inducible promoter and one constitutive promoter. The transformation of exogenous nucleic acid sequences involved in a metabolic or synthetic pathway can be confirmed using methods well known in the art. Such methods include, for example, nucleic acid analysis such as Northern blots or polymerase chain reaction (PCR) amplification of mRNA, or immunoblotting for expression of gene products, or other suitable analytical methods to test the expression of an introduced nucleic acid sequence or its corresponding gene product. It is understood by those skilled in the art that the exogenous nucleic acid is expressed in a sufficient amount to produce the desired product, and it is further understood that expression levels can be optimized to obtain sufficient expression using methods well known in the art and as disclosed herein.

In some embodiments, the invention provides a method for producing butadiene that includes culturing a non-naturally occurring microbial organism, including a microbial organism having a butadiene pathway, the butadiene pathway including at least one exogenous nucleic acid encoding a butadiene pathway enzyme expressed in a sufficient amount to produce butadiene, the butadiene pathway including an acetyl-CoA:acetyl-CoA acyltransferase, an acetoacetyl-CoA reductase, a 3-hydroxybutyryl-CoA dehydratase, a crotonyl-CoA reductase (aldehyde forming), a crotonaldehyde reductase (alcohol forming), a crotyl alcohol kinase, a 2-butenyl-4-phosphate kinase, a butadiene synthase, a crotonyl-CoA hydrolase, synthetase, or transferase, a crotonate reductase, a crotonyl-CoA reductase (alcohol forming), a glutaconyl-CoA decarboxylase, a glutaryl-CoA dehydrogenase, a 3-aminobutyryl-CoA deaminase, a 4-hydroxybutyryl-CoA dehydratase or a crotyl alcohol diphosphokinase (FIG. 2). In one aspect, the method includes a microbial organism having a butadiene pathway including an acetyl-CoA:acetyl-CoA acyltransferase, an acetoacetyl-CoA reductase, a 3-hydroxybutyryl-CoA dehydratase, a crotonyl-CoA reductase (aldehyde forming), a crotonaldehyde reductase (alcohol forming), a crotyl alcohol kinase, a 2-butenyl-4-phosphate kinase and a butadiene synthase (FIG. 2, steps A-H). In one aspect, the method includes a microbial organism having a butadiene pathway including an acetyl-CoA:acetyl-CoA acyltransferase, an acetoacetyl-CoA reductase, a 3-hydroxybutyryl-CoA dehydratase, a crotyl alcohol kinase, a 2-butenyl-4-phosphate kinase, a butadiene synthase and crotonyl-CoA reductase (alcohol forming) (FIG. 2, steps A-C, K, F, G, H). In one aspect, the method includes a microbial organism having a butadiene pathway including an acetyl-CoA:acetyl-CoA acyltransferase, an acetoacetyl-CoA reductase, a 3-hydroxybutyryl-CoA dehydratase, a butadiene synthase, a crotonyl-CoA reductase (alcohol forming) and a crotyl alcohol diphosphokinase (FIG. 2, steps A-C, K, P, H). In one aspect, the method includes a microbial organism having a butadiene pathway including an acetyl-CoA:acetyl-CoA acyltransferase, an acetoacetyl-CoA reductase, a 3-hydroxybutyryl-CoA dehydratase, a crotonaldehyde reductase (alcohol forming), a crotyl alcohol kinase, a 2-butenyl-4-phosphate kinase, a butadiene synthase, a crotonyl-CoA hydrolase, synthetase, or transferase and a crotonate reductase, (FIG. 2, steps A-C, I, J, E, F, G, H). In one aspect, the method includes a microbial organism having a butadiene pathway including an acetyl-CoA:acetyl-CoA acyltransferase, an acetoacetyl-CoA reductase, a 3-hydroxybutyryl-CoA dehydratase, a crotonaldehyde reductase (alcohol forming), a butadiene synthase, a crotonyl-CoA hydrolase, synthetase or transferase, a crotonate reductase and a crotyl alcohol diphosphokinase (FIG. 2, steps A-C, I, J, E, P, H). In one aspect, the method includes a microbial organism having a butadiene pathway including an acetyl-CoA:acetyl-CoA acyltransferase, an acetoacetyl-CoA reductase, a 3-hydroxybutyryl-CoA dehydratase, a crotonyl-CoA reductase (aldehyde forming), a crotonaldehyde reductase (alcohol forming), a butadiene synthase and a crotyl alcohol diphosphokinase (FIG. 2, steps A-E, P, H). In one aspect, the method includes a microbial organism having a butadiene pathway including a glutaconyl-CoA decarboxylase, a crotonyl-CoA reductase (aldehyde forming), a crotonaldehyde reductase (alcohol forming), a crotyl alcohol kinase, a 2-butenyl-4-phosphate kinase and a butadiene synthase (FIG. 2, steps L, D-H). In one aspect, the method includes a microbial organism having a butadiene pathway including a glutaconyl-CoA decarboxylase, a crotyl alcohol kinase, a 2-butenyl-4-phosphate kinase, a butadiene synthase and crotonyl-CoA reductase (alcohol forming) (FIG. 2, steps L, K, F, G, H). In one aspect, the method includes a microbial organism having a butadiene pathway including a glutaconyl-CoA decarboxylase, a butadiene synthase, a crotonyl-CoA reductase (alcohol forming) and a crotyl alcohol diphosphokinase (FIG. 2, steps L, K, P, H). In one aspect, the method includes a microbial organism having a butadiene pathway including a glutaconyl-CoA decarboxylase, a crotonaldehyde reductase (alcohol forming), a crotyl alcohol kinase, a 2-butenyl-4-phosphate kinase, a butadiene synthase, a crotonyl-CoA hydrolase, synthetase, or transferase and a crotonate reductase (FIG. 2, steps L, I, J, E, F, G, H). In one aspect, the method includes a microbial organism having a butadiene pathway including a glutaconyl-CoA decarboxylase, a crotonaldehyde reductase (alcohol forming), a butadiene synthase, a crotonyl-CoA hydrolase, synthetase or transferase, a crotonate reductase and a crotyl alcohol diphosphokinase (FIG. 2, steps L, I, J, E, P, H). In one aspect, the method includes a microbial organism having a butadiene pathway including a 3-hydroxybutyryl-CoA dehydratase, a crotonyl-CoA reductase (aldehyde forming), a crotonaldehyde reductase (alcohol forming), a butadiene a glutaconyl-CoA decarboxylase and a crotyl alcohol diphosphokinase (FIG. 2, steps L, C, D, E, P, H). In one aspect, the method includes a microbial organism having a butadiene pathway including a glutaryl-CoA dehydrogenase, a crotonyl-CoA reductase (aldehyde forming), a crotonaldehyde reductase (alcohol forming), a crotyl alcohol kinase, a 2-butenyl-4-phosphate kinase and a butadiene synthase (FIG. 2, steps M, D-H). In one aspect, the method includes a microbial organism having a butadiene pathway including a glutaryl-CoA dehydrogenase, a crotyl alcohol kinase, a 2-butenyl-4-phosphate kinase, a butadiene synthase and crotonyl-CoA reductase (alcohol forming) (FIG. 2, steps M, K, F, G, H). In one aspect, the method includes a microbial organism having a butadiene pathway including a glutaryl-CoA dehydrogenase, a butadiene synthase, a crotonyl-CoA reductase (alcohol forming) and a crotyl alcohol diphosphokinase (FIG. 2, steps M, K, P, H). In one aspect, the method includes a microbial organism having a butadiene pathway including a glutaryl-CoA dehydrogenase, a crotonaldehyde reductase (alcohol forming), a crotyl alcohol kinase, a 2-butenyl-4-phosphate kinase, a butadiene synthase, a crotonyl-CoA hydrolase, synthetase, or transferase and a crotonate reductase (FIG. 2, steps M, I, J, E, F, G, H). In one aspect, the method includes a microbial organism having a butadiene pathway including a glutaryl-CoA dehydrogenase, a crotonaldehyde reductase (alcohol forming), a butadiene synthase, a crotonyl-CoA hydrolase, synthetase or transferase, a crotonate reductase and a crotyl alcohol diphosphokinase (FIG. 2, steps M, I, J, E, P, H). In one aspect, the method includes a microbial organism having a butadiene pathway including a 3-hydroxybutyryl-CoA dehydratase, a crotonyl-CoA reductase (aldehyde forming), a crotonaldehyde reductase (alcohol forming), a butadiene synthase, a glutaryl-CoA dehydrogenase and a crotyl alcohol diphosphokinase (FIG. 2, steps M, C, D, E, P, H). In one aspect, the method includes a microbial organism having a butadiene pathway including a 3-aminobutyryl-CoA deaminase, a crotonyl-CoA reductase (aldehyde forming), a crotonaldehyde reductase (alcohol forming), a crotyl alcohol kinase, a 2-butenyl-4-phosphate kinase and a butadiene synthase (FIG. 2, steps N, D-H). In one aspect, the method includes a microbial organism having a butadiene pathway including a 3-aminobutyryl-CoA deaminase, a crotyl alcohol kinase, a 2-butenyl-4-phosphate kinase, a butadiene synthase and crotonyl-CoA reductase (alcohol forming) (FIG. 2, steps N, K, F, G, H). In one aspect, the method includes a microbial organism having a butadiene pathway including a 3-aminobutyryl-CoA deaminase, a butadiene synthase, a crotonyl-CoA reductase (alcohol forming) and a crotyl alcohol diphosphokinase (FIG. 2, steps N, K, P, H). In one aspect, the method includes a microbial organism having a butadiene pathway including a 3-aminobutyryl-CoA deaminase, a crotonaldehyde reductase (alcohol forming), a crotyl alcohol kinase, a 2-butenyl-4-phosphate kinase, a butadiene synthase, a crotonyl-CoA hydrolase, synthetase, or transferase and a crotonate reductase (FIG. 2, steps N, I, J, E, F, G, H). In one aspect, the method includes a microbial organism having a butadiene pathway including a 3-aminobutyryl-CoA deaminase, a crotonaldehyde reductase (alcohol forming), a butadiene synthase, a crotonyl-CoA hydrolase, synthetase or transferase, a crotonate reductase and a crotyl alcohol diphosphokinase (FIG. 2, steps N, I, J, E, P, H). In one aspect, the method includes a microbial organism having a butadiene pathway including a 3-hydroxybutyryl-CoA dehydratase, a crotonyl-CoA reductase (aldehyde forming), a crotonaldehyde reductase (alcohol forming), a butadiene synthase, a 3-aminobutyryl-CoA deaminase and a crotyl alcohol diphosphokinase (FIG. 2, steps N, C, D, E, P, H). In one aspect, the method includes a microbial organism having a butadiene pathway including a 4-hydroxybutyryl-CoA dehydratase, a crotonyl-CoA reductase (aldehyde forming), a crotonaldehyde reductase (alcohol forming), a crotyl alcohol kinase, a 2-butenyl-4-phosphate kinase and a butadiene synthase (FIG. 2, steps O, D-H). In one aspect, the method includes a microbial organism having a butadiene pathway including a 4-hydroxybutyryl-CoA dehydratase, a crotyl alcohol kinase, a 2-butenyl-4-phosphate kinase, a butadiene synthase and crotonyl-CoA reductase (alcohol forming) (FIG. 2, steps O, K, F, G, H). In one aspect, the method includes a microbial organism having a butadiene pathway including a 4-hydroxybutyryl-CoA dehydratase, a butadiene synthase, a crotonyl-CoA reductase (alcohol forming) and a crotyl alcohol diphosphokinase (FIG. 2, steps O, K, P, H). In one aspect, the method includes a microbial organism having a butadiene pathway including a 4-hydroxybutyryl-CoA dehydratase, a crotonaldehyde reductase (alcohol forming), a crotyl alcohol kinase, a 2-butenyl-4-phosphate kinase, a butadiene synthase, a crotonyl-CoA hydrolase, synthetase, or transferase and a crotonate reductase (FIG. 2, steps O, I, J, E, F, G, H). In one aspect, the method includes a microbial organism having a butadiene pathway including a 4-hydroxybutyryl-CoA dehydratase, a crotonaldehyde reductase (alcohol forming), a butadiene synthase, a crotonyl-CoA hydrolase, synthetase or transferase, a crotonate reductase and a crotyl alcohol diphosphokinase (FIG. 2, steps O, I, J, E, P, H). In one aspect, the method includes a microbial organism having a butadiene pathway including a 3-hydroxybutyryl-CoA dehydratase, a crotonyl-CoA reductase (aldehyde forming), a crotonaldehyde reductase (alcohol forming), a butadiene synthase, a 4-hydroxybutyryl-CoA dehydratase and a crotyl alcohol diphosphokinase (FIG. 2, steps O, C, D, E, P, H).

In some embodiments, the invention provides a method for producing butadiene that includes culturing a non-naturally occurring microbial organism, including a microbial organism having a butadiene pathway, the butadiene pathway including at least one exogenous nucleic acid encoding a butadiene pathway enzyme expressed in a sufficient amount to produce butadiene, the butadiene pathway including an erythrose-4-phosphate reductase, an erythritol-4-phospate cytidylyltransferase, a 4-(cytidine 5'-diphospho)-erythritol kinase, an erythritol 2,4-cyclodiphosphate synthase, a 1-hydroxy-2-butenyl 4-diphosphate synthase, a 1-hydroxy-2-butenyl 4-diphosphate reductase, a butenyl 4-diphosphate isomerase, a butadiene synthase, an erythrose-4-phosphate kinase, an erythrose reductase or an erythritol kinase (FIG. 3). In one aspect, the method includes a microbial organism having a butadiene pathway including an erythrose-4-phosphate reductase, an erythritol-4-phospate cytidylyltransferase, a 4-(cytidine 5'-diphospho)-erythritol kinase, an erythritol 2,4-cyclodiphosphate synthase, a 1-hydroxy-2-butenyl 4-diphosphate synthase, a 1-hydroxy-2-butenyl 4-diphosphate reductase and a butadiene synthase (FIG. 3, steps A-F, and H). In one aspect, the method includes a microbial organism having a butadiene pathway including an erythrose-4-phosphate reductase, an erythritol-4-phospate cytidylyltransferase, a 4-(cytidine 5'-diphospho)-erythritol kinase, an erythritol 2,4-cyclodiphosphate synthase, a 1-hydroxy-2-butenyl 4-diphosphate synthase, a 1-hydroxy-2-butenyl 4-diphosphate reductase, a butenyl 4-diphosphate isomerase and butadiene synthase (FIG. 3, steps A-H). In one aspect, the method includes a microbial organism having a butadiene pathway including an erythritol-4-phospate cytidylyltransferase, a 4-(cytidine 5'-diphospho)-erythritol kinase, an erythritol 2,4-cyclodiphosphate synthase, a 1-hydroxy-2-butenyl 4-diphosphate synthase, a 1-hydroxy-2-butenyl 4-diphosphate reductase, a butadiene synthase, an erythrose-4-phosphate kinase, an erythrose reductase and a erythritol kinase (FIG. 3, steps I, J, K, B-F, H). In one aspect, the method includes a microbial organism having a butadiene pathway including an erythritol-4-phospate cytidylyltransferase, a 4-(cytidine 5'-diphospho)-erythritol kinase, an erythritol 2,4-cyclodiphosphate synthase, a 1-hydroxy-2-butenyl 4-diphosphate synthase, a 1-hydroxy-2-butenyl 4-diphosphate reductase, a butenyl 4-diphosphate isomerase, a butadiene synthase, an erythrose-4-phosphate kinase, an erythrose reductase and an erythritol kinase (FIG. 3, steps I, J, K, B-H).

In some embodiments, the invention provides a method for producing butadiene that includes culturing a non-naturally occurring microbial organism, including a microbial organism having a butadiene pathway, the butadiene pathway including at least one exogenous nucleic acid encoding a butadiene pathway enzyme expressed in a sufficient amount to produce butadiene, the butadiene pathway including a malonyl-CoA:acetyl-CoA acyltransferase, a 3-oxoglutaryl-CoA reductase (ketone-reducing), a 3-hydroxyglutaryl-CoA reductase (aldehyde forming), a 3-hydroxy-5-oxopentanoate reductase, a 3,5-dihydroxypentanoate kinase, a 3-hydroxy-5-phosphonatooxypentanoate kinase, a 3-hydroxy-5-[hydroxy(phosphonooxy)phosphoryl]oxy pentanoate decarboxylase, a butenyl 4-diphosphate isomerase, a butadiene synthase, a 3-hydroxyglutaryl-CoA reductase (alcohol forming), a 3-oxoglutaryl-CoA reductase (aldehyde forming), a 3,5-dioxopentanoate reductase (ketone reducing), a 3,5-dioxopentanoate reductase (aldehyde reducing), a 5-hydroxy-3-oxopentanoate reductase or a 3-oxo-glutaryl-CoA reductase (CoA reducing and alcohol forming) (FIG. 4). In one aspect, the method includes a microbial organism having a butadiene pathway including a malonyl-CoA:acetyl-CoA acyltransferase, a 3-oxoglutaryl-CoA reductase (ketone-reducing), a 3-hydroxyglutaryl-CoA reductase (aldehyde forming), a 3-hydroxy-5-oxopentanoate reductase, a 3,5-dihydroxypentanoate kinase, a 3-hydroxy-5-phosphonatooxypentanoate kinase, a 3-hydroxy-5-[hydroxy(phosphonooxy)phosphoryl] oxy pentanoate decarboxylase, a butenyl 4-diphosphate isomerase and a butadiene synthase (FIG. 4, steps A-I). In one aspect, the method includes a microbial organism having a butadiene pathway including a malonyl-CoA:acetyl-CoA acyltransferase, a 3,5-dihydroxypentanoate kinase, a 3-hydroxy-5-phosphonatooxypentanoate kinase, a 3-hydroxy-5-[hydroxy(phosphonooxy)phosphoryl]oxy pentanoate decarboxylase, a butenyl 4-diphosphate isomerase, a butadiene synthase, a 3-oxoglutaryl-CoA reductase (aldehyde forming), a 3,5-dioxopentanoate reductase (aldehyde reducing) and a 5-hydroxy-3-oxopentanoate reductase. (FIG. 4, steps A, K, M, N, E, F, G, H, I). In one aspect, the method includes a microbial organism having a butadiene pathway including a malonyl-CoA:acetyl-CoA acyltransferase, a 3-hydroxy-5-oxopentanoate reductase, a 3,5-dihydroxypentanoate kinase, a 3-Hydroxy-5-phosphonatooxypentanoate kinase, a 3-Hydroxy-5-[hydroxy(phosphonooxy)phosphoryl]oxy pentanoate decarboxylase, a butenyl 4-diphosphate isomerase, a butadiene synthase, a 3-oxoglutaryl-CoA reductase (aldehyde forming) and a 3,5-dioxopentanoate reductase (ketone reducing). (FIG. 4, steps A, K, L, D, E, F, G, H, I). In one aspect, the method includes a microbial organism having a butadiene pathway including a malonyl-CoA:acetyl-CoA acyltransferase, a 3,5-dihydroxypentanoate kinase, a 3-hydroxy-5-phosphonatooxypentanoate kinase, a 3-hydroxy-5-[hydroxy(phosphonooxy)phosphoryl]oxy pentanoate decarboxylase, a butenyl 4-diphosphate isomerase, a butadiene synthase, a 5-hydroxy-3-oxopentanoate reductase and a 3-oxo-glutaryl-CoA reductase (CoA reducing and alcohol forming). (FIG. 4, steps A, O, N, E, F, G, H, I). In one aspect, the method includes a microbial organism having a butadiene pathway including a malonyl-CoA:acetyl-CoA acyltransferase, a 3-oxoglutaryl-CoA reductase (ketone-reducing), a 3,5-dihydroxypentanoate kinase, a 3-hydroxy-5-phosphonatooxypentanoate kinase, a 3-hydroxy-5-[hydroxy(phosphonooxy)phosphoryl]oxy pentanoate decarboxylase, a butenyl 4-diphosphate isomerase, a butadiene synthase and a 3-hydroxyglutaryl-CoA reductase (alcohol forming). (FIG. 4, steps A, B, J, E, F, G, H, I).

Suitable purification and/or assays to test for the production of butadiene can be performed using well known methods. Suitable replicates such as triplicate cultures can be grown for each engineered strain to be tested. For example, product and byproduct formation in the engineered production host can be monitored. The final product and intermediates, and other organic compounds, can be analyzed by methods such as HPLC (High Performance Liquid Chromatography), GC-MS (Gas Chromatography-Mass Spectroscopy) and LC-MS (Liquid Chromatography-Mass Spectroscopy) or other suitable analytical methods using routine procedures well known in the art. The release of product in the fermentation broth can also be tested with the culture supernatant. Byproducts and residual glucose can be quantified by HPLC using, for example, a refractive index detector for glucose and alcohols, and a UV detector for organic acids (Lin et al., *Biotechnol. Bioeng.* 90:775-779 (2005)), or other suitable assay and detection methods well known in the art. The individual enzyme or protein activities from the exogenous DNA sequences can also be assayed using methods well known in the art. For typical Assay Methods, see Manual on Hydrocarbon Analysis (ASTM Manula Series, A. W. Drews, ed., 6th edition, 1998, American Society for Testing and Materials, Baltimore, Md.

The butadiene can be separated from other components in the culture using a variety of methods well known in the art. Such separation methods include, for example, extraction procedures as well as methods that include continuous liquid-liquid extraction, pervaporation, membrane filtration, membrane separation, reverse osmosis, electrodialysis, distillation, crystallization, centrifugation, extractive filtration, ion exchange chromatography, size exclusion chromatography, adsorption chromatography, and ultrafiltration. All of the above methods are well known in the art.

Any of the non-naturally occurring microbial organisms described herein can be cultured to produce and/or secrete the biosynthetic products of the invention. For example, the butadiene producers can be cultured for the biosynthetic production of butadiene.

For the production of butadiene, the recombinant strains are cultured in a medium with carbon source and other essential nutrients. It is sometimes desirable and can be highly desirable to maintain anaerobic conditions in the fermenter to reduce the cost of the overall process. Such conditions can be obtained, for example, by first sparging the medium with nitrogen and then sealing the flasks with a septum and crimp-cap. For strains where growth is not observed anaerobically, microaerobic or substantially anaerobic conditions can be applied by perforating the septum with a small hole for limited aeration. Exemplary anaerobic conditions have been described previously and are well-known in the art. Exemplary aerobic and anaerobic conditions are described, for example, in United State publication 2009/0047719, filed Aug. 10, 2007. Fermentations can be performed in a batch, fed-batch or continuous manner, as disclosed herein.

If desired, the pH of the medium can be maintained at a desired pH, in particular neutral pH, such as a pH of around 7 by addition of a base, such as NaOH or other bases, or acid, as needed to maintain the culture medium at a desirable pH. The growth rate can be determined by measuring optical density using a spectrophotometer (600 nm), and the glucose uptake rate by monitoring carbon source depletion over time.

The growth medium can include, for example, any carbohydrate source which can supply a source of carbon to the non-naturally occurring microorganism. Such sources include, for example, sugars such as glucose, xylose, arabinose, galactose, mannose, fructose, sucrose and starch. Other sources of carbohydrate include, for example, renewable feedstocks and biomass. Exemplary types of biomasses that can be used as feedstocks in the methods of the invention include cellulosic biomass, hemicellulosic biomass and lignin feedstocks or portions of feedstocks. Such biomass feedstocks contain, for example, carbohydrate substrates useful as carbon sources such as glucose, xylose, arabinose, galactose, mannose, fructose and starch. Given the teachings and guidance provided herein, those skilled in the art will understand that renewable feedstocks and biomass other than those exemplified above also can be used for culturing the microbial organisms of the invention for the production of butadiene.

In addition to renewable feedstocks such as those exemplified above, the butadiene microbial organisms of the invention also can be modified for growth on syngas as its source of carbon. In this specific embodiment, one or more proteins or enzymes are expressed in the butadiene producing organisms to provide a metabolic pathway for utilization of syngas or other gaseous carbon source.

Synthesis gas, also known as syngas or producer gas, is the major product of gasification of coal and of carbonaceous materials such as biomass materials, including agricultural crops and residues. Syngas is a mixture primarily of $H_2$ and CO and can be obtained from the gasification of any organic feedstock, including but not limited to coal, coal oil, natural gas, biomass, and waste organic matter. Gasification is generally carried out under a high fuel to oxygen ratio. Although largely $H_2$ and CO, syngas can also include $CO_2$ and other gases in smaller quantities. Thus, synthesis gas provides a cost effective source of gaseous carbon such as CO and, additionally, $CO_2$.

The Wood-Ljungdahl pathway catalyzes the conversion of CO and $H_2$ to acetyl-CoA and other products such as acetate. Organisms capable of utilizing CO and syngas also generally have the capability of utilizing $CO_2$ and $CO_2/H_2$ mixtures through the same basic set of enzymes and transformations encompassed by the Wood-Ljungdahl pathway. $H_2$-dependent conversion of $CO_2$ to acetate by microorganisms was recognized long before it was revealed that CO also could be used by the same organisms and that the same pathways were involved. Many acetogens have been shown to grow in the presence of $CO_2$ and produce compounds such as acetate as long as hydrogen is present to supply the necessary reducing equivalents (see for example, Drake, *Acetogenesis*, pp. 3-60 Chapman and Hall, New York, (1994)). This can be summarized by the following equation:

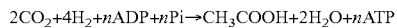

$$2CO_2 + 4H_2 + nADP + nPi \rightarrow CH_3COOH + 2H_2O + nATP$$

Hence, non-naturally occurring microorganisms possessing the Wood-Ljungdahl pathway can utilize $CO_2$ and $H_2$ mixtures as well for the production of acetyl-CoA and other desired products.

The Wood-Ljungdahl pathway is well known in the art and consists of 12 reactions which can be separated into two branches: (1) methyl branch and (2) carbonyl branch. The methyl branch converts syngas to methyl-tetrahydrofolate (methyl-THF) whereas the carbonyl branch converts methyl-THF to acetyl-CoA. The reactions in the methyl branch are catalyzed in order by the following enzymes or proteins: ferredoxin oxidoreductase, formate dehydrogenase, formyltetrahydrofolate synthetase, methenyltetrahydrofolate cyclodehydratase, methylenetetrahydrofolate dehydrogenase and methylenetetrahydrofolate reductase. The reactions in the carbonyl branch are catalyzed in order by the following enzymes or proteins: methyltetrahydrofolate:corrinoid protein methyltransferase (for example, AcsE), corrinoid iron-sulfur protein, nickel-protein assembly protein (for example, AcsF), ferredoxin, acetyl-CoA synthase, carbon monoxide dehydrogenase and nickel-protein assembly protein (for example, CooC). Following the teachings and guidance provided herein for introducing a sufficient number of encoding nucleic acids to generate a butadiene pathway, those skilled in the art will understand that the same engineering design also can be performed with respect to introducing at least the nucleic acids encoding the Wood-Ljungdahl enzymes or proteins absent in the host organism. Therefore, introduction of one or more encoding nucleic acids into the microbial organisms of the invention such that the modified organism contains the complete Wood-Ljungdahl pathway will confer syngas utilization ability.

Additionally, the reductive (reverse) tricarboxylic acid cycle coupled with carbon monoxide dehydrogenase and/or hydrogenase activities can also be used for the conversion of CO, $CO_2$ and/or $H_2$ to acetyl-CoA and other products such as acetate. Organisms capable of fixing carbon via the reductive TCA pathway can utilize one or more of the following enzymes: ATP citrate-lyase, citrate lyase, aconitase, isocitrate dehydrogenase, alpha-ketoglutarate:ferredoxin oxidoreductase, succinyl-CoA synthetase, succinyl-CoA transferase, fumarate reductase, fumarase, malate dehydrogenase, NAD(P)H:ferredoxin oxidoreductase, carbon monoxide dehydrogenase, and hydrogenase. Specifically, the reducing equivalents extracted from CO and/or $H_2$ by carbon monoxide dehydrogenase and hydrogenase are utilized to fix $CO_2$ via the reductive TCA cycle into acetyl-CoA or acetate. Acetate can be converted to acetyl-CoA by enzymes such as acetyl-CoA transferase, acetate kinase/phosphotransacetylase, and acetyl-CoA synthetase. Acetyl-CoA can be converted to the butadiene, glyceraldehyde-3-phosphate, phosphoenolpyruvate, and pyruvate, by pyruvate:ferredoxin oxidoreductase and the enzymes of gluconeogenesis. Following the teachings and guidance provided herein for introducing a sufficient number of encoding nucleic acids to generate a butadiene pathway, those skilled in the art will understand that the same engineering design also can be performed with respect to introducing at least the nucleic acids encoding the reductive TCA pathway enzymes or proteins absent in the host organism. Therefore, introduction of one or more encoding nucleic acids into the microbial organisms of the invention such that the modified organism contains the complete reductive TCA pathway will confer syngas utilization ability.

Accordingly, given the teachings and guidance provided herein, those skilled in the art will understand that a non-naturally occurring microbial organism can be produced that secretes the biosynthesized compounds of the invention when grown on a carbon source such as a carbohydrate. Such compounds include, for example, butadiene and any of the intermediate metabolites in the butadiene pathway. All that is required is to engineer in one or more of the required enzyme or protein activities to achieve biosynthesis of the desired compound or intermediate including, for example, inclusion of some or all of the butadiene biosynthetic pathways. Accordingly, the invention provides a non-naturally occurring microbial organism that produces and/or secretes butadiene when grown on a carbohydrate or other carbon source and produces and/or secretes any of the intermediate metabolites shown in the butadiene pathway when grown on a carbohydrate or other carbon source. The butadiene producing microbial organisms of the invention can initiate synthesis from an intermediate, for example, acetoacetyl-CoA, 3-hydroxybutyryl-CoA, crotonyl-CoA, crotonaldehyde, crotyl alcohol, 2-betenyl-phosphate, 2-butenyl-4-diphosphate, erythritol-4-phosphate, 4-(cytidine 5'-diphospho)-erythritol, 2-phospho-4-(cytidine 5'-diphospho)-erythritol, erythritol-2, 4-cyclodiphosphate, 1-hydroxy-2-butenyl 4-diphosphate, butenyl 4-diphosphate, 2-butenyl 4-diphosphate, 3-oxoglutaryl-CoA, 3-hydroxyglutaryl-CoA, 3-hydroxy-5-oxopentanoate, 3,5-dihydroxy pentanoate, 3-hydroxy-5-phosphonatooxypentanoate, 3-hydroxy-5-[hydroxy(phosphonooxy)phosphoryl]oxy pentanoate, crotonate, erythrose, erythritol, 3,5-dioxopentanoate or 5-hydroxy-3-oxopentanoate.

The non-naturally occurring microbial organisms of the invention are constructed using methods well known in the art as exemplified herein to exogenously express at least one nucleic acid encoding a butadiene pathway enzyme or protein in sufficient amounts to produce butadiene. It is understood that the microbial organisms of the invention are cultured under conditions sufficient to produce butadiene. Following the teachings and guidance provided herein, the non-naturally occurring microbial organisms of the invention can achieve biosynthesis of butadiene resulting in intracellular concentrations between about 0.001-2000 mM or more. Generally, the intracellular concentration of butadiene is between about 3-1500 mM, particularly between about 5-1250 mM and more particularly between about 8-1000 mM, including about 10 mM, 100 mM, 200 mM, 500 mM, 800 mM, or more. Intracellular concentrations between and above each of these exemplary ranges also can be achieved from the non-naturally occurring microbial organisms of the invention.

In some embodiments, culture conditions include anaerobic or substantially anaerobic growth or maintenance conditions. Exemplary anaerobic conditions have been described previously and are well known in the art. Exemplary anaerobic conditions for fermentation processes are described herein and are described, for example, in U.S. publication 2009/0047719, filed Aug. 10, 2007. Any of these conditions can be employed with the non-naturally occurring microbial organisms as well as other anaerobic conditions well known in the art. Under such anaerobic or substantially anaerobic conditions, the butadiene producers can synthesize butadiene at intracellular concentrations of 5-10 mM or more as well as all other concentrations exemplified herein. It is understood that, even though the above description refers to intracellular concentrations, butadiene producing microbial organisms can produce butadiene intracellularly and/or secrete the product into the culture medium.

In some embodiments, the carbon feedstock and other cellular uptake sources such as phosphate, ammonia, sulfate, chloride and other halogens can be chosen to alter the isotopic distribution of the atoms present in butadiene or any butadiene pathway intermediate. The various carbon feedstock and other uptake sources enumerated above will be referred to herein, collectively, as "uptake sources." Uptake sources can provide isotopic enrichment for any atom present in the product butadiene or butadiene pathway intermediate including any butadiene impurities generated in diverging away from the pathway at any point. Isotopic enrichment can be achieved for any target atom including, for example, carbon, hydrogen, oxygen, nitrogen, sulfur, phosphorus, chloride or other halogens.

In some embodiments, the uptake sources can be selected to alter the carbon-12, carbon-13, and carbon-14 ratios. In some embodiments, the uptake sources can be selected to alter the oxygen-16, oxygen-17, and oxygen-18 ratios. In some embodiments, the uptake sources can be selected to alter the hydrogen, deuterium, and tritium ratios. In some embodiments, the uptake sources can be selected to alter the nitrogen-14 and nitrogen-15 ratios. In some embodiments, the uptake sources can be selected to alter the sulfur-32, sulfur-33, sulfur-34, and sulfur-35 ratios. In some embodiments, the uptake sources can be selected to alter the phosphorus-31, phosphorus-32, and phosphorus-33 ratios. In some embodiments, the uptake sources can be selected to alter the chlorine-35, chlorine-36, and chlorine-37 ratios.

In some embodiments, a target isotopic ratio of an uptake source can be obtained via synthetic chemical enrichment of the uptake source. Such isotopically enriched uptake sources can be purchased commercially or prepared in the laboratory. In some embodiments, a target isotopic ratio of an uptake source can be obtained by choice of origin of the uptake source in nature. In some such embodiments, a source of carbon, for example, can be selected from a fossil fuel-derived carbon source, which can be relatively depleted of carbon-14, or an environmental carbon source, such as $CO_2$, which can possess a larger amount of carbon-14 than its petroleum-derived counterpart.

The unstable carbon isotope carbon-14 or radiocarbon makes up for roughly 1 in $10^{12}$ carbon atoms in earth's atmosphere. Carbon-14 has a half-life of about 5700 years. The stock is replenished in the upper atmosphere by a nuclear reaction involving cosmic rays and ordinary nitrogen ($^{14}N$). Fossil fuels contain no carbon-14, as it decayed long ago. Burning fossil fuels should lower the atmospheric carbon-14 fraction (the 'Suess effect'). Indeed, atmospheric carbon-14, measured on tree rings, dropped by 2 to 2.5% from about 1850 to 1954, when nuclear bomb tests started to inject carbon-14 into the atmosphere.

ASTM D6866 was developed in the United States as a standardized analytical method for determining the biobased content of solid, liquid, and gaseous samples using radiocarbon dating. Specifically, ASTM D6866 was developed at the request of the United States Department of Agriculture to satisfy legislation requiring federal agencies to give preference in procurement to manufacturers using the greatest amount of biomass in their products (per the Farm Security and Rural Investment Act of 2002). It was quickly established that radiocarbon dating was the only viable and accurate technique to use for the determination of a product's biobased content. A working standard of radiocarbon dating for industrial use was completed in 2004 and is now cited in US Federal Law (7 CFR part 2902). ASTM D6866 was first published in 2004. There have been several versions released since then. The current active version of the standard is ASTM D6866-11 effective Apr. 1, 2011.

Isotopic enrichment is readily assessed by mass spectrometry using techniques known in the art such as Stable Isotope Ratio Mass Spectrometry (SIRMS) and Site-Specific Natural Isotopic Fractionation by Nuclear Magnetic Resonance (SNIF-NMR). Such mass spectral techniques can be integrated with separation techniques such as liquid chromatography (LC) and/or high performance liquid chromatography (HPLC).

The biobased content of monomers (i.e., Fm or fraction modern) is estimated by the ratio of carbon-14 ($^{14}C$) to carbon-12 ($^{12}C$) measured by accelerator mass spectrometry (AMS). Specifically, the Fraction Modern (Fm) is computed from the expression: Fm=(S−B)/(M−B), where B, S and M represent the $^{14}C/^{12}C$ ratios of the blank, the sample and the modern reference, respectively. Fraction Modern is a measurement of the deviation of the $^{14}C/^{12}C$ ratio of a sample from "Modern." Modern is defined as 95% of the radiocarbon concentration (in AD 1950) of NBS Oxalic Acid I (i.e., SRM 4990b) normalized to $\delta^{13}C_{VPDB}$=−19 per mil. Olsson, *The use of Oxalic acid as a Standard*. In, *Radiocarbon Variations and Absolute Chronology*, Nobel Symposium, 12th Proc., John Wiley & Sons, New York (1970). AMS results are calculated using the internationally agreed upon definition of 0.95 times the specific activity of NBS Oxalic Acid I (SRM 4990b) normalized to $\delta^{13}C_{VPDB}$=−19 per mil. This is equivalent to an absolute (AD 1950) $^{14}C/^{12}C$ ratio of 1.176±0.010× $10^{-12}$. Karlen et al., *Arkiv Geofysik*, 4:465-471 (1968).

An oxalic acid standard (SRM 4990b or HOx 1) was made from a crop of 1955 sugar beet. Although there were 1000 lbs made, this oxalic acid standard is no longer commercially available. Another standard, Oxalic Acid II, was prepared when stocks of SRM 4990b began to dwindle. The Oxalic Acid II standard (HOx 2; N.I.S.T designation SRM 4990 C) was made from a crop of 1977 French beet molasses. In the early 1980's, a group of 12 laboratories measured the ratios of the two standards. The ratio of the activity of Oxalic acid II to 1 is 1.2933±0.001 (the weighted mean). Mann, *Radiocarbon*, 25(2):519-527 (1983). The isotopic ratio of HOx II is −17.8 per mille. ASTM D6866-11 suggests use of SRM 4990 C for the modern standard. A Fm=0% represents the entire lack of carbon-14 atoms in a material thus indicating a fossil (for example, petroleum based) carbon source. A Fm=100%, after correction for the post-1950 bomb injection of carbon-14 into the atmosphere, likewise indicates an entirely modern carbon source.

As described in ASTM D6866, the percent modern carbon (pMC) can be greater than 100% because of the continuing but diminishing effects of the 1950s nuclear testing programs, which resulted in a considerable enrichment of carbon-14 in the atmosphere as described in ASTM D6866-11. Because all sample carbon-14 activities are referenced to a "pre-bomb" standard, and because nearly all new biobased products are produced in a post-bomb environment, all pMC values (after correction for isotopic fraction) must be multiplied by 0.95 (as of 2010) to better reflect the true biobased content of the sample. A biobased content that is greater than 103% suggests that either an analytical error has occurred, or that the source of biobased carbon is more than several years old.

ASTM D6866 quantifies the biobased content relative to the material's total organic content and does not consider the inorganic carbon and other non-carbon containing substances present. To illustrate, below are some exemplary formulations and their corresponding ASTM D6866 results:

Product 1—liquid with 50% starch-based material and 50% water. Biobased Content=100% (product 1 has 50% organic content and 100% of that fraction is biobased);

Product 2—liquid with 50% starch-based material, 25% petroleum-based, 25% water. Biobased Content=66.7% (product 2 has 75% organic content but only 50% of that fraction is biobased);

Product 3—solid that is 50% glass and 50% polyethylene from petroleum. Biobased Content=0% (product 3 has 50% organic carbon but from fossil sources; glass is not carbon-containing);

Product 4—solid that is 50% glass and 50% polyethylene from biomass. Biobased Content=100% (product 4 has 50% organic carbon and 100% of it is renewable); and Product 5—liquid with 50% soy-based material, 30% petroleum-based, 10% water, and 10% inorganic substances. Biobased Content=62.5% (product 5 has 80% organic carbon but only 50% of it is renewable).

Applications of carbon-14 dating techniques to quantify bio-based content of renewable materials are known in the art. Currie et al., *Nuclear Instruments and Methods in Physics Research B*, 172:281-287 (2000). For example, carbon-14 dating has been used to quantify bio-based content in terephthalate-containing materials. Colonna et al., *Green Chemistry*, 13:2543-2548 (2011). Notably, polypropylene terephthalate (PPT) polymers derived from renewable 1,3-propanediol and petroleum-derived terephthalic acid resulted in Fm values near 30% (i.e., since 3/11 of the polymeric carbon derives from renewable 1,3-propanediol and 8/11 from the fossil end member terephthalic acid). Currie et al., supra. In contrast, polybutylene terephthalate polymer derived from both renewable 1,4-butanediol and renewable terephthalic acid resulted in bio-based content exceeding 90%. Colonna et al., supra.

Accordingly, in some embodiments, the present invention provides butadiene or a butadiene intermediate that has a carbon-12, carbon-13, and carbon-14 ratio that reflects an atmospheric carbon uptake source. For example, in some aspects the butadiene or a butadiene intermediate can have an Fm value of at least 60%, at least 65%, at least 70%, at least 75%, at least 80%, at least 85%, at least 90%, at least 95%, at least 98 or at much as 100%. In some such embodiments, the uptake source is $CO_2$. In some embodiments, the present invention provides butadiene or a butadiene intermediate that has a carbon-12, carbon-13, and carbon-14 ratio that reflects petroleum-based carbon uptake source. In this aspect, the butadiene or a butadiene intermediate can have an Fm value of less than 10%, less than 5%, less than 2% or less than 1%. In some embodiments, the present invention provides butadiene or a butadiene intermediate that has a carbon-12, carbon-13, and carbon-14 ratio that is obtained by a combination of an atmospheric carbon uptake source with a petroleum-based uptake source. Such combination of uptake sources is one means by which the carbon-12, carbon-13, and carbon-14 ratio can be varied.

In addition to the culturing and fermentation conditions disclosed herein, growth condition for achieving biosynthesis of butadiene can include the addition of an osmoprotectant to the culturing conditions. In certain embodiments, the non-naturally occurring microbial organisms of the invention can be sustained, cultured or fermented as described herein in the presence of an osmoprotectant. Briefly, an osmoprotectant refers to a compound that acts as an osmolyte and helps a microbial organism as described herein survive osmotic stress. Osmoprotectants include, but are not limited to, betaines, amino acids, and the sugar trehalose. Non-limiting examples of such are glycine betaine, praline betaine, dimethylthetin, dimethylslfonioproprionate, 3-dimethylsulfonio-2-methylproprionate, pipecolic acid, dimethylsulfonioacetate, choline, L-carnitine and ectoine. In one aspect, the osmoprotectant is glycine betaine. It is understood to one of ordinary skill in the art that the amount and type of osmoprotectant suitable for protecting a microbial organism described herein from osmotic stress will depend on the microbial organism used. The amount of osmoprotectant in the culturing conditions can be, for example, no more than about 0.1 mM, no more than about 0.5 mM, no more than about 1.0 mM, no more than about 1.5 mM, no more than about 2.0 mM, no more than about 2.5 mM, no more than about 3.0 mM, no more than about 5.0 mM, no more than about 7.0 mM, no more than about 10 mM, no more than about 50 mM, no more than about 100 mM or no more than about 500 mM.

The culture conditions can include, for example, liquid culture procedures as well as fermentation and other large scale culture procedures. As described herein, particularly useful yields of the biosynthetic products of the invention can be obtained under anaerobic or substantially anaerobic culture conditions.

As described herein, one exemplary growth condition for achieving biosynthesis of butadiene includes anaerobic culture or fermentation conditions. In certain embodiments, the non-naturally occurring microbial organisms of the invention can be sustained, cultured or fermented under anaerobic or substantially anaerobic conditions. Briefly, anaerobic conditions refers to an environment devoid of oxygen. Substantially anaerobic conditions include, for example, a culture, batch fermentation or continuous fermentation such that the dissolved oxygen concentration in the medium remains between 0 and 10% of saturation. Substantially anaerobic conditions also includes growing or resting cells in liquid medium or on solid agar inside a sealed chamber maintained with an atmosphere of less than 1% oxygen. The percent of oxygen can be maintained by, for example, sparging the culture with an $N_2/CO_2$ mixture or other suitable non-oxygen gas or gases.

The culture conditions described herein can be scaled up and grown continuously for manufacturing of butadiene. Exemplary growth procedures include, for example, fed-batch fermentation and batch separation; fed-batch fermentation and continuous separation, or continuous fermentation and continuous separation. All of these processes are well known in the art. Fermentation procedures are particularly useful for the biosynthetic production of commercial quantities of butadiene. Generally, and as with non-continuous culture procedures, the continuous and/or near-continuous production of butadiene will include culturing a non-naturally occurring butadiene producing organism of the invention in sufficient nutrients and medium to sustain and/or nearly sustain growth in an exponential phase. Continuous culture under such conditions can be include, for example, growth for 1 day, 2, 3, 4, 5, 6 or 7 days or more. Additionally, continuous culture can include longer time periods of 1 week, 2, 3, 4 or 5 or more weeks and up to several months. Alternatively, organisms of the invention can be cultured for hours, if suitable for a particular application. It is to be understood that the continuous and/or near-continuous culture conditions also can include all time intervals in between these exemplary periods. It is further understood that the time of culturing the microbial organism of the invention is for a sufficient period of time to produce a sufficient amount of product for a desired purpose.

Fermentation procedures are well known in the art. Briefly, fermentation for the biosynthetic production of butadiene can be utilized in, for example, fed-batch fermentation and batch separation; fed-batch fermentation and continuous separation, or continuous fermentation and continuous separation. Examples of batch and continuous fermentation procedures are well known in the art.

In addition to the above fermentation procedures using the butadiene producers of the invention for continuous production of substantial quantities of butadiene, the butadiene producers also can be, for example, simultaneously subjected to chemical synthesis procedures to convert the product to other compounds or the product can be separated from the fermentation culture and sequentially subjected to chemical or enzymatic conversion to convert the product to other compounds, if desired.

To generate better producers, metabolic modeling can be utilized to optimize growth conditions. Modeling can also be used to design gene knockouts that additionally optimize utilization of the pathway (see, for example, U.S. patent publications US 2002/0012939, US 2003/0224363, US 2004/0029149, US 2004/0072723, US 2003/0059792, US 2002/0168654 and US 2004/0009466, and U.S. Pat. No. 7,127,379). Modeling analysis allows reliable predictions of the effects on cell growth of shifting the metabolism towards more efficient production of butadiene.

One computational method for identifying and designing metabolic alterations favoring biosynthesis of a desired product is the OptKnock computational framework (Burgard et al., *Biotechnol. Bioeng.* 84:647-657 (2003)). OptKnock is a metabolic modeling and simulation program that suggests gene deletion or disruption strategies that result in genetically stable microorganisms which overproduce the target product. Specifically, the framework examines the complete metabolic and/or biochemical network of a microorganism in order to suggest genetic manipulations that force the desired biochemical to become an obligatory byproduct of cell growth. By coupling biochemical production with cell growth through strategically placed gene deletions or other functional gene disruption, the growth selection pressures imposed on the engineered strains after long periods of time in a bioreactor lead to improvements in performance as a result of the compulsory growth-coupled biochemical production. Lastly, when gene deletions are constructed there is a negligible possibility of the designed strains reverting to their wild-type states because the genes selected by OptKnock are to be completely removed from the genome. Therefore, this computational methodology can be used to either identify alternative pathways that lead to biosynthesis of a desired product or used in connection with the non-naturally occurring microbial organisms for further optimization of biosynthesis of a desired product.

Briefly, OptKnock is a term used herein to refer to a computational method and system for modeling cellular metabolism. The OptKnock program relates to a framework of models and methods that incorporate particular constraints into flux balance analysis (FBA) models. These constraints include, for example, qualitative kinetic information, qualitative regulatory information, and/or DNA microarray experimental data. OptKnock also computes solutions to various metabolic problems by, for example, tightening the flux boundaries derived through flux balance models and subsequently probing the performance limits of metabolic networks in the presence of gene additions or deletions. OptKnock computational framework allows the construction of model formulations that allow an effective query of the performance limits of metabolic networks and provides methods for solving the resulting mixed-integer linear programming problems. The metabolic modeling and simulation methods referred to herein as OptKnock are described in, for example, U.S. publication 2002/0168654, filed Jan. 10, 2002, in International Patent No. PCT/US02/00660, filed Jan. 10, 2002, and U.S. publication 2009/0047719, filed Aug. 10, 2007.

Another computational method for identifying and designing metabolic alterations favoring biosynthetic production of a product is a metabolic modeling and simulation system termed SimPheny®. This computational method and system is described in, for example, U.S. publication 2003/0233218, filed Jun. 14, 2002, and in International Patent Application No. PCT/US03/18838, filed Jun. 13, 2003. SimPheny® is a computational system that can be used to produce a network model in silico and to simulate the flux of mass, energy or charge through the chemical reactions of a biological system to define a solution space that contains any and all possible functionalities of the chemical reactions in the system, thereby determining a range of allowed activities for the biological system. This approach is referred to as constraints-based modeling because the solution space is defined by constraints such as the known stoichiometry of the included reactions as well as reaction thermodynamic and capacity constraints associated with maximum fluxes through reactions. The space defined by these constraints can be interrogated to determine the phenotypic capabilities and behavior of the biological system or of its biochemical components.

These computational approaches are consistent with biological realities because biological systems are flexible and can reach the same result in many different ways. Biological systems are designed through evolutionary mechanisms that have been restricted by fundamental constraints that all living systems must face. Therefore, constraints-based modeling strategy embraces these general realities. Further, the ability to continuously impose further restrictions on a network model via the tightening of constraints results in a reduction in the size of the solution space, thereby enhancing the precision with which physiological performance or phenotype can be predicted.

Given the teachings and guidance provided herein, those skilled in the art will be able to apply various computational frameworks for metabolic modeling and simulation to design and implement biosynthesis of a desired compound in host microbial organisms. Such metabolic modeling and simulation methods include, for example, the computational systems exemplified above as SimPheny® and OptKnock. For illustration of the invention, some methods are described herein with reference to the OptKnock computation framework for modeling and simulation. Those skilled in the art will know how to apply the identification, design and implementation of the metabolic alterations using OptKnock to any of such other metabolic modeling and simulation computational frameworks and methods well known in the art.

The methods described above will provide one set of metabolic reactions to disrupt. Elimination of each reaction within the set or metabolic modification can result in a desired product as an obligatory product during the growth phase of the organism. Because the reactions are known, a solution to the bilevel OptKnock problem also will provide the associated gene or genes encoding one or more enzymes that catalyze each reaction within the set of reactions. Identification of a set of reactions and their corresponding genes encoding the enzymes participating in each reaction is generally an automated process, accomplished through correlation of the reactions with a reaction database having a relationship between enzymes and encoding genes.

Once identified, the set of reactions that are to be disrupted in order to achieve production of a desired product are implemented in the target cell or organism by functional disruption of at least one gene encoding each metabolic reaction within the set. One particularly useful means to achieve functional disruption of the reaction set is by deletion of each encoding gene. However, in some instances, it can be beneficial to disrupt the reaction by other genetic aberrations including, for example, mutation, deletion of regulatory regions such as promoters or cis binding sites for regulatory factors, or by truncation of the coding sequence at any of a number of locations. These latter aberrations, resulting in less than total deletion of the gene set can be useful, for example, when rapid assessments of the coupling of a product are desired or when genetic reversion is less likely to occur.

To identify additional productive solutions to the above described bilevel OptKnock problem which lead to further sets of reactions to disrupt or metabolic modifications that can result in the biosynthesis, including growth-coupled biosynthesis of a desired product, an optimization method, termed integer cuts, can be implemented. This method proceeds by iteratively solving the OptKnock problem exemplified above with the incorporation of an additional constraint referred to as an integer cut at each iteration. Integer cut constraints effectively prevent the solution procedure from choosing the exact same set of reactions identified in any previous iteration that obligatorily couples product biosynthesis to growth. For example, if a previously identified growth-coupled metabolic modification specifies reactions 1, 2, and 3 for disruption, then the following constraint prevents the same reactions from being simultaneously considered in subsequent solutions. The integer cut method is well known in the art and can be found described in, for example, Burgard et al., *Biotechnol. Prog.* 17:791-797 (2001). As with all methods described herein with reference to their use in combination with the OptKnock computational framework for metabolic modeling and simulation, the integer cut method of reducing redundancy in iterative computational analysis also can be applied with other computational frameworks well known in the art including, for example, SimPheny®.

The methods exemplified herein allow the construction of cells and organisms that biosynthetically produce a desired product, including the obligatory coupling of production of a target biochemical product to growth of the cell or organism engineered to harbor the identified genetic alterations. Therefore, the computational methods described herein allow the identification and implementation of metabolic modifications that are identified by an in silico method selected from OptKnock or SimPheny®. The set of metabolic modifications can include, for example, addition of one or more biosynthetic pathway enzymes and/or functional disruption of one or more metabolic reactions including, for example, disruption by gene deletion.

As discussed above, the OptKnock methodology was developed on the premise that mutant microbial networks can be evolved towards their computationally predicted maximum-growth phenotypes when subjected to long periods of growth selection. In other words, the approach leverages an organism's ability to self-optimize under selective pressures. The OptKnock framework allows for the exhaustive enumeration of gene deletion combinations that force a coupling between biochemical production and cell growth based on network stoichiometry. The identification of optimal gene/reaction knockouts requires the solution of a bilevel optimization problem that chooses the set of active reactions such that an optimal growth solution for the resulting network overproduces the biochemical of interest (Burgard et al., *Biotechnol. Bioeng.* 84:647-657 (2003)).

An in silico stoichiometric model of *E. coli* metabolism can be employed to identify essential genes for metabolic pathways as exemplified previously and described in, for example, U.S. patent publications US 2002/0012939, US 2003/0224363, US 2004/0029149, US 2004/0072723, US 2003/0059792, US 2002/0168654 and US 2004/0009466, and in U.S. Pat. No. 7,127,379. As disclosed herein, the OptKnock mathematical framework can be applied to pinpoint gene deletions leading to the growth-coupled production of a desired product. Further, the solution of the bilevel OptKnock problem provides only one set of deletions. To enumerate all meaningful solutions, that is, all sets of knockouts leading to growth-coupled production formation, an optimization technique, termed integer cuts, can be implemented. This entails iteratively solving the OptKnock problem with the incorporation of an additional constraint referred to as an integer cut at each iteration, as discussed above.

As disclosed herein, a nucleic acid encoding a desired activity of a butadiene pathway can be introduced into a host organism. In some cases, it can be desirable to modify an activity of a butadiene pathway enzyme or protein to increase production of butadiene. For example, known mutations that increase the activity of a protein or enzyme can be introduced into an encoding nucleic acid molecule. Additionally, optimization methods can be applied to increase the activity of an enzyme or protein and/or decrease an inhibitory activity, for example, decrease the activity of a negative regulator.

One such optimization method is directed evolution. Directed evolution is a powerful approach that involves the introduction of mutations targeted to a specific gene in order to improve and/or alter the properties of an enzyme. Improved and/or altered enzymes can be identified through the development and implementation of sensitive high-throughput screening assays that allow the automated screening of many enzyme variants (for example, $>10^4$). Iterative rounds of mutagenesis and screening typically are performed to afford an enzyme with optimized properties. Computational algorithms that can help to identify areas of the gene for mutagenesis also have been developed and can significantly reduce the number of enzyme variants that need to be generated and screened. Numerous directed evolution technologies have been developed (for reviews, see Hibbert et al., *Biomol. Eng* 22:11-19 (2005); Huisman and Lalonde, In Biocatalysis in the pharmaceutical and biotechnology industries pgs. 717-742 (2007), Patel (ed.), CRC Press; Otten and Quax. *Biomol. Eng* 22:1-9 (2005).; and Sen et al., *Appl Biochem. Biotechnol* 143:212-223 (2007)) to be effective at creating diverse variant libraries, and these methods have been successfully applied to the improvement of a wide range of properties across many enzyme classes. Enzyme characteristics that have been improved and/or altered by directed evolution technologies include, for example: selectivity/specificity, for conversion of non-natural substrates; temperature stability, for robust high temperature processing; pH stability, for bioprocessing under lower or higher pH conditions; substrate or product tolerance, so that high product titers can be achieved; binding ($K_m$), including broadening substrate binding to include non-natural substrates; inhibition ($K_i$), to remove inhibition by products, substrates, or key intermediates; activity (kcat), to increases enzymatic reaction rates to achieve desired flux; expression levels, to increase protein yields and overall pathway flux; oxygen stability, for operation of air sensitive enzymes under aerobic conditions; and anaerobic activity, for operation of an aerobic enzyme in the absence of oxygen.

Described below in more detail are exemplary methods that have been developed for the mutagenesis and diversification of genes to target desired properties of specific enzymes. Such methods are well known to those skilled in the art. Any of these can be used to alter and/or optimize the activity of a butadiene pathway enzyme or protein.

EpPCR (Pritchard et al., *J Theor. Biol.* 234:497-509 (2005)) introduces random point mutations by reducing the fidelity of DNA polymerase in PCR reactions by the addition of $Mn^{2+}$ ions, by biasing dNTP concentrations, or by other conditional variations. The five step cloning process to confine the mutagenesis to the target gene of interest involves: 1) error-prone PCR amplification of the gene of interest; 2) restriction enzyme digestion; 3) gel purification of the desired DNA fragment; 4) ligation into a vector; 5) transformation of the gene variants into a suitable host and screening of the library for improved performance. This method can generate multiple mutations in a single gene simultaneously, which can be useful to screen a larger number of potential variants having a desired activity. A high number of mutants can be generated by EpPCR, so a high-throughput screening assay or a selection method, for example, using robotics, is useful to identify those with desirable characteristics.

Error-prone Rolling Circle Amplification (epRCA) (Fujii et al., *Nucleic Acids Res.* 32:e145 (2004); and Fujii et al., *Nat. Protoc.* 1:2493-2497 (2006)) has many of the same elements as epPCR except a whole circular plasmid is used as the template and random 6-mers with exonuclease resistant thiophosphate linkages on the last 2 nucleotides are used to amplify the plasmid followed by transformation into cells in which the plasmid is re-circularized at tandem repeats. Adjusting the $Mn^{2+}$ concentration can vary the mutation rate somewhat. This technique uses a simple error-prone, single-step method to create a full copy of the plasmid with 3-4 mutations/kbp. No restriction enzyme digestion or specific primers are required. Additionally, this method is typically available as a commercially available kit.

DNA or Family Shuffling (Stemmer, *Proc Natl Acad Sci USA* 91:10747-10751 (1994)); and Stemmer, *Nature* 370:389-391 (1994)) typically involves digestion of two or more variant genes with nucleases such as Dnase I or EndoV to generate a pool of random fragments that are reassembled by cycles of annealing and extension in the presence of DNA polymerase to create a library of chimeric genes. Fragments prime each other and recombination occurs when one copy primes another copy (template switch). This method can be used with >1 kbp DNA sequences. In addition to mutational recombinants created by fragment reassembly, this method introduces point mutations in the extension steps at a rate similar to error-prone PCR. The method can be used to remove deleterious, random and neutral mutations.

Staggered Extension (StEP) (Zhao et al., *Nat. Biotechnol.* 16:258-261 (1998)) entails template priming followed by repeated cycles of 2 step PCR with denaturation and very short duration of annealing/extension (as short as 5 sec). Growing fragments anneal to different templates and extend further, which is repeated until full-length sequences are made. Template switching means most resulting fragments have multiple parents. Combinations of low-fidelity polymerases (Taq and Mutazyme) reduce error-prone biases because of opposite mutational spectra.

In Random Priming Recombination (RPR) random sequence primers are used to generate many short DNA fragments complementary to different segments of the template (Shao et al., *Nucleic Acids Res* 26:681-683 (1998)). Base misincorporation and mispriming via epPCR give point mutations. Short DNA fragments prime one another based on homology and are recombined and reassembled into full-length by repeated thermocycling. Removal of templates prior to this step assures low parental recombinants. This method, like most others, can be performed over multiple iterations to evolve distinct properties. This technology avoids sequence bias, is independent of gene length, and requires very little parent DNA for the application.

In Heteroduplex Recombination linearized plasmid DNA is used to form heteroduplexes that are repaired by mismatch repair (Volkov et al, *Nucleic Acids Res.* 27:e18 (1999); and Volkov et al., *Methods Enzymol.* 328:456-463 (2000)). The mismatch repair step is at least somewhat mutagenic. Heteroduplexes transform more efficiently than linear homoduplexes. This method is suitable for large genes and whole operons.

Random Chimeragenesis on Transient Templates (RA-CHITT) (Coco et al., Nat. Biotechnol. 19:354-359 (2001)) employs Dnase I fragmentation and size fractionation of single stranded DNA (ssDNA). Homologous fragments are hybridized in the absence of polymerase to a complementary ssDNA scaffold. Any overlapping unhybridized fragment ends are trimmed down by an exonuclease. Gaps between fragments are filled in and then ligated to give a pool of full-length diverse strands hybridized to the scaffold, which contains U to preclude amplification. The scaffold then is destroyed and is replaced by a new strand complementary to the diverse strand by PCR amplification. The method involves one strand (scaffold) that is from only one parent while the priming fragments derive from other genes, and the parent scaffold is selected against. Thus, no reannealing with parental fragments occurs. Overlapping fragments are trimmed with an exonuclease. Otherwise, this is conceptually similar to DNA shuffling and StEP. Therefore, there should be no siblings, few inactives, and no unshuffled parentals. This technique has advantages in that few or no parental genes are created and many more crossovers can result relative to standard DNA shuffling.

Recombined Extension on Truncated templates (RETT) entails template switching of unidirectionally growing strands from primers in the presence of unidirectional ssDNA fragments used as a pool of templates (Lee et al., J. Molec. Catalysis 26:119-129 (2003)). No DNA endonucleases are used. Unidirectional ssDNA is made by DNA polymerase with random primers or serial deletion with exonuclease. Unidirectional ssDNA are only templates and not primers. Random priming and exonucleases do not introduce sequence bias as true of enzymatic cleavage of DNA shuffling/RACHITT. RETT can be easier to optimize than StEP because it uses normal PCR conditions instead of very short extensions. Recombination occurs as a component of the PCR steps, that is, no direct shuffling. This method can also be more random than StEP due to the absence of pauses.

In Degenerate Oligonucleotide Gene Shuffling (DOGS) degenerate primers are used to control recombination between molecules; (Bergquist and Gibbs, Methods Mol. Biol. 352:191-204 (2007); Bergquist et al., Biomol. Eng 22:63-72 (2005); Gibbs et al., Gene 271:13-20 (2001)) this can be used to control the tendency of other methods such as DNA shuffling to regenerate parental genes. This method can be combined with random mutagenesis (epPCR) of selected gene segments. This can be a good method to block the reformation of parental sequences. No endonucleases are needed. By adjusting input concentrations of segments made, one can bias towards a desired backbone. This method allows DNA shuffling from unrelated parents without restriction enzyme digests and allows a choice of random mutagenesis methods.

Incremental Truncation for the Creation of Hybrid Enzymes (ITCHY) creates a combinatorial library with 1 base pair deletions of a gene or gene fragment of interest (Ostermeier et al., Proc. Natl. Acad. Sci. USA 96:3562-3567 (1999); and Ostermeier et al., Nat. Biotechnol. 17:1205-1209 (1999)). Truncations are introduced in opposite direction on pieces of 2 different genes. These are ligated together and the fusions are cloned. This technique does not require homology between the 2 parental genes. When ITCHY is combined with DNA shuffling, the system is called SCRATCHY (see below). A major advantage of both is no need for homology between parental genes; for example, functional fusions between an *E. coli* and a human gene were created via ITCHY. When ITCHY libraries are made, all possible crossovers are captured.

Thio-Incremental Truncation for the Creation of Hybrid Enzymes (THIO-ITCHY) is similar to ITCHY except that phosphothioate dNTPs are used to generate truncations (Lutz et al., Nucleic Acids Res 29:E16 (2001)). Relative to ITCHY, THIO-ITCHY can be easier to optimize, provide more reproducibility, and adjustability.

SCRATCHY combines two methods for recombining genes, ITCHY and DNA shuffling (Lutz et al., Proc. Natl. Acad. Sci. USA 98:11248-11253 (2001)). SCRATCHY combines the best features of ITCHY and DNA shuffling. First, ITCHY is used to create a comprehensive set of fusions between fragments of genes in a DNA homology-independent fashion. This artificial family is then subjected to a DNA-shuffling step to augment the number of crossovers. Computational predictions can be used in optimization. SCRATCHY is more effective than DNA shuffling when sequence identity is below 80%.

In Random Drift Mutagenesis (RNDM) mutations are made via epPCR followed by screening/selection for those retaining usable activity (Bergquist et al., Biomol. Eng. 22:63-72 (2005)). Then, these are used in DOGS to generate recombinants with fusions between multiple active mutants or between active mutants and some other desirable parent. Designed to promote isolation of neutral mutations; its purpose is to screen for retained catalytic activity whether or not this activity is higher or lower than in the original gene. RNDM is usable in high throughput assays when screening is capable of detecting activity above background. RNDM has been used as a front end to DOGS in generating diversity. The technique imposes a requirement for activity prior to shuffling or other subsequent steps; neutral drift libraries are indicated to result in higher/quicker improvements in activity from smaller libraries. Though published using epPCR, this could be applied to other large-scale mutagenesis methods.

Sequence Saturation Mutagenesis (SeSaM) is a random mutagenesis method that: 1) generates a pool of random length fragments using random incorporation of a phosphothioate nucleotide and cleavage; this pool is used as a template to 2) extend in the presence of "universal" bases such as inosine; 3) replication of an inosine-containing complement gives random base incorporation and, consequently, mutagenesis (Wong et al., Biotechnol. J. 3:74-82 (2008); Wong et al., Nucleic Acids Res. 32:e26 (2004); and Wong et al., Anal. Biochem. 341:187-189 (2005)). Using this technique it can be possible to generate a large library of mutants within 2 to 3 days using simple methods. This technique is non-directed in comparison to the mutational bias of DNA polymerases. Differences in this approach makes this technique complementary (or an alternative) to epPCR.

In Synthetic Shuffling, overlapping oligonucleotides are designed to encode "all genetic diversity in targets" and allow a very high diversity for the shuffled progeny (Ness et al., Nat. Biotechnol. 20:1251-1255 (2002)). In this technique, one can design the fragments to be shuffled. This aids in increasing the resulting diversity of the progeny. One can design sequence/codon biases to make more distantly related sequences recombine at rates approaching those observed with more closely related sequences. Additionally, the technique does not require physically possessing the template genes.

Nucleotide Exchange and Excision Technology NexT exploits a combination of dUTP incorporation followed by treatment with uracil DNA glycosylase and then piperidine to perform endpoint DNA fragmentation (Muller et al., Nucleic Acids Res. 33:e117 (2005)). The gene is reassembled using internal PCR primer extension with proofreading polymerase. The sizes for shuffling are directly controllable using varying dUPT::dTTP ratios. This is an end point reaction using simple methods for uracil incorporation and cleavage. Other nucleotide analogs, such as 8-oxo-guanine, can be used with this method. Additionally, the technique works well with very short fragments (86 bp) and has a low error rate. The chemical cleavage of DNA used in this technique results in very few unshuffled clones.

In Sequence Homology-Independent Protein Recombination (SHIPREC), a linker is used to facilitate fusion between two distantly related or unrelated genes. Nuclease treatment is used to generate a range of chimeras between the two genes. These fusions result in libraries of single-crossover hybrids (Sieber et al., Nat. Biotechnol. 19:456-460 (2001)). This produces a limited type of shuffling and a separate process is required for mutagenesis. In addition, since no homology is needed, this technique can create a library of chimeras with varying fractions of each of the two unrelated parent genes. SHIPREC was tested with a heme-binding domain of a bacterial CP450 fused to N-terminal regions of a mammalian CP450; this produced mammalian activity in a more soluble enzyme.

In Gene Site Saturation Mutagenesis™ (GSSM™) the starting materials are a supercoiled dsDNA plasmid containing an insert and two primers which are degenerate at the desired site of mutations (Kretz et al., Methods Enzymol. 388:3-11 (2004)). Primers carrying the mutation of interest, anneal to the same sequence on opposite strands of DNA. The mutation is typically in the middle of the primer and flanked on each side by approximately 20 nucleotides of correct sequence. The sequence in the primer is NNN or NNK (coding) and MNN (noncoding) (N=all 4, K=G, T, M=A, C). After extension, DpnI is used to digest dam-methylated DNA to eliminate the wild-type template. This technique explores all possible amino acid substitutions at a given locus (that is, one codon). The technique facilitates the generation of all possible replacements at a single-site with no nonsense codons and results in equal to near-equal representation of most possible alleles. This technique does not require prior knowledge of the structure, mechanism, or domains of the target enzyme. If followed by shuffling or Gene Reassembly, this technology creates a diverse library of recombinants containing all possible combinations of single-site up-mutations. The usefulness of this technology combination has been demonstrated for the successful evolution of over 50 different enzymes, and also for more than one property in a given enzyme.

Combinatorial Cassette Mutagenesis (CCM) involves the use of short oligonucleotide cassettes to replace limited regions with a large number of possible amino acid sequence alterations (Reidhaar-Olson et al. Methods Enzymol. 208: 564-586 (1991); and Reidhaar-Olson et al. Science 241:53-57 (1988)). Simultaneous substitutions at two or three sites are possible using this technique. Additionally, the method tests a large multiplicity of possible sequence changes at a limited range of sites. This technique has been used to explore the information content of the lambda repressor DNA-binding domain.

Combinatorial Multiple Cassette Mutagenesis (CMCM) is essentially similar to CCM except it is employed as part of a larger program: 1) use of epPCR at high mutation rate to 2) identify hot spots and hot regions and then 3) extension by CMCM to cover a defined region of protein sequence space (Reetz et al., Angew. Chem. Int. Ed Engl. 40:3589-3591 (2001)). As with CCM, this method can test virtually all possible alterations over a target region. If used along with methods to create random mutations and shuffled genes, it provides an excellent means of generating diverse, shuffled proteins. This approach was successful in increasing, by 51-fold, the enantioselectivity of an enzyme.

In the Mutator Strains technique, conditional ts mutator plasmids allow increases of 20 to 4000-× in random and natural mutation frequency during selection and block accumulation of deleterious mutations when selection is not required (Selifonova et al., Appl. Environ. Microbiol. 67:3645-3649 (2001)). This technology is based on a plasmid-derived mutD5 gene, which encodes a mutant subunit of DNA polymerase III. This subunit binds to endogenous DNA polymerase III and compromises the proofreading ability of polymerase III in any strain that harbors the plasmid. A broad-spectrum of base substitutions and frameshift mutations occur. In order for effective use, the mutator plasmid should be removed once the desired phenotype is achieved; this is accomplished through a temperature sensitive (ts) origin of replication, which allows for plasmid curing at 41° C. It should be noted that mutator strains have been explored for quite some time (see Low et al., J. Mol. Biol. 260:359-3680 (1996)). In this technique, very high spontaneous mutation rates are observed. The conditional property minimizes non-desired background mutations. This technology could be combined with adaptive evolution to enhance mutagenesis rates and more rapidly achieve desired phenotypes.

Look-Through Mutagenesis (LTM) is a multidimensional mutagenesis method that assesses and optimizes combinatorial mutations of selected amino acids (Rajpal et al., Proc. Natl. Acad. Sci. USA 102:8466-8471 (2005)). Rather than saturating each site with all possible amino acid changes, a set of nine is chosen to cover the range of amino acid R-group chemistry. Fewer changes per site allows multiple sites to be subjected to this type of mutagenesis. A >800-fold increase in binding affinity for an antibody from low nanomolar to picomolar has been achieved through this method. This is a rational approach to minimize the number of random combinations and can increase the ability to find improved traits by greatly decreasing the numbers of clones to be screened. This has been applied to antibody engineering, specifically to increase the binding affinity and/or reduce dissociation. The technique can be combined with either screens or selections.

Gene Reassembly is a DNA shuffling method that can be applied to multiple genes at one time or to create a large library of chimeras (multiple mutations) of a single gene (Tunable GeneReassembly™ (TGR™) Technology supplied by Verenium Corporation). Typically this technology is used in combination with ultra-high-throughput screening to query the represented sequence space for desired improvements. This technique allows multiple gene recombination independent of homology. The exact number and position of cross-over events can be pre-determined using fragments designed via bioinformatic analysis. This technology leads to a very high level of diversity with virtually no parental gene reformation and a low level of inactive genes. Combined with GSSM™, a large range of mutations can be tested for improved activity. The method allows "blending" and "fine tuning" of DNA shuffling, for example, codon usage can be optimized.

In Silico Protein Design Automation (PDA) is an optimization algorithm that anchors the structurally defined protein backbone possessing a particular fold, and searches sequence space for amino acid substitutions that can stabilize the fold and overall protein energetics (Hayes et al., Proc. Natl. Acad. Sci. USA 99:15926-15931 (2002)). This technology uses in silico structure-based entropy predictions in order to search for structural tolerance toward protein amino acid variations. Statistical mechanics is applied to calculate coupling interactions at each position. Structural tolerance toward amino acid substitution is a measure of coupling. Ultimately, this technology is designed to yield desired modifications of protein properties while maintaining the integrity of structural characteristics. The method computationally assesses and allows filtering of a very large number of possible sequence variants (1050). The choice of sequence variants to test is related to predictions based on the most favorable thermodynamics. Ostensibly only stability or properties that are linked to stability can be effectively addressed with this technology. The method has been successfully used in some therapeutic proteins, especially in engineering immunoglobulins. In silico predictions avoid testing extraordinarily large numbers of potential variants. Predictions based on existing three-dimensional structures are more likely to succeed than predictions based on hypothetical structures. This technology can readily predict and allow targeted screening of multiple simultaneous mutations, something not possible with purely experimental technologies due to exponential increases in numbers.

Iterative Saturation Mutagenesis (ISM) involves: 1) using knowledge of structure/function to choose a likely site for enzyme improvement; 2) performing saturation mutagenesis at chosen site using a mutagenesis method such as Stratagene QuikChange (Stratagene; San Diego Calif.); 3) screening/selecting for desired properties; and 4) using improved clone(s), start over at another site and continue repeating until a desired activity is achieved (Reetz et al., Nat. Protoc. 2:891-903 (2007); and Reetz et al., Angew. Chem. Int. Ed Engl. 45:7745-7751 (2006)). This is a proven methodology, which assures all possible replacements at a given position are made for screening/selection.

Any of the aforementioned methods for mutagenesis can be used alone or in any combination. Additionally, any one or combination of the directed evolution methods can be used in conjunction with adaptive evolution techniques, as described herein.

It is understood that modifications which do not substantially affect the activity of the various embodiments of this invention are also provided within the definition of the invention provided herein. Accordingly, the following examples are intended to illustrate but not limit the present invention.

EXAMPLE I

Pathways for Producing Butadiene or Crotyl Alcohol

Figure 1:
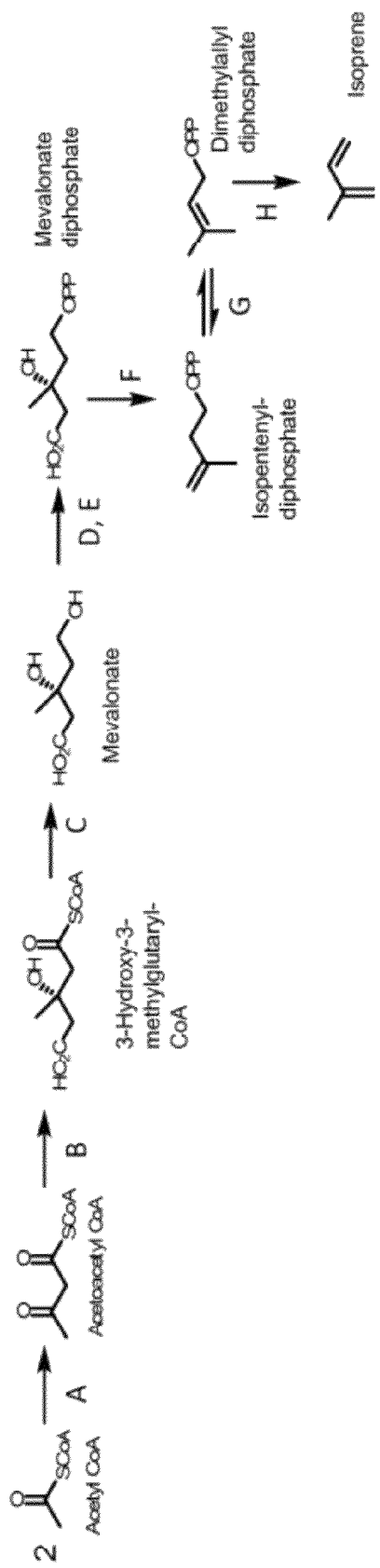
FIG. 1 shows a natural pathway to isoprenoids and terpenes. Enzymes for transformation of the identified substrates to products include: A. acetyl-CoA:acetyl-CoA acyltransferase, B. hydroxymethylglutaryl-CoA synthase, C. 3-hydroxy-3-methylglutaryl-CoA reductase (alcohol forming), D. mevalonate kinase, E. phosphomevalonate kinase, F. diphosphomevalonate decarboxylase, G. isopentenyl-diphosphate isomerase, H. isoprene synthase.

Disclosed herein are novel processes for the direct production of butadiene or crotyl alcohol using engineered non-natural microorganisms that possess the enzymes necessary for conversion of common metabolites into the four carbon diene, 1,3-butadiene or crotyl alcohol. One novel route to direct production of butadiene entails reduction of the known butanol pathway metabolite crotonyl-CoA to crotyl alcohol via reduction with aldehyde and alcohol dehydrogenases, followed by phosphorylation with kinases to afford crotyl pyrophosphate and subsequent conversion to butadiene using isoprene synthases or variants thereof (see FIG. 2). Another route (FIG. 3) is a variant of the well-characterized DXP pathway for isoprenoid biosynthesis. In this route, the substrate lacks a 2-methyl group and provides butadiene rather than isoprene via a butadiene synthase. Such a butadiene synthase can be derived from a isoprene synthase using methods, such as directed evolution, as described herein. Finally, FIG. 4 shows a pathway to butadiene involving the substrate 3-hydroxyglutaryl-CoA, which serves as a surrogate for the natural mevalonate pathway substrate 3-hydroxy-3-methyl-glutaryl-CoA (shown in FIG. 1). Enzyme candidates for steps A-P of FIG. 2, steps A-K of FIG. 3 and steps A-O of FIG. 4 are provided below.

Acetyl-CoA:Acetyl-CoA Acyltransferase (FIG. 2, Step A)

Acetoacetyl-CoA thiolase converts two molecules of acetyl-CoA into one molecule each of acetoacetyl-CoA and CoA. Exemplary acetoacetyl-CoA thiolase enzymes include the gene products of atoB from *E. coli* (Martin et al., *Nat. Biotechnol* 21:796-802 (2003)), thlA and thlB from *C. acetobutylicum* (Hanai et al., *Appl Environ Microbiol* 73:7814-7818 (2007); Winzer et al., *J. Mol. Microbiol Biotechnol* 2:531-541 (2000)), and ERG10 from *S. cerevisiae* (Hiser et al., *J. Biol. Chem.* 269:31383-31389 (1994)).

| Protein | GenBank ID | GI number | Organism |
| --- | --- | --- | --- |
| AtoB | NP_416728 | 16130161 | *Escherichia coli* |
| ThlA | NP_349476.1 | 15896127 | *Clostridium acetobutylicum* |
| ThlB | NP_149242.1 | 15004782 | *Clostridium acetobutylicum* |
| ERG10 | NP_015297 | 6325229 | *Saccharomyces cerevisiae* |

Acetoacetyl-CoA Reductase (FIG. 2, Step B)

Acetoacetyl-CoA reductase catalyzing the reduction of acetoacetyl-CoA to 3-hydroxybutyryl-CoA participates in the acetyl-CoA fermentation pathway to butyrate in several species of *Clostridia* and has been studied in detail (Jones et al., *Microbiol Rev.* 50:484-524 (1986)). The enzyme from *Clostridium acetobutylicum*, encoded by hbd, has been cloned and functionally expressed in *E. coli* (Youngleson et al., *J Bacteriol.* 171:6800-6807 (1989)). Additionally, subunits of two fatty acid oxidation complexes in *E. coli*, encoded by fadB and fadJ, function as 3-hydroxyacyl-CoA dehydrogenases (Binstock et al., *Methods Enzymol.* 71 Pt C:403-411 (1981)). Yet other gene candidates demonstrated to reduce acetoacetyl-CoA to 3-hydroxybutyryl-CoA are phbB from *Zoogloea ramigera* (Ploux et al., *Eur. J Biochem.* 174:177-182 (1988)) and phaB from *Rhodobacter sphaeroides* (Alber et al., *Mol. Microbiol* 61:297-309 (2006)). The former gene candidate is NADPH-dependent, its nucleotide sequence has been determined (Peoples et al., *Mol. Microbiol* 3:349-357 (1989)) and the gene has been expressed in *E. coli*. Substrate specificity studies on the gene led to the conclusion that it could accept 3-oxopropionyl-CoA as a substrate besides acetoacetyl-CoA (Ploux et al., supra, (1988)). Additional gene candidates include Hbd1 (C-terminal domain) and Hbd2 (N-terminal domain) in *Clostridium kluyveri* (Hillmer and Gottschalk, *Biochim. Biophys. Acta* 3334:12-23 (1974)) and HSD17B10 in *Bos taurus* (WAKIL et al., *J Biol. Chem.* 207:631-638 (1954)).

| Protein | Genbank ID | GI number | Organism |
| --- | --- | --- | --- |
| fadB | P21177.2 | 119811 | *Escherichia coli* |
| fadJ | P77399.1 | 3334437 | *Escherichia coli* |
| Hbd2 | EDK34807.1 | 146348271 | *Clostridium kluyveri* |
| Hbd1 | EDK32512.1 | 146345976 | *Clostridium kluyveri* |
| hbd | P52041.2 | 18266893 | *Clostridium acetobutylicum* |
| HSD17B10 | O02691.3 | 3183024 | *Bos Taurus* |
| phbB | P23238.1 | 130017 | *Zoogloea ramigera* |
| phaB | YP_353825.1 | 77464321 | *Rhodobacter sphaeroides* |

A number of similar enzymes have been found in other species of *Clostridia* and in *Metallosphaera sedula* (Berg et al., *Science.* 318:1782-1786 (2007)).

| Protein | GenBank ID | GI number | Organism |
| --- | --- | --- | --- |
| hbd | NP_349314.1 | NP_349314.1 | *Clostridium acetobutylicum* |
| hbd | AAM14586.1 | AAM14586.1 | *Clostridium beijerinckii* |
| Msed_1423 | YP_001191505 | YP_001191505 | *Metallosphaera sedula* |
| Msed_0399 | YP_001190500 | YP_001190500 | *Metallosphaera sedula* |
| Msed_0389 | YP_001190490 | YP_001190490 | *Metallosphaera sedula* |
| Msed_1993 | YP_001192057 | YP_001192057 | *Metallosphaera sedula* |

3-Hydroxybutyryl-CoA Dehydratase (FIG. 2, Step C)

3-Hydroxybutyryl-CoA dehydratase (EC 4.2.1.55), also called crotonase, is an enoyl-CoA hydratase that reversibly dehydrates 3-hydroxybutyryl-CoA to form crotonyl-CoA. Crotonase enzymes are required for n-butanol formation in some organisms, particularly *Clostridial* species, and also comprise one step of the 3-hydroxypropionate/4-hydroxybutyrate cycle in thermoacidophilic Archaea of the genera *Sulfolobus*, *Acidianus*, and *Metallosphaera*. Exemplary genes encoding crotonase enzymes can be found in *C. acetobutylicum* (Atsumi et al., *Metab Eng.* 10:305-311 (2008); Boynton et al., *J Bacteriol.* 178:3015-3024 (1996)), *C. kluyveri* (Hillmer et al., *FEBS Lett.* 21:351-354 (1972)), and *Metallosphaera sedula* (Berg et al., *Science* 318:1782-1786 (2007a)) though the sequence of the latter gene is not known. The enoyl-CoA hydratase of *Pseudomonas putida*, encoded by ech, catalyzes the conversion of crotonyl-CoA to 3-hydroxybutyryl-CoA (Roberts et al., *Arch Microbiol.* 117:99-108 (1978)). Additional enoyl-CoA hydratase candidates are phaA and phaB, of *P. putida*, and paaA and paaB from *P. fluorescens* (Olivera et al., *Proc. Natl. Acad. Sci U.S.A* 95:6419-6424 (1998)). Lastly, a number of *Escherichia coli* genes have been shown to demonstrate enoyl-CoA hydratase functionality including maoC (Park et al., *J Bacteriol.* 185:

5391-5397 (2003)), paaF (Ismail et al., *Eur. J Biochem.* 270: 3047-3054 (2003); Park et al., *Appl. Biochem. Biotechnol* 113-116:335-346 (2004); Park et al., *Biotechnol Bioeng* 86:681-686 (2004)) and paaG (Ismail et al., supra, (2003); Park and Lee, supra, (2004); Park and Yup, supra, (2004)). These proteins are identified below.

| Protein | GenBank ID | GI Number | Organism |
|---|---|---|---|
| crt | NP_349318.1 | 15895969 | *Clostridium acetobutylicum* |
| crt1 | YP_001393856.1 | 153953091 | *Clostridium kluyveri* |
| ech | NP_745498.1 | 26990073 | *Pseudomonas putida* |
| paaA | NP_745427.1 | 26990002 | *Pseudomonas putida* |
| paaB | NP_745426.1 | 26990001 | *Pseudomonas putida* |
| phaA | ABF82233.1 | 106636093 | *Pseudomonas fluorescens* |
| phaB | ABF82234.1 | 106636094 | *Pseudomonas fluorescens* |
| maoC | NP_415905.1 | 16129348 | *Escherichia coli* |
| paaF | NP_415911.1 | 16129354 | *Escherichia coli* |
| paaG | NP_415912.1 | 16129355 | *Escherichia coli* |

Crotonyl-CoA Reductase (Aldehyde Forming) (FIG. 2, Step D)

Several acyl-CoA dehydrogenases are capable of reducing an acyl-CoA to its corresponding aldehyde. Thus they can naturally reduce crotonyl-CoA to crotonaldehyde or can be engineered to do so. Exemplary genes that encode such enzymes include the *Acinetobacter Calcoaceticus* acr1 encoding a fatty acyl-CoA reductase (Reiser et al., *J. Bacteriol.* 179:2969-2975 (1997)), the *Acinetobacter* sp. M-1 fatty acyl-CoA reductase (Ishige et al., *Appl. Environ. Microbiol.* 68:1192-1195 (2002)), and a CoA- and NADP-dependent succinate semialdehyde dehydrogenase encoded by the sucD gene in *Clostridium kluyveri* (Sohling et., *J Bacteriol.* 178: 871-880 (1996); Sohling et al., *J. Bacteriol.* 178:871-80 (1996))). SucD of *P. gingivalis* is another succinate semialdehyde dehydrogenase (Takahashi et al., *J. Bacteriol.* 182: 4704-4710 (2000)). These succinate semialdehyde dehydrogenases were specifically shown in ref. (Burk et al., WO/2008/115840: (2008)) to convert 4-hydroxybutyryl-CoA to 4-hydroxybutanal as part of a pathway to produce 1,4-butanediol. The enzyme acylating acetaldehyde dehydrogenase in *Pseudomonas* sp, encoded by bphG, is yet another capable enzyme as it has been demonstrated to oxidize and acylate acetaldehyde, propionaldehyde, butyraldehyde, isobutyraldehyde and formaldehyde (Powlowski et al., *J. Bacteriol.* 175:377-385 (1993)).

| Protein | GenBank ID | GI Number | Organism |
|---|---|---|---|
| acr1 | YP_047869.1 | 50086359 | *Acinetobacter calcoaceticus* |
| acr1 | AAC45217 | 1684886 | *Acinetobacter baylyi* |
| acr1 | BAB85476.1 | 18857901 | *Acinetobacter* sp. Strain M-1 |
| sucD | P38947.1 | 172046062 | *Clostridium kluyveri* |
| sucD | NP_904963.1 | 34540484 | *Porphyromonas gingivalis* |
| bphG | BAA03892.1 | 425213 | *Pseudomonas* sp |

An additional enzyme type that converts an acyl-CoA to its corresponding aldehyde is malonyl-CoA reductase which transforms malonyl-CoA to malonic semialdehyde. Malonyl-CoA reductase is a key enzyme in autotrophic carbon fixation via the 3-hydroxypropionate cycle in thermoacidophilic archael bacteria (Berg et al., *Science* 318:1782-1786 (2007b); Thauer, 318:1732-1733 (2007)). The enzyme utilizes NADPH as a cofactor and has been characterized in *Metallosphaera* and *Sulfolobus* spp (Alber et al., *J. Bacteriol.* 188: 8551-8559 (2006); Hugler et al., *J. Bacteriol.* 184:2404-2410 (2002)). The enzyme is encoded by Msed_0709 in *Metallosphaera sedula* (Alber et al., supra, (2006); Berg et al., supra, (2007b)). A gene encoding a malonyl-CoA reductase from *Sulfolobus tokodaii* was cloned and heterologously expressed in *E. coli* (Alber et al., supra, (2006)). Although the aldehyde dehydrogenase functionality of these enzymes is similar to the bifunctional dehydrogenase from *Chloroflexus aurantiacus*, there is little sequence similarity. Both malonyl-CoA reductase enzyme candidates have high sequence similarity to aspartate-semialdehyde dehydrogenase, an enzyme catalyzing the reduction and concurrent dephosphorylation of aspartyl-4-phosphate to aspartate semialdehyde. Additional gene candidates can be found by sequence homology to proteins in other organisms including *Sulfolobus solfataricus* and *Sulfolobus acidocaldarius*. Yet another candidate for CoA-acylating aldehyde dehydrogenase is the ald gene from *Clostridium beijerinckii* (Toth, *Appl. Environ. Microbiol.* 65:4973-4980 (1999). This enzyme has been reported to reduce acetyl-CoA and butyryl-CoA to their corresponding aldehydes. This gene is very similar to eutE that encodes acetaldehyde dehydrogenase of *Salmonella typhimurium* and *E. coli* (Toth, *Appl. Environ. Microbiol.* 65:4973-4980 (1999). These proteins are identified below.

| Protein | GenBank ID | GI Number | Organism |
|---|---|---|---|
| Msed_0709 | YP_001190808.1 | 146303492 | *Metallosphaera sedula* |
| Mcr | NP_378167.1 | 15922498 | *Sulfolobus tokodaii* |
| asd-2 | NP_343563.1 | 15898958 | *Sulfolobus solfataricus* |
| Saci_2370 | YP_256941.1 | 70608071 | *Sulfolobus acidocaldarius* |
| Ald | AAT66436 | 49473535 | *Clostridium beijerinckii* |
| eutE | AAA80209 | 687645 | *Salmonella typhimurium* |
| eutE | P77445 | 2498347 | *Escherichia coli* |

Crotonaldehyde Reductase (Alcohol Forming) (FIG. 2, Step E)

Enzymes exhibiting crotonaldehyde reductase (alcohol forming) activity are capable of forming crotyl alcohol from crotonaldehyde. The following enzymes can naturally possess this activity or can be engineered to exhibit this activity. Exemplary genes encoding enzymes that catalyze the conversion of an aldehyde to alcohol (i.e., alcohol dehydrogenase or equivalently aldehyde reductase) include alrA encoding a medium-chain alcohol dehydrogenase for $C_2$-$C_{14}$ (Tani et al., *Appl. Environ. Microbiol.* 66:5231-5235 (2000)), ADH2 from *Saccharomyces cerevisiae* (Atsumi et al., *Nature* 451: 86-89 (2008)), yqhD from *E. coli* which has preference for molecules longer than C(3) (Sulzenbacher et al., *J. Mol. Biol.* 342:489-502 (2004)), and bdh I and bdh II from *C. acetobutylicum* which converts butyraldehyde into butanol (Walter et al., *J. Bacteriol.* 174:7149-7158 (1992)). ADH1 from *Zymomonas mobilis* has been demonstrated to have activity on a number of aldehydes including formaldehyde, acetaldehyde, propionaldehyde, butyraldehyde, and acrolein (Kinoshita, *Appl. Microbiol. Biotechnol.* 22:249-254 (1985)). Cbei_2181 from *Clostridium beijerinckii* NCIMB 8052 encodes yet another useful alcohol dehydrogenase capable of converting crotonaldehyde to crotyl alcohol.

| Protein | GenBank ID | GI Number | Organism |
|---|---|---|---|
| alrA | BAB12273.1 | 9967138 | *Acinetobacter* sp. Strain M-1 |

| Protein | GenBank ID | GI Number | Organism |
|---|---|---|---|
| ADH2 | NP_014032.1 | 6323961 | *Saccharomyces cerevisiae* |
| yqhD | NP_417484.1 | 16130909 | *Escherichia coli* |
| bdh I | NP_349892.1 | 15896543 | *Clostridium acetobutylicum* |
| bdh II | NP_349891.1 | 15896542 | *Clostridium acetobutylicum* |
| adhA | YP_162971.1 | 56552132 | *Zymomonas mobilis* |
| Cbei_2181 | YP_001309304.1 | 150017050 | *Clostridium beijerinckii* NCIMB 8052 |

Enzymes exhibiting 4-hydroxybutyrate dehydrogenase activity (EC 1.1.1.61) also fall into this category. Such enzymes have been characterized in *Ralstonia eutropha* (Bravo et al., *J. Forensic Sci.* 49:379-387 (2004)), *Clostridium kluyveri* (Wolff et al., *Protein Expr. Purif.* 6:206-212 (1995)) and *Arabidopsis thaliana* (Breitkreuz et al., *J. Biol. Chem.* 278:41552-41556 (2003)).

| Protein | GenBank ID | GI Number | Organism |
|---|---|---|---|
| 4hbd | YP_726053.1 | 113867564 | *Ralstonia eutropha* H16 |
| 4hbd | L21902.1 | 146348486 | *Clostridium kluyveri* DSM 555 |
| 4hbd | Q94B07 | 75249805 | *Arabidopsis thaliana* |

Crotyl Alcohol Kinase (FIG. 2, Step F)

Crotyl alcohol kinase enzymes catalyze the transfer of a phosphate group to the hydroxyl group of crotyl alcohol. The enzymes described below naturally possess such activity or can be engineered to exhibit this activity. Kinases that catalyze transfer of a phosphate group to an alcohol group are members of the EC 2.7.1 enzyme class. The table below lists several useful kinase enzymes in the EC 2.7.1 enzyme class.

| Enzyme Commission Number | Enzyme Name |
|---|---|
| 2.7.1.1 | hexokinase |
| 2.7.1.2 | glucokinase |
| 2.7.1.3 | ketohexokinase |
| 2.7.1.4 | fructokinase |
| 2.7.1.5 | rhamnulokinase |
| 2.7.1.6 | galactokinase |
| 2.7.1.7 | mannokinase |
| 2.7.1.8 | glucosamine kinase |
| 2.7.1.10 | phosphoglucokinase |
| 2.7.1.11 | 6-phosphofructokinase |
| 2.7.1.12 | gluconokinase |
| 2.7.1.13 | dehydrogluconokinase |
| 2.7.1.14 | sedoheptulokinase |
| 2.7.1.15 | ribokinase |
| 2.7.1.16 | ribulokinase |
| 2.7.1.17 | xylulokinase |
| 2.7.1.18 | phosphoribokinase |
| 2.7.1.19 | phosphoribulokinase |
| 2.7.1.20 | adenosine kinase |
| 2.7.1.21 | thymidine kinase |
| 2.7.1.22 | ribosylnicotinamide kinase |
| 2.7.1.23 | NAD+ kinase |
| 2.7.1.24 | dephospho-CoA kinase |
| 2.7.1.25 | adenylyl-sulfate kinase |
| 2.7.1.26 | riboflavin kinase |
| 2.7.1.27 | erythritol kinase |
| 2.7.1.28 | triokinase |
| 2.7.1.29 | glycerone kinase |
| 2.7.1.30 | glycerol kinase |
| 2.7.1.31 | glycerate kinase |
| 2.7.1.32 | choline kinase |
| 2.7.1.33 | pantothenate kinase |
| 2.7.1.34 | pantetheine kinase |
| 2.7.1.35 | pyridoxal kinase |
| 2.7.1.36 | mevalonate kinase |
| 2.7.1.39 | homoserine kinase |
| 2.7.1.40 | pyruvate kinase |
| 2.7.1.41 | glucose-1-phosphate phosphodismutase |
| 2.7.1.42 | riboflavin phosphotransferase |
| 2.7.1.43 | glucuronokinase |
| 2.7.1.44 | galacturonokinase |
| 2.7.1.45 | 2-dehydro-3-deoxygluconokinase |
| 2.7.1.46 | L-arabinokinase |
| 2.7.1.47 | D-ribulokinase |
| 2.7.1.48 | uridine kinase |
| 2.7.1.49 | hydroxymethylpyrimidine kinase |
| 2.7.1.50 | hydroxyethylthiazole kinase |
| 2.7.1.51 | L-fuculokinase |
| 2.7.1.52 | fucokinase |
| 2.7.1.53 | L-xylulokinase |
| 2.7.1.54 | D-arabinokinase |
| 2.7.1.55 | allose kinase |
| 2.7.1.56 | 1-phosphofructokinase |
| 2.7.1.58 | 2-dehydro-3-deoxygalactonokinase |
| 2.7.1.59 | N-acetylglucosamine kinase |
| 2.7.1.60 | N-acylmannosamine kinase |
| 2.7.1.61 | acyl-phosphate-hexose phosphotransferase |
| 2.7.1.62 | phosphoramidate-hexose phosphotransferase |
| 2.7.1.63 | polyphosphate-glucose phosphotransferase |
| 2.7.1.64 | inositol 3-kinase |
| 2.7.1.65 | scyllo-inosamine 4-kinase |
| 2.7.1.66 | undecaprenol kinase |
| 2.7.1.67 | 1-phosphatidylinositol 4-kinase |
| 2.7.1.68 | 1-phosphatidylinositol-4-phosphate 5-kinase |
| 2.7.1.69 | protein-Np-phosphohistidine-sugar phosphotransferase |
| 2.7.1.70 | identical to EC 2.7.1.37. |
| 2.7.1.71 | shikimate kinase |
| 2.7.1.72 | streptomycin 6-kinase |
| 2.7.1.73 | inosine kinase |
| 2.7.1.74 | deoxycytidine kinase |
| 2.7.1.76 | deoxyadenosine kinase |
| 2.7.1.77 | nucleoside phosphotransferase |
| 2.7.1.78 | polynucleotide 5'-hydroxyl-kinase |
| 2.7.1.79 | diphosphate-glycerol phosphotransferase |
| 2.7.1.80 | diphosphate-serine phosphotransferase |
| 2.7.1.81 | hydroxylysine kinase |
| 2.7.1.82 | ethanolamine kinase |
| 2.7.1.83 | pseudouridine kinase |
| 2.7.1.84 | alkylglycerone kinase |
| 2.7.1.85 | β-glucoside kinase |
| 2.7.1.86 | NADH kinase |
| 2.7.1.87 | streptomycin 3''-kinase |
| 2.7.1.88 | dihydrostreptomycin-6-phosphate 3'a-kinase |
| 2.7.1.89 | thiamine kinase |

| Enzyme Commission Number | Enzyme Name |
|---|---|
| 2.7.1.90 | diphosphate-fructose-6-phosphate 1-phosphotransferase |
| 2.7.1.91 | sphinganine kinase |
| 2.7.1.92 | 5-dehydro-2-deoxygluconokinase |
| 2.7.1.93 | alkylglycerol kinase |
| 2.7.1.94 | acylglycerol kinase |
| 2.7.1.95 | kanamycin kinase |
| 2.7.1.100 | S-methyl-5-thioribose kinase |
| 2.7.1.101 | tagatose kinase |
| 2.7.1.102 | hamamelose kinase |
| 2.7.1.103 | viomycin kinase |
| 2.7.1.105 | 6-phosphofructo-2-kinase |
| 2.7.1.106 | glucose-1,6-bisphosphate synthase |
| 2.7.1.107 | diacylglycerol kinase |
| 2.7.1.108 | dolichol kinase |
| 2.7.1.113 | deoxyguanosine kinase |
| 2.7.1.114 | AMP-thymidine kinase |
| 2.7.1.118 | ADP-thymidine kinase |
| 2.7.1.119 | hygromycin-B 7"-O-kinase |
| 2.7.1.121 | phosphoenolpyruvate-glycerone phosphotransferase |
| 2.7.1.122 | xylitol kinase |
| 2.7.1.127 | inositol-trisphosphate 3-kinase |
| 2.7.1.130 | tetraacyldisaccharide 4'-kinase |
| 2.7.1.134 | inositol-tetrakisphosphate 1-kinase |
| 2.7.1.136 | macrolide 2'-kinase |
| 2.7.1.137 | phosphatidylinositol 3-kinase |
| 2.7.1.138 | ceramide kinase |
| 2.7.1.140 | inositol-tetrakisphosphate 5-kinase |
| 2.7.1.142 | glycerol-3-phosphate-glucose phosphotransferase |
| 2.7.1.143 | diphosphate-purine nucleoside kinase |
| 2.7.1.144 | tagatose-6-phosphate kinase |
| 2.7.1.145 | deoxynucleoside kinase |
| 2.7.1.146 | ADP-dependent phosphofructokinase |
| 2.7.1.147 | ADP-dependent glucokinase |
| 2.7.1.148 | 4-(cytidine 5'-diphospho)-2-C-methyl-D-erythritol kinase |
| 2.7.1.149 | 1-phosphatidylinositol-5-phosphate 4-kinase |
| 2.7.1.150 | 1-phosphatidylinositol-3-phosphate 5-kinase |
| 2.7.1.151 | inositol-polyphosphate multikinase |
| 2.7.1.153 | phosphatidylinositol-4,5-bisphosphate 3-kinase |
| 2.7.1.154 | phosphatidylinositol-4-phosphate 3-kinase |
| 2.7.1.156 | adenosylcobinamide kinase |
| 2.7.1.157 | N-acetylgalactosamine kinase |
| 2.7.1.158 | inositol-pentakisphosphate 2-kinase |
| 2.7.1.159 | inositol-1,3,4-trisphosphate 5/6-kinase |
| 2.7.1.160 | 2'-phosphotransferase |
| 2.7.1.161 | CTP-dependent riboflavin kinase |
| 2.7.1.162 | N-acetylhexosamine 1-kinase |
| 2.7.1.163 | hygromycin B 4-O-kinase |
| 2.7.1.164 | O-phosphoseryl-tRNASec kinase |

A good candidate for this step is mevalonate kinase (EC 2.7.1.36) that phosphorylates the terminal hydroxyl group of the methyl analog, mevalonate, of 3,5-dihydroxypentanote. Some gene candidates for this step are erg12 from *S. cerevisiae*, mvk from *Methanocaldococcus jannaschi*, MVK from *Homo sapeins*, and mvk from *Arabidopsis thaliana* col.

| Protein | GenBank ID | GI Number | Organism |
|---|---|---|---|
| erg12 | CAA39359.1 | 3684 | Sachharomyces cerevisiae |
| mvk | Q58487.1 | 2497517 | Methanocaldococcus jannaschii |
| mvk | AAH16140.1 | 16359371 | Homo sapiens |
| M\mvk | NP_851084.1 | 30690651 | Arabidopsis thaliana |

Glycerol kinase also phosphorylates the terminal hydroxyl group in glycerol to form glycerol-3-phosphate. This reaction occurs in several species, including *Escherichia coli*, *Saccharomyces cerevisiae*, and *Thermotoga maritima*. The *E. coli* glycerol kinase has been shown to accept alternate substrates such as dihydroxyacetone and glyceraldehyde (Hayashi et al., *J Biol. Chem.* 242:1030-1035 (1967)). T, maritime has two glycerol kinases (Nelson et al., *Nature* 399:323-329 (1999)). Glycerol kinases have been shown to have a wide range of substrate specificity. Crans and Whiteside studied glycerol kinases from four different organisms (*Escherichia coli*, *S. cerevisiae*, *Bacillus stearothermophilus*, and *Candida mycoderma*) (Crans et al., *J. Am. Chem. Soc.* 107:7008-7018 (2010); Nelson et al., supra, (1999)). They studied 66 different analogs of glycerol and concluded that the enzyme could accept a range of substituents in place of one terminal hydroxyl group and that the hydrogen atom at C2 could be replaced by a methyl group. Interestingly, the kinetic constants of the enzyme from all four organisms were very similar. The gene candidates are:

| Protein | GenBank ID | GI Number | Organism |
|---|---|---|---|
| glpK | AP_003883.1 | 89110103 | Escherichia coli K12 |
| glpK1 | NP_228760.1 | 15642775 | Thermotoga maritime MSB8 |
| glpK2 | NP_229230.1 | 15642775 | Thermotoga maritime MSB8 |
| Gut1 | NP_011831.1 | 82795252 | Saccharomyces cerevisiae |

Homoserine kinase is another possible candidate that can lead to the phosphorylation of 3,5-dihydroxypentanoate. This enzyme is also present in a number of organisms including *E. coli*, *Streptomyces* sp, and *S. cerevisiae*. Homoserine kinase from *E. coli* has been shown to have activity on numerous substrates, including, L-2-amino,1,4-butanediol, aspartate semialdehyde, and 2-amino-5-hydroxyvalerate (Huo et al., *Biochemistry* 35:16180-16185 (1996); Huo et al., *Arch. Biochem. Biophys.* 330:373-379 (1996)). This enzyme can act on substrates where the carboxyl group at the alpha position has been replaced by an ester or by a hydroxymethyl group. The gene candidates are:

| Protein | GenBank ID | GI Number | Organism |
|---|---|---|---|
| thrB | BAB96580.2 | 85674277 | Escherichia coli K12 |
| SACT1DRAFT_4809 | ZP_06280784.1 | 282871792 | Streptomyces sp. ACT-1 |
| Thr1 | AAA35154.1 | 172978 | Saccharomyces serevisiae |

2-Butenyl-4-Phosphate Kinase (FIG. 2, Step G)

2-Butenyl-4-phosphate kinase enzymes catalyze the transfer of a phosphate group to the phosphate group of 2-butenyl-4-phosphate. The enzymes described below naturally possess such activity or can be engineered to exhibit this activity. Kinases that catalyze transfer of a phosphate group to another phosphate group are members of the EC 2.7.4 enzyme class. The table below lists several useful kinase enzymes in the EC 2.7.4 enzyme class.

| Enzyme Commission Number | Enzyme Name |
|---|---|
| 2.7.4.1 | polyphosphate kinase |
| 2.7.4.2 | phosphomevalonate kinase |
| 2.7.4.3 | adenylate kinase |
| 2.7.4.4 | nucleoside-phosphate kinase |
| 2.7.4.6 | nucleoside-diphosphate kinase |
| 2.7.4.7 | phosphomethylpyrimidine kinase |
| 2.7.4.8 | guanylate kinase |
| 2.7.4.9 | dTMP kinase |
| 2.7.4.10 | nucleoside-triphosphate-adenylate kinase |
| 2.7.4.11 | (deoxy)adenylate kinase |
| 2.7.4.12 | T2-induced deoxynucleotide kinase |
| 2.7.4.13 | (deoxy)nucleoside-phosphate kinase |
| 2.7.4.14 | cytidylate kinase |
| 2.7.4.15 | thiamine-diphosphate kinase |
| 2.7.4.16 | thiamine-phosphate kinase |
| 2.7.4.17 | 3-phosphoglyceroyl-phosphate-polyphosphate phosphotransferase |
| 2.7.4.18 | farnesyl-diphosphate kinase |
| 2.7.4.19 | 5-methyldeoxycytidine-5'-phosphate kinase |
| 2.7.4.20 | dolichyl-diphosphate-polyphosphate phosphotransferase |
| 2.7.4.21 | inositol-hexakisphosphate kinase |
| 2.7.4.22 | UMP kinase |
| 2.7.4.23 | ribose 1,5-bisphosphate phosphokinase |
| 2.7.4.24 | diphosphoinositol-pentakisphosphate kinase |

Phosphomevalonate kinase enzymes are of particular interest. Phosphomevalonate kinase (EC 2.7.4.2) catalyzes the analogous transformation to 2-butenyl-4-phosphate kinase. This enzyme is encoded by erg8 in *Saccharomyces cerevisiae* (Tsay et al., *Mol. Cell Biol.* 11:620-631 (1991)) and mvaK2 in *Streptococcus pneumoniae, Staphylococcus aureus* and *Enterococcus faecalis* (Doun et al., *Protein Sci.* 14:1134-1139 (2005); Wilding et al., *J Bacteriol.* 182:4319-4327 (2000)). The *Streptococcus pneumoniae* and *Enterococcus faecalis* enzymes were cloned and characterized in *E. coli* (Pilloff et al., *J Biol. Chem.* 278:4510-4515 (2003); Doun et al., *Protein Sci.* 14:1134-1139 (2005)).

| Protein | GenBank ID | GI Number | Organism |
|---|---|---|---|
| Erg8 | AAA34596.1 | 171479 | Saccharomyces cerevisiae |
| mvaK2 | AAG02426.1 | 9937366 | Staphylococcus aureus |
| mvaK2 | AAG02457.1 | 9937409 | Streptococcus pneumoniae |
| mvaK2 | AAG02442.1 | 9937388 | Enterococcus faecalis |

Butadiene Synthase (FIG. 2, Step H)

Butadiene synthase catalyzes the conversion of 2-butenyl-4-diphosphate to 1,3-butadiene. The enzymes described below naturally possess such activity or can be engineered to exhibit this activity. Isoprene synthase naturally catalyzes the conversion of dimethylallyl diphosphate to isoprene, but can also catalyze the synthesis of 1,3-butadiene from 2-butenyl-4-diphosphate. Isoprene synthases can be found in several organisms including *Populus alba* (Sasaki et al., FEBS Letters, 2005, 579 (11), 2514-2518), *Pueraria montana* (Lindberg et al., Metabolic Eng, 2010, 12 (1), 70-79; Sharkey et al., Plant Physiol., 2005, 137 (2), 700-712), and *Populus tremula×Populus alba* (Miller et al., Planta, 2001, 213 (3), 483-487). Additional isoprene synthase enzymes are described in (Chotani et al., WO/2010/031079, Systems Using Cell Culture for Production of Isoprene; Cervin et al., US Patent Application 20100003716, Isoprene Synthase Variants for Improved Microbial Production of Isoprene).

| Protein | GenBank ID | GI Number | Organism |
|---|---|---|---|
| ispS | BAD98243.1 | 63108310 | Populus alba |
| ispS | AAQ84170.1 | 35187004 | Pueraria montana |
| ispS | CAC35696.1 | 13539551 | Populus tremula × Populus alba |

Crotonyl-CoA Hydrolase, Synthetase, Transferase (FIG. 2, Step I)

Crotonyl-CoA hydrolase catalyzes the conversion of crotonyl-CoA to crotonate. The enzymes described below naturally possess such activity or can be engineered to exhibit this activity. 3-Hydroxyisobutyryl-CoA hydrolase efficiently catalyzes the conversion of 3-hydroxyisobutyryl-CoA to 3-hydroxyisobutyrate during valine degradation (Shimomura et al., *J Biol. Chem.* 269:14248-14253 (1994)). Genes encoding this enzyme include hibch of *Rattus norvegicus* (Shimomura et al., supra; Shimomura et al., *Methods Enzymol.* 324: 229-240 (2000)) and *Homo sapiens* (Shimomura et al., supra). The *H. sapiens* enzyme also accepts 3-hydroxybutyryl-CoA and 3-hydroxypropionyl-CoA as substrates (Shimomura et al., supra). Candidate genes by sequence homology include hibch of *Saccharomyces cerevisiae* and BC_2292 of *Bacillus cereus*. These proteins are identified below.

| Protein | GenBank ID | GI Number | Organism |
|---|---|---|---|
| hibch | Q5XIE6.2 | 146324906 | Rattus norvegicus |
| hibch | Q6NVY1.2 | 146324905 | Homo sapiens |
| hibch | P28817.2 | 2506374 | Saccharomyces cerevisiae |
| BC_2292 | AP09256 | 29895975 | Bacillus cereus |

Several eukaryotic acetyl-CoA hydrolases (EC 3.1.2.1) have broad substrate specificity and thus represent suitable candidate enzymes. For example, the enzyme from *Rattus norvegicus* brain (Robinson et al., Res. Commun. 71:959-965 (1976)) can react with but 1-CoA, hexanoyl-CoA and malonyl-CoA. Though its sequence has not been reported, the enzyme from the mitochondrion of the pea leaf also has a broad substrate specificity, with demonstrated activity on acetyl-CoA, propionyl-CoA, butyryl-CoA, palmitoyl-CoA, oleoyl-CoA, succinyl-CoA, and crotonyl-CoA (Zeiher et al., Plant. Physiol. 94:20-27 (1990)). The acetyl-CoA hydrolase, ACH1, from *S. cerevisiae* represents another candidate hydrolase (Buu et al., J. Biol. Chem. 278:17203-17209 (2003)). These proteins are identified below.

| Protein | GenBank ID | GI Number | Organism |
|---------|------------|-----------|----------|
| acot12 | NP_570103.1 | 18543355 | Rattus norvegicus |
| ACH1 | NP_009538 | 6319456 | Saccharomyces cerevisiae |

Another candidate hydrolase is the human dicarboxylic acid thioesterase, acot8, which exhibits activity on glutaryl-CoA, adipyl-CoA, suberyl-CoA, sebacyl-CoA, and dodecanedioyl-CoA (Westin et al., J Biol. Chem. 280:38125-38132 (2005)) and the closest E. coli homolog, tesB, which can also hydrolyze a broad range of CoA thioesters (Naggert et al., J Biol. Chem. 266:11044-11050 (1991)). A similar enzyme has also been characterized in the rat liver (Deana et al., Biochem. Int. 26:767-773 (1992)). Other potential E. coli thioester hydrolases include the gene products of tesA (Bonner et al., Chem. 247:3123-3133 (1972)), ybgC (Kuznetsova et al., FEMS Microbiol Rev 29:263-279 (2005); and (Zhuang et al., FEBS Lett. 516:161-163 (2002)), paaI (Song et al., J Biol. Chem. 281:11028-11038 (2006)), and ybdB (Leduc et al., J Bacteriol. 189:7112-7126 (2007)). These proteins are identified below.

| Protein | GenBank ID | GI Number | Organism |
|---------|------------|-----------|----------|
| tesB | NP_414986 | 16128437 | Escherichia coli |
| acot8 | CAA15502 | 3191970 | Homo sapiens |
| acot8 | NP_570112 | 51036669 | Rattus norvegicus |
| tesA | NP_415027 | 16128478 | Escherichia coli |
| ybgC | NP_415264 | 16128711 | Escherichia coli |
| paaI | NP_415914 | 16129357 | Escherichia coli |
| ybdB | NP_415129 | 16128580 | Escherichia coli |

Yet another candidate hydrolase is the glutaconate CoA-transferase from Acidaminococcus fermentans. This enzyme was transformed by site-directed mutagenesis into an acyl-CoA hydrolase with activity on glutaryl-CoA, acetyl-CoA and 3-butenoyl-CoA (Mack et al., FEBS. Lett. 405:209-212 (1997)). This suggests that the enzymes encoding succinyl-CoA:3-ketoacid-CoA transferases and acetoacetyl-CoA: acetyl-CoA transferases can also serve as candidates for this reaction step but would require certain mutations to change their function. These proteins are identified below.

| Protein | GenBank ID | GI Number | Organism |
|---------|------------|-----------|----------|
| gctA | CAA57199 | 559392 | Acidaminococcus fermentans |
| gctB | CAA57200 | 559393 | Acidaminococcus fermentans |

Crotonyl-CoA synthetase catalyzes the conversion of crotonyl-CoA to crotonate. The enzymes described below naturally possess such activity or can be engineered to exhibit this activity. One candidate enzyme, ADP-forming acetyl-CoA synthetase (ACD, EC 6.2.1.13), couples the conversion of acyl-CoA esters to their corresponding acids with the concurrent synthesis of ATP. Several enzymes with broad substrate specificities have been described in the literature. ACD I from Archaeoglobus fulgidus, encoded by AF1211, was shown to operate on a variety of linear and branched-chain substrates including acetyl-CoA, propionyl-CoA, butyryl-CoA, acetate, propionate, butyrate, isobutyrate, isovalerate, succinate, fumarate, phenylacetate, indoleacetate (Musfeldt et al., J Bacteriol 184:636-644 (2002)). The enzyme from Haloarcula marismortui (annotated as a succinyl-CoA synthetase) accepts propionate, butyrate, and branched-chain acids (isovalerate and isobutyrate) as substrates, and was shown to operate in the forward and reverse directions (Brasen et al., Arch Microbiol 182:277-287 (2004)). The ACD encoded by PAE3250 from hyperthermophilic crenarchaeon Pyrobaculum aerophilum showed the broadest substrate range of all characterized ACDs, reacting with acetyl-CoA, isobutyryl-CoA (preferred substrate) and phenylacetyl-CoA (Brasen et al., supra). The enzymes from A. fulgidus, H. marismortui and P. aerophilum have all been cloned, functionally expressed, and characterized in E. coli (Musfeldt et al., supra; Brasen et al., supra). These proteins are identified below.

| Protein | GenBank ID | GI Number | Organism |
|---------|------------|-----------|----------|
| AF1211 | NP_070039.1 | 11498810 | Archaeoglobus fulgidus DSM 4304 |
| scs | YP_135572.1 | 55377722 | Haloarcula marismortui ATCC 43049 |
| PAE3250 | NP_560604.1 | 18313937 | Pyrobaculum aerophilum str. IM2 |

Another candidate CoA synthetase is succinyl-CoA synthetase. The sucCD genes of E. coli form a succinyl-CoA synthetase complex which naturally catalyzes the formation of succinyl-CoA from succinate with the concaminant consumption of one ATP, a reaction which is reversible in vivo (Buck et al., Biochem. 24:6245-6252 (1985)). These proteins are identified below.

| Protein | GenBank ID | GI Number | Organism |
|---------|------------|-----------|----------|
| sucC | NP_415256.1 | 16128703 | Escherichia coli |
| sucD | AAC73823.1 | 1786949 | Escherichia coli |

Additional exemplary CoA-ligases include the rat dicarboxylate-CoA ligase for which the sequence is yet uncharacterized (Vamecq et al., Biochemical Journal 230:683-693 (1985)), either of the two characterized phenylacetate-CoA ligases from P. chrysogenum (Lamas-Maceiras et al., Biochem. J. 395:147-155 (2005); Wang et al., Biochem Biophy Res Commun 360(2):453-458 (2007)), the phenylacetate-CoA ligase from Pseudomonas putida (Martinez-Blanco et al., J. Biol. Chem. 265:7084-7090 (1990)), and the 6-carboxyhexanoate-CoA ligase from Bacillus subtilis (Bower et al., J. Bacteriol. 178(14):4122-4130 (1996)). Additional candidate enzymes are acetoacetyl-CoA synthetases from Mus musculus (Hasegawa et al., Biochim Biophys Acta 1779:414-419 (2008)) and Homo sapiens (Ohgami et al., Biochem Pharmacol 65:989-994 (2003)) which naturally catalyze the ATP-dependant conversion of acetoacetate into acetoacetyl-CoA. These proteins are identified below.

| Protein | GenBank ID | GI Number | Organism |
|---------|------------|-----------|----------|
| phl | CAJ15517.1 | 77019264 | Penicillium chrysogenum |
| phlB | ABS19624.1 | 152002983 | Penicillium chrysogenum |
| paaF | AAC24333.2 | 22711873 | Pseudomonas putida |

| Protein | GenBank ID | GI Number | Organism |
|---|---|---|---|
| bioW | NP_390902.2 | 50812281 | Bacillus subtilis |
| AACS | NP_084486.1 | 21313520 | Mus musculus |
| AACS | NP_076417.2 | 31982927 | Homo sapiens |

Crotonyl-CoA transferase catalyzes the conversion of crotonyl-CoA to crotonate. The enzymes described below naturally possess such activity or can be engineered to exhibit this activity. Many transferases have broad specificity and thus can utilize CoA acceptors as diverse as acetate, succinate, propionate, butyrate, 2-methylacetoacetate, 3-ketohexanoate, 3-ketopentanoate, valerate, crotonate, 3-mercaptopropionate, propionate, vinylacetate, butyrate, among others. For example, an enzyme from *Roseburia* sp. A2-183 was shown to have butyryl-CoA: acetate: CoA transferase and propionyl-CoA: acetate: CoA transferase activity (Charrier et al., *Microbiology* 152, 179-185 (2006)). Close homologs can be found in, for example, *Roseburia intestinalis* L1-82, *Roseburia inulinivorans* DSM 16841, *Eubacterium rectale* ATCC 33656. Another enzyme with propionyl-CoA transferase activity can be found in *Clostridium propionicum* (Selmer et al., *Eur J Biochem* 269, 372-380 (2002)). This enzyme can use acetate, (R)-lactate, (S)-lactate, acrylate, and butyrate as the CoA acceptor (Selmer et al., *Eur J Biochem* 269, 372-380 (2002); Schweiger and Buckel, *FEBS Letters*, 171(1) 79-84 (1984)). Close homologs can be found in, for example, *Clostridium novyi* NT, *Clostridium beijerinckii* NCIMB 8052, and *Clostridium botulinum* C str. Eklund. YgfH encodes a propionyl CoA:succinate CoA transferase in *E. coli* (Haller et al., *Biochemistry*, 39(16) 4622-4629). Close homologs can be found in, for example, *Citrobacter youngae* ATCC 29220, *Salmonella enterica* subsp. *arizonae* serovar, and *Yersinia intermedia* ATCC 29909. These proteins are identified below.

| Protein | GenBank ID | GI Number | Organism |
|---|---|---|---|
| Ach1 | AAX19660.1 | 60396828 | Roseburia sp. A2-183 |
| ROSINTL182_07121 | ZP_04743841.2 | 257413684 | Roseburia intestinalis L1-82 |
| ROSEINA2194_03642 | ZP_03755203.1 | 225377982 | Roseburia inulinivorans DSM 16841 |
| EUBREC_3075 | YP_002938937.1 | 238925420 | Eubacterium rectale ATCC 33656 |
| pct | CAB77207.1 | 7242549 | Clostridium propionicum |
| NT01CX_2372 | YP_878445.1 | 118444712 | Clostridium novyi NT |
| Cbei_4543 | YP_001311608.1 | 150019354 | Clostridium beijerinckii NCIMB 8052 |
| CBC_A0889 | ZP_02621218.1 | 168186583 | Clostridium botulinum C str. Eklund |
| ygfH | NP_417395.1 | 16130821 | Escherichia coli str. K-12 substr. MG1655 |
| CIT292_04485 | ZP_03838384.1 | 227334728 | Citrobacter youngae ATCC 29220 |
| SARI_04582 | YP_001573497.1 | 161506385 | Salmonella enterica subsp. arizonae serovar |
| yinte0001_14430 | ZP_04635364.1 | 238791727 | Yersinia intermedia ATCC 29909 |

An additional candidate enzyme is the two-unit enzyme encoded by pcaI and pcaJ in *Pseudomonas*, which has been shown to have 3-oxoadipyl-CoA/succinate transferase activity (Kaschabek et al., supra). Similar enzymes based on homology exist in *Acinetobacter* sp. ADP1 (Kowalchuk et al., *Gene* 146:23-30 (1994)) and *Streptomyces coelicolor*. Additional exemplary succinyl-CoA:3:oxoacid-CoA transferases are present in *Helicobacter pylori* (Corthesy-Theulaz et al., *J. Biol. Chem.* 272:25659-25667 (1997)) and *Bacillus subtilis* (Stols et al., *Protein. Expr. Purif.* 53:396-403 (2007)). These proteins are identified below.

| Protein | GenBank ID | GI Number | Organism |
|---|---|---|---|
| pcaI | AAN69545.1 | 24985644 | Pseudomonas putida |
| pcaJ | NP_746082.1 | 26990657 | Pseudomonas putida |
| pcaI | YP_046368.1 | 50084858 | Acinetobacter sp. ADP1 |
| pcaJ | AAC37147.1 | 141776 | Acinetobacter sp. ADP1 |
| pcaI | NP_630776.1 | 21224997 | Streptomyces coelicolor |
| pcaJ | NP_630775.1 | 21224996 | Streptomyces coelicolor |
| HPAG1_0676 | YP_627417 | 108563101 | Helicobacter pylori |
| HPAG1_0677 | YP_627418 | 108563102 | Helicobacter pylori |
| ScoA | NP_391778 | 16080950 | Bacillus subtilis |
| ScoB | NP_391777 | 16080949 | Bacillus subtilis |

A CoA transferase that can utilize acetate as the CoA acceptor is acetoacetyl-CoA transferase, encoded by the *E. coli* atoA (alpha subunit) and atoD (beta subunit) genes (Vanderwinkel et al., *Biochem. Biophys. Res Commun.* 33:902-908 (1968); Korolev et al., *Acta Crystallogr. D Biol Crystallogr.* 58:2116-2121 (2002)). This enzyme has also been shown to transfer the CoA moiety to acetate from a variety of branched and linear acyl-CoA substrates, including isobutyrate (Matthies et al., *Appl Environ Microbiol* 58:1435-1439 (1992)), valerate (Vanderwinkel et al., supra) and butanoate (Vanderwinkel et al., supra). Similar enzymes exist in *Corynebacterium glutamicum* ATCC 13032 (Duncan et al., *Appl Environ Microbiol* 68:5186-5190 (2002)), *Clostridium acetobutylicum* (Cary et al., *Appl Environ Microbiol* 56:1576-1583 (1990)), and *Clostridium saccharoperbutylacetonicum* (Kosaka et al., *Biosci. Biotechnol Biochem.* 71:58-68 (2007)). These proteins are identified below.

| Protein | GenBank ID | GI Number | Organism |
|---|---|---|---|
| atoA | P76459.1 | 2492994 | Escherichia coli K12 |
| atoD | P76458.1 | 2492990 | Escherichia coli K12 |
| actA | YP_226809.1 | 62391407 | Corynebacterium glutamicum |

| Protein | GenBank ID | GI Number | Organism |
|---|---|---|---|
| cg0592 | YP_224801.1 | 62389399 | Corynebacterium glutamicum ATCC 13032 |
| ctfA | NP_149326.1 | 15004866 | Clostridium acetobutylicum |
| ctfB | NP_149327.1 | 15004867 | Clostridium acetobutylicum |
| ctfA | AAP42564.1 | 31075384 | Clostridium saccharoperbutylacetonicum |
| ctfB | AAP42565.1 | 31075385 | Clostridium saccharoperbutylacetonicum |

The above enzymes can also exhibit the desired activities on crotonyl-CoA. Additional exemplary transferase candidates are catalyzed by the gene products of cat1, cat2, and cat3 of *Clostridium kluyveri* which have been shown to exhibit succinyl-CoA, 4-hydroxybutyryl-CoA, and butyryl-CoA transferase activity, respectively (Seedorf et al., supra; Sohling et al., *Eur. J Biochem.* 212:121-127 (1993); Sohling et al., *J Bacteriol.* 178:871-880 (1996)). Similar CoA transferase activities are also present in *Trichomonas vaginalis* (van Grinsven et al., *J. Biol. Chem.* 283:1411-1418 (2008)) and *Trypanosoma brucei* (Riviere et al., *J. Biol. Chem.* 279:45337-45346 (2004)). These proteins are identified below.

| Protein | GenBank ID | GI Number | Organism |
|---|---|---|---|
| cat1 | P38946.1 | 729048 | Clostridium kluyveri |
| cat2 | P38942.2 | 172046066 | Clostridium kluyveri |
| cat3 | EDK35586.1 | 146349050 | Clostridium kluyveri |
| TVAG_395550 | XP_001330176 | 123975034 | Trichomonas vaginalis G3 |
| Tb11.02.0290 | XP_828352 | 71754875 | Trypanosoma brucei |

The glutaconate-CoA-transferase (EC 2.8.3.12) enzyme from anaerobic bacterium *Acidaminococcus fermentans* reacts with diacid glutaconyl-CoA and 3-butenoyl-CoA (Mack et al., *FEBS Lett.* 405:209-212 (1997)). The genes encoding this enzyme are gctA and gctB. This enzyme has reduced but detectable activity with other CoA derivatives including glutaryl-CoA, 2-hydroxyglutaryl-CoA, adipyl-CoA and acrylyl-CoA (Buckel et al., *Eur. J. Biochem.* 118:315-321 (1981)). The enzyme has been cloned and expressed in *E. coli* (Mack et al., *Eur. J. Biochem.* 226:41-51 (1994)). These proteins are identified below.

| Protein | GenBank ID | GI Number | Organism |
|---|---|---|---|
| gctA | CAA57199.1 | 559392 | Acidaminococcus fermentans |
| gctB | CAA57200.1 | 559393 | Acidaminococcus fermentans |

Crotonate Reductase (FIG. 2, Step J)

Crotonate reductase enzymes are capable of catalyzing the conversion of crotonate to crotonaldehyde. The enzymes described below naturally possess such activity or can be engineered to exhibit this activity. Carboxylic acid reductase catalyzes the magnesium, ATP and NADPH-dependent reduction of carboxylic acids to their corresponding aldehydes (Venkitasubramanian et al., *J. Biol. Chem.* 282:478-485 (2007)). This enzyme, encoded by car, was cloned and functionally expressed in *E. coli* (Venkitasubramanian et al., *J. Biol. Chem.* 282:478-485 (2007)). Expression of the npt gene product improved activity of the enzyme via post-transcriptional modification. The npt gene encodes a specific phosphopantetheine transferase (PPTase) that converts the inactive apo-enzyme to the active holo-enzyme. The natural substrate of this enzyme is vanillic acid, and the enzyme exhibits broad acceptance of aromatic and aliphatic substrates (Venkitasubramanian et al., in *Biocatalysis in the Pharmaceutical and Biotechnology Industires*, ed. R. N. Patel, Chapter 15, pp. 425-440, CRC Press LLC, Boca Raton, Fla. (2006)).

| Protein | GenBank ID | GI Number | Organism |
|---|---|---|---|
| Car | AAR91681.1 | 40796035 | Nocardia iowensis (sp. NRRL 5646) |
| Npt | ABI83656.1 | 114848891 | Nocardia iowensis (sp. NRRL 5646) |

Additional car and npt genes can be identified based on sequence homology.

| Protein | GenBank ID | GI Number | Organism |
|---|---|---|---|
| fadD9 | YP_978699.1 | 121638475 | Mycobacterium bovis BCG |
| BCG_2812c | YP_978898.1 | 121638674 | Mycobacterium bovis BCG |
| nfa20150 | YP_118225.1 | 54023983 | Nocardia farcinica IFM 10152 |
| nfa40540 | YP_120266.1 | 54026024 | Nocardia farcinica IFM 10152 |
| SGR_6790 | YP_001828302.1 | 182440583 | Streptomyces griseus subsp. griseus NBRC 13350 |
| SGR_665 | YP_001822177.1 | 182434458 | Streptomyces griseus subsp. griseus NBRC 13350 |
| MSMEG_2956 | YP_887275.1 | 118473501 | Mycobacterium smegmatis MC2 155 |
| MSMEG_5739 | YP_889972.1 | 118469671 | Mycobacterium smegmatis MC2 155 |
| MSMEG_2648 | YP_886985.1 | 118471293 | Mycobacterium smegmatis MC2 155 |
| MAP1040c | NP_959974.1 | 41407138 | Mycobacterium avium subsp. paratuberculosis K-10 |
| MAP2899c | NP_961833.1 | 41408997 | Mycobacterium avium subsp. paratuberculosis K-10 |
| MMAR_2117 | YP_001850422.1 | 183982131 | Mycobacterium marinum M |
| MMAR_2936 | YP_001851230.1 | 183982939 | Mycobacterium marinum M |
| MMAR_1916 | YP_001850220.1 | 183981929 | Mycobacterium marinum M |
| TpauDRAFT_33060 | ZP_04027864.1 | 227980601 | Tsukamurella paurometabola DSM 20162 |
| TpauDRAFT_20920 | ZP_04026660.1 | 227979396 | Tsukamurella paurometabola DSM 20162 |
| CPCC7001_1320 | ZP_05045132.1 | 254431429 | Cyanobium PCC7001 |
| DDBDRAFT_0187729 | XP_636931.1 | 66806417 | Dictyostelium discoideum AX4 |

An additional enzyme candidate found in *Streptomyces griseus* is encoded by the griC and griD genes. This enzyme is believed to convert 3-amino-4-hydroxybenzoic acid to 3-amino-4-hydroxybenzaldehyde as deletion of either griC or griD led to accumulation of extracellular 3-acetylamino-4-hydroxybenzoic acid, a shunt product of 3-amino-4-hydroxybenzoic acid metabolism (Suzuki, et al., *J. Antibiot.* 60(6): 380-387 (2007)). Co-expression of griC and griD with SGR_665, an enzyme similar in sequence to the *Nocardia iowensis* npt, can be beneficial.

| Protein | GenBank ID | GI Number | Organism |
|---|---|---|---|
| griC | YP_001825755.1 | 182438036 | *Streptomyces griseus* subsp. *griseus* NBRC 13350 |
| Grid | YP_001825756.1 | 182438037 | *Streptomyces griseus* subsp. *griseus* NBRC 13350 |

An enzyme with similar characteristics, alpha-aminoadipate reductase (AAR, EC 1.2.1.31), participates in lysine biosynthesis pathways in some fungal species. This enzyme naturally reduces alpha-aminoadipate to alpha-aminoadipate semialdehyde. The carboxyl group is first activated through the ATP-dependent formation of an adenylate that is then reduced by NAD(P)H to yield the aldehyde and AMP. Like CAR, this enzyme utilizes magnesium and requires activation by a PPTase. Enzyme candidates for AAR and its corresponding PPTase are found in *Saccharomyces cerevisiae* (Morris et al., *Gene* 98:141-145 (1991)), *Candida albicans* (Guo et al., *Mol. Genet. Genomics* 269:271-279 (2003)), and *Schizosaccharomyces pombe* (Ford et al., *Curr. Genet.* 28:131-137 (1995)). The AAR from *S. pombe* exhibited significant activity when expressed in *E. coli* (Guo et al., Yeast 21:1279-1288 (2004)). The AAR from *Penicillium chrysogenum* accepts S-carboxymethyl-L-cysteine as an alternate substrate, but did not react with adipate, L-glutamate or diaminopimelate (Hijarrubia et al., *J. Biol. Chem.* 278:8250-8256 (2003)). The gene encoding the *P. chrysogenum* PPTase has not been identified to date.

| Protein | GenBank ID | GI Number | Organism |
|---|---|---|---|
| LYS2 | AAA34747.1 | 171867 | *Saccharomyces cerevisiae* |
| LYS5 | P50113.1 | 1708896 | *Saccharomyces cerevisiae* |
| LYS2 | AAC02241.1 | 2853226 | *Candida albicans* |
| LYS5 | AAO26020.1 | 28136195 | *Candida albicans* |
| Lys1p | P40976.3 | 13124791 | *Schizosaccharomyces pombe* |
| Lys7p | Q10474.1 | 1723561 | *Schizosaccharomyces pombe* |
| Lys2 | CAA74300.1 | 3282044 | *Penicillium chrysogenum* |

Crotonyl-CoA Reductase (Alcohol Forming) (FIG. 2, Step K)

Crotonaldehyde reductase (alcohol forming) enzymes catalyze the 2 reduction steps required to form crotyl alcohol from crotonyl-CoA. Exemplary 2-step oxidoreductases that convert an acyl-CoA to an alcohol are provided below. Such enzymes can naturally convert crotonyl-CoA to crotyl alcohol or can be engineered to do so. These enzymes include those that transform substrates such as acetyl-CoA to ethanol (e.g., adhE from *E. coli* (Kessler et al., *FEBS. Lett.* 281:59-63 (1991))) and butyryl-CoA to butanol (e.g. adhE2 from *C. acetobutylicum* (Fontaine et al., *J. Bacteriol.* 184:821-830 (2002))). The adhE2 enzyme from *C. acetobutylicum* was specifically shown in ref. (Burk et al., supra, (2008)) to produce BDO from 4-hydroxybutyryl-CoA. In addition to reducing acetyl-CoA to ethanol, the enzyme encoded by adhE in *Leuconostoc mesenteroides* has been shown to oxide the branched chain compound isobutyraldehyde to isobutyryl-CoA (Kazahaya et al., *J. Gen. Appl. Microbiol.* 18:43-55 (1972); Koo et al., *Biotechnol. Lett.* 27:505-510 (2005)).

| Protein | GenBank ID | GI Number | Organism |
|---|---|---|---|
| adhE | NP_415757.1 | 16129202 | *Escherichia coli* |
| adhE2 | AAK09379.1 | 12958626 | *Clostridium acetobutylicum* |
| adhE | AAV66076.1 | 55818563 | *Leuconostoc mesenteroides* |

Another exemplary enzyme can convert malonyl-CoA to 3-HP. An NADPH-dependent enzyme with this activity has characterized in *Chloroflexus aurantiacus* where it participates in the 3-hydroxypropionate cycle (Hugler et al., supra, (2002); Strauss et al., 215:633-643 (1993)). This enzyme, with a mass of 300 kDa, is highly substrate-specific and shows little sequence similarity to other known oxidoreductases (Hugler et al., supra, (2002)). No enzymes in other organisms have been shown to catalyze this specific reaction; however there is bioinformatic evidence that other organisms can have similar pathways (Klatt et al., *Environ Microbiol.* 9:2067-2078 (2007)). Enzyme candidates in other organisms including *Roseiflexus castenholzii*, *Erythrobacter* sp. NAP1 and marine gamma proteobacterium HTCC2080 can be inferred by sequence similarity.

| Protein | GenBank ID | GI Number | Organism |
|---|---|---|---|
| mcr | AAS20429.1 | 42561982 | *Chloroflexus aurantiacus* |
| Rcas_2929 | YP_001433009.1 | 156742880 | *Roseiflexus castenholzii* |
| NAP1_02720 | ZP_01039179.1 | 85708113 | *Erythrobacter* sp. NAP1 |
| MGP2080_00535 | ZP_01626393.1 | 119504313 | marine gamma proteobacterium HTCC2080 |

Glutaconyl-CoA Decarboxylase (FIG. 2, Step L)

Glutaconyl-CoA decarboxylase enzymes, characterized in glutamate-fermenting anaerobic bacteria, are sodium-ion translocating decarboxylases that utilize biotin as a cofactor and are composed of four subunits (alpha, beta, gamma, and delta) (Boiangiu et al., *J Mol. Microbiol Biotechnol* 10:105-119 (2005); Buckel, *Biochim Biophys Acta.* 1505:15-27 (2001)). Such enzymes have been characterized in *Fusobacterium nucleatum* (Beatrix et al., *Arch Microbiol.* 154:362-369 (1990)) and *Acidaminococcus fermentans* (Braune et al., *Mol. Microbiol* 31:473-487 (1999)). Analogs to the *F. nucleatum* glutaconyl-CoA decarboxylase alpha, beta and delta subunits are found in *S. aciditrophicus*. A gene annotated as an enoyl-CoA dehydrogenase, syn_00480, another GCD, is located in a predicted operon between a biotin-carboxyl carrier (syn_00479) and a glutaconyl-CoA decarboxylase alpha subunit (syn_00481). The protein sequences for exemplary gene products can be found using the following GenBank accession numbers shown below.

| Protein | GenBank ID | GI Number | Organism |
|---|---|---|---|
| gcdA | CAA49210 | 49182 | *Acidaminococcus fermentans* |
| gcdC | AAC69172 | 3777506 | *Acidaminococcus fermentans* |

| Protein | GenBank ID | GI Number | Organism |
|---------|------------|-----------|----------|
| gcdD | AAC69171 | 3777505 | *Acidaminococcus fermentans* |
| gcdB | AAC69173 | 3777507 | *Acidaminococcus fermentans* |
| FN0200 | AAL94406 | 19713641 | *Fusobacterium nucleatum* |
| FN0201 | AAL94407 | 19713642 | *Fusobacterium nucleatum* |
| FN0204 | AAL94410 | 19713645 | *Fusobacterium nucleatum* |
| syn_00479 | YP_462066 | 85859864 | *Syntrophus aciditrophicus* |
| syn_00481 | YP_462068 | 85859866 | *Syntrophus aciditrophicus* |
| syn_01431 | YP_460282 | 85858080 | *Syntrophus aciditrophicus* |
| syn_00480 | ABC77899 | 85722956 | *Syntrophus aciditrophicus* |

Glutaryl-CoA Dehydrogenase (FIG. 2 Step M)

Glutaryl-CoA dehydrogenase (GCD, EC 1.3.99.7 and EC 4.1.1.70) is a bifunctional enzyme that catalyzes the oxidative decarboxylation of glutaryl-CoA to crotonyl-CoA (FIG. 3, step 3). Bifunctional GCD enzymes are homotetramers that utilize electron transfer flavoprotein as an electron acceptor (Hartel et al., *Arch Microbiol*. 159:174-181 (1993)). Such enzymes were first characterized in cell extracts of *Pseudomonas* strains KB740 and K172 during growth on aromatic compounds (Hartel et al., supra, (1993)), but the associated genes in these organisms is unknown. Genes encoding glutaryl-CoA dehydrogenase (gcdH) and its cognate transcriptional regulator (gcdR) were identified in *Azoarcus* sp. CIB (Blazquez et al., *Environ Microbiol*. 10:474-482 (2008)). An *Azoarcus* strain deficient in gcdH activity was used to identify the a heterologous gene gcdH from *Pseudomonas putida* (Blazquez et al., supra, (2008)). The cognate transcriptional regulator in *Pseudomonas putida* has not been identified but the locus PP_0157 has a high sequence homology (>69% identity) to the *Azoarcus* enzyme. Additional GCD enzymes are found in *Pseudomonas fluorescens* and *Paracoccus* denitrificans (Husain et al., *J Bacteriol*. 163:709-715 (1985)). The human GCD has been extensively studied, overexpressed in *E. coli* (Dwyer et al., *Biochemistry* 39:11488-11499 (2000)), crystallized, and the catalytic mechanism involving a conserved glutamate residue in the active site has been described (Fu et al., *Biochemistry* 43:9674-9684 (2004)). A GCD in *Syntrophus aciditrophicus* operates in the $CO_2$-assimilating direction during growth on crotonate (Mouttaki et al., *Appl Environ Microbiol*. 73:930-938 (2007))). Two GCD genes in *S. aciditrophicus* were identified by protein sequence homology to the *Azoarcus* GcdH: syn_00480 (31%) and syn_01146 (31%). No significant homology was found to the *Azoarcus* GcdR regulatory protein. The protein sequences for exemplary gene products can be found using the following GenBank accession numbers shown below.

| Protein | GenBank ID | GI Number | Organism |
|---------|------------|-----------|----------|
| gcdH | ABM69268.1 | 123187384 | *Azoarcus* sp. CIB |
| gcdR | ABM69269.1 | 123187385 | *Azoarcus* sp. CIB |
| gcdH | AAN65791.1 | 24981507 | *Pseudomonas putida* KT2440 |
| PP_0157 (gcdR) | AAN65790.1 | 24981506 | *Pseudomonas putida* KT2440 |
| gcdH | YP_257269.1 | 70733629 | *Pseudomonas fluorescens* Pf-5 |
| gcvA (gcdR) | YP_257268.1 | 70733628 | *Pseudomonas fluorescens* Pf-5 |
| gcd | YP_918172.1 | 119387117 | *Paracoccus denitrificans* |
| gcdR | YP_918173.1 | 119387118 | *Paracoccus denitrificans* |

| Protein | GenBank ID | GI Number | Organism |
|---------|------------|-----------|----------|
| gcd | AAH02579.1 | 12803505 | *Homo sapiens* |
| syn_00480 | ABC77899 | 85722956 | *Syntrophus aciditrophicus* |
| syn_01146 | ABC76260 | 85721317 | *Syntrophus aciditrophicus* |

3-Aminobutyryl-CoA Deaminase (FIG. 2, Step N)

3-aminobutyryl-CoA is an intermediate in lysine fermentation. It also can be formed from acetoacetyl-CoA via a transaminase or an aminating dehydrogenase. 3-aminobutyryl-CoA deaminase (or 3-aminobutyryl-CoA ammonia lyase) catalyzes the deamination of 3-aminobutyryl-CoA to form crotonyl-CoA. This reversible enzyme is present in *Fusobacterium nucleatum, Porphyromonas gingivalis, Thermoanaerobacter tengcongensis*, and several other organisms and is co-localized with several genes involved. in lysine fermentation (Kreimeyer et al., *J Biol Chem*, 2007, 282(10) 7191-7197).

| Protein | GenBank ID | GI Number | Organism |
|---------|------------|-----------|----------|
| kal | NP_602669.1 | 19705174 | *Fusobacterium nucleatum* subsp. *nucleatum* ATCC 25586 |
| kal | NP_905282.1 | 34540803 | *Porphyromonas gingivalis* W83 |
| kal | NP_622376.1 | 20807205 | *Thermoanaerobacter tengcongensis* MB4 |

4-Hydroxybutyryl-CoA Dehydratase (FIG. 2, Step O)

Several enzymes naturally catalyze the dehydration of 4-hydroxybutyryl-CoA to crotonyl-CoA. This transformation is required for 4-aminobutyrate fermentation by *Clostridium aminobutyricum* (Scherf et al., *Eur. J Biochem*. 215:421-429 (1993)) and succinate-ethanol fermentation by *Clostridium kluyveri* (Scherf et al., *Arch. Microbiol* 161:239-245 (1994)). The transformation is also a key step in Archaea, for example, *Metallosphaera sedula*, as part of the 3-hydroxypropionate/4-hydroxybutyrate autotrophic carbon dioxide assimilation pathway (Berg et al., supra, (2007)). The reversibility of 4-hydroxybutyryl-CoA dehydratase is well-documented (Muh et al., *Biochemistry*. 35:11710-11718 (1996); Friedrich et al., *Angew. Chem. Int. Ed. Engl*. 47:3254-3257 (2008); Muh et al., *Eur. J. Biochem*. 248:380-384 (1997)) and the equilibrium constant has been reported to be about 4 on the side of crotonoyl-CoA (Scherf and Buckel, supra, (1993)).

| Protein | GenBank ID | GI Number | Organism |
|---------|------------|-----------|----------|
| AbfD | CAB60035 | 70910046 | *Clostridium aminobutyricum* |
| AbfD | YP_001396399 | 153955634 | *Clostridium kluyveri* |
| Msed_1321 | YP_001191403 | 146304087 | *Metallosphaera sedula* |
| Msed_1220 | YP_001191305 | 146303989 | *Metallosphaera sedula* |

Crotyl Alcohol Diphosphokinase (FIG. 2, Step P)

Crotyl alcohol diphosphokinase enzymes catalyze the transfer of a diphosphate group to the hydroxyl group of crotyl alcohol. The enzymes described below naturally possess such activity or can be engineered to exhibit this activity. Kinases that catalyze transfer of a diphosphate group are members of the EC 2.7.6 enzyme class. The table below lists several useful kinase enzymes in the EC 2.7.6 enzyme class.

| Enzyme Commission Number | Enzyme Name |
|---|---|
| 2.7.6.1 | ribose-phosphate diphosphokinase |
| 2.7.6.2 | thiamine diphosphokinase |
| 2.7.6.3 | 2-amino-4-hydroxy-6-hydroxymethyldihydropteridine diphosphokinase |
| 2.7.6.4 | nucleotide diphosphokinase |
| 2.7.6.5 | GTP diphosphokinase |

Of particular interest are ribose-phosphate diphosphokinase enzymes which have been identified in *Escherichia coli* (Hove-Jenson et al., J Biol Chem, 1986, 261(15); 6765-71) and *Mycoplasma pneumoniae* M129 (McElwain et al, International Journal of Systematic Bacteriology, 1988, 38:417-423) as well as thiamine diphosphokinase enzymes. Exemplary thiamine diphosphokinase enzymes are found in *Arabidopsis thaliana* (Ajjawi, Plant Mol Biol, 2007, 65(1-2); 151-62).

| Protein | GenBank ID | GI Number | Organism |
|---|---|---|---|
| prs | NP_415725.1 | 16129170 | *Escherichia coli* |
| prsA | NP_109761.1 | 13507812 | *Mycoplasma pneumoniae* M129 |
| TPK1 | BAH19964.1 | 222424006 | *Arabidopsis thaliana* col |
| TPK2 | BAH57065.1 | 227204427 | *Arabidopsis thaliana* col |

Erythrose-4-Phosphate Reductase (FIG. 3, Step A)

In Step A of the pathway, erythrose-4-phosphate is converted to erythritol-4-phosphate by the erythrose-4-phosphate reductase or erythritol-4-phosphate dehydrogenase. The reduction of erythrose-4-phosphate was observed in *Leuconostoc oenos* during the production of erythritol (Veiga-da-Cunha et al., J Bacteriol. 175:3941-3948 (1993)). NADPH was identified as the cofactor (Veiga-da-Cunha et al., supra, (1993)). However, gene for erythrose-4-phosphate was not identified. Thus, it is possible to identify the erythrose-4-phosphate reductase gene from *Leuconostoc oenos* and apply to this step. Additionally, enzymes catalyzing similar reactions can be utilized for this step. An example of these enzymes is 1-deoxy-D-xylulose-5-phosphate reductoisomerase (EC 1.1.1.267) catalyzing the conversion of 1-deoxy-D-xylulose 5-phosphate to 2-C-methyl-D-erythritol-4-phosphate, which has one additional methyl group comparing to Step A. The dxr or ispC genes encode the 1-deoxy-D-xylulose-5-phosphate reductoisomerase have been well studied: the Dxr proteins from *Escherichia coli* and *Mycobacterium tuberculosis* were purified and their crystal structures were determined (Yajima et al., Acta Crystallogr. Sect. F. Struct. Biol. Cryst. Commun. 63:466-470 (2007); Mac et al., J Mol. Biol. 345:115-127 (2005); Henriksson et al., Acta Crystallogr. D. Biol. Crystallogr. 62:807-813 (2006); Henriksson et al., J Biol. Chem. 282:19905-19916 (2007)); the Dxr protein from *Synechocystis* sp was studied by site-directed mutagenesis with modified activity and altered kinetics (Fernandes et al., Biochim. Biophys. Acta 1764:223-229 (2006); Fernandes et al., Arch. Biochem. Biophys. 444:159-164 (2005)). Furthermore, glyceraldehyde 3-phosphate reductase YghZ from *Escherichia coli* catalyzes the conversion between glyceraldehyde 3-phosphate and glycerol-3-phosphate (Desai et al., Biochemistry 47:7983-7985 (2008)) can also be applied to this step. The following genes can be used for Step A conversion:

| Protein | GenBank ID | GI Number | Organism |
|---|---|---|---|
| dxr | P45568.2 | 2506592 | *Escherichia coli* strain K12 |
| dxr | A5U6M4.1 | 166218269 | *Mycobacterium tuberculosis* |
| dxr | Q55663.1 | 2496789 | *Synechocystis* sp. strain PCC6803 |
| yghZ | NP_417474.1 | 16130899 | *Escherichia coli* strain K12 |

Erythritol-4-Phospate Cytidylyltransferase (FIG. 3, Step B)

In Step B of the pathway, erythritol-4-phosphate is converted to 4-(cytidine 5'-diphospho)-erythritol by the erythritol-4-phospate cytidylyltransferase or 4-(cytidine 5'-diphospho)-erythritol synthase. The exact enzyme for this step has not been identified. However, enzymes catalyzing similar reactions can be applied to this step. An example is the 2-C-methyl-D-erythritol 4-phosphate cytidylyltransferase or 4-(cytidine 5'-diphospho)-2-C-methyl-D-erythritol synthase (EC 2.7.7.60). The 2-C-methyl-D-erythritol 4-phospate cytidylyltransferase is in the methylerythritol phosphate pathway for the isoprenoid biosynthesis and catalyzes the conversion between 2-C-methyl-D-erythritol 4-phospate and 4-(cytidine 5'-diphospho)-2-C-methyl-D-erythritol, with an extra methyl group comparing to Step B conversion. The 2-C-methyl-D-erythritol 4-phosphate cytidylyltransferase is encoded by ispD gene and the crystal structure of *Escherichia coli* IspD was determined (Kemp et al., Acta Crystallogr. D. Biol. Crystallogr. 57:1189-1191 (2001); Kemp et al., Acta Crystallogr. D. Biol. Crystallogr. 59:607-610 (2003); Richard et al., Nat. Struct. Biol. 8:641-648 (2001)). The ispD gene from *Mycobacterium tuberculosis* H37Rv was cloned and expressed in *Escherichia coli*, and the recombinant proteins were purified with N-terminal His-tag (Shi et al., J Biochem. Mol. Biol. 40:911-920 (2007)). Additionally, the *Streptomyces coelicolor* ispD gene was cloned and expressed in *E. coli*, and the recombinant proteins were characterized physically and kinetically (Cane et al., Bioorg. Med. Chem. 9:1467-1477 (2001)). The following genes can be used for Step B conversion:

| Protein | GenBank ID | GI Number | Organism |
|---|---|---|---|
| ispD | Q46893.3 | 2833415 | *Escherichia coli* strain K12 |
| ispD | A5U8Q7.1 | 166215456 | *Mycobacterium tuberculosis* |
| ispD | Q9L0Q8.1 | 12230289 | *Streptomyces coelicolor* |

4-(Cytidine 5'-diphospho)-erythritol kinase (FIG. 3, Step C)

In Step C of the pathway, 4-(cytidine 5'-diphospho)-erythritol is converted to 2-phospho-4-(cytidine 5'-diphospho)-erythritol by the 4-(cytidine 5'-diphospho)-erythritol kinase. The exact enzyme for this step has not been identified. However, enzymes catalyzing similar reactions can be applied to this step. An example is the 4-diphosphocytidyl-2-C-methylerythritol kinase (EC 2.7.1.148). The 4-diphosphocytidyl-2-C-methylerythritol kinase is also in the methylerythritol phosphate pathway for the isoprenoid biosynthesis and catalyzes the conversion between 4-(cytidine 5'-diphospho)-2-C-methyl-D-erythritol and 2-phospho-4-(cytidine 5'-diphospho)-2-C-methyl-D-erythritol, with an extra methyl group comparing to Step C conversion. The 4-diphosphocytidyl-2-C-methylerythritol kinase is encoded by ispE gene and the crystal structures of *Escherichia coli, Thermos thermophilus* HB8, and *Aquifex aeolicus* IspE were determined (Sgraja et al., *FEBS J* 275:2779-2794 (2008); Miallau et al., *Proc. Natl. Acad. Sci. U.S.A* 100:9173-9178 (2003); Wada et al., *J Biol. Chem.* 278:30022-30027 (2003)). The ispE genes from above organism were cloned and expressed, and the recombinant proteins were purified for crystallization. The following genes can be used for Step C conversion:

| Protein | GenBank ID | GI Number | Organism |
| --- | --- | --- | --- |
| ispE | P62615.1 | 50402174 | *Escherichia coli* strain K12 |
| ispE | P83700.1 | 51316201 | *Thermus thermophilus* HB8 |
| ispE | O67060.1 | 6919911 | *Aquifex aeolicus* |

Erythritol 2,4-Cyclodiphosphate Synthase (FIG. 3, Step D)

In Step D of the pathway, 2-phospho-4-(cytidine 5'-diphospho)-erythritol is converted to erythritol-2,4-cyclodiphosphate by the Erythritol 2,4-cyclodiphosphate synthase. The exact enzyme for this step has not been identified. However, enzymes catalyzing similar reactions can be applied to this step. An example is the 2-C-methyl-D-erythritol 2,4-cyclodiphosphate synthase (EC 4.6.1.12). The 2-C-methyl-D-erythritol 2,4-cyclodiphosphate synthase is also in the methylerythritol phosphate pathway for the isoprenoid biosynthesis and catalyzes the conversion between 2-phospho-4-(cytidine 5' diphospho)-2-C-methyl-D-erythritol and 2-C-methyl-D-erythritol-2,4-cyclodiphosphate, with an extra methyl group comparing to step D conversion. The 2-C-methyl-D-erythritol 2,4-cyclodiphosphate synthase is encoded by ispF gene and the crystal structures of *Escherichia coli, Thermus thermophilus, Haemophilus influenzae*, and *Campylobacter jejuni* IspF were determined (Richard et al., *J Biol. Chem.* 277:8667-8672 (2002); Steinbacher et al., *J Mol. Biol.* 316:79-88 (2002); Lehmann et al., *Proteins* 49:135-138 (2002); Kishida et al., *Acta Crystallogr. D. Biol. Crystallogr.* 59:23-31 (2003); Gabrielsen et al., *J Biol. Chem.* 279:52753-52761 (2004)). The ispF genes from above organism were cloned and expressed, and the recombinant proteins were purified for crystallization. The following genes can be used for Step D conversion:

| Protein | GenBank ID | GI Number | Organism |
| --- | --- | --- | --- |
| ispF | P62617.1 | 51317402 | *Escherichia coli* strain K12 |
| ispF | Q8RQP5.1 | 51701599 | *Thermus thermophilus* HB8 |
| ispF | P44815.1 | 1176081 | *Haemophilus influenzae* |
| ispF | Q9PM68.1 | 12230305 | *Campylobacter jejuni* |

1-Hydroxy-2-Butenyl 4-Diphosphate Synthase (FIG. 3, Step E)

Step E of FIG. 3 entails conversion of erythritol-2,4-cyclodiphosphate to 1-hydroxy-2-butenyl 4-diphosphate by 1-hydroxy-2-butenyl 4-diphosphate synthase. An enzyme with this activity has not been characterized to date. This transformation is analogous to the reduction of 2-C-methyl-D-erythritol-2,4-cyclodiphosphate to 1-hydroxy-2-methyl-2-(E)-butenyl 4-diphosphate by (E)-4-hydroxy-3-methylbut-2-enyl-diphosphate synthase (EC 1.17.7.1). This enzyme is an iron-sulfur protein that participates in the non-mevalonate pathway for isoprenoid biosynthesis found in bacteria and plants. Most bacterial enzymes including the *E. coli* enzyme, encoded by ispG, utilize reduced ferredoxin or flavodoxin as an electron donor (Zepeck et al., *J Org. Chem.* 70:9168-9174 (2005)). An analogous enzyme from the thermophilic cyanobacterium *Thermosynechococcus elongatus* BP-1, encoded by gcpE, was heterologously expressed and characterized in *E. coli* (Okada et al., *J Biol. Chem.* 280:20672-20679 (2005)). Additional enzyme candidates from *Thermus thermophilus* and *Arabidopsis thaliana* have been characterized and expressed in *E. coli* (Seemann et al., *J Biol. Inorg. Chem.* 10:131-137 (2005); Kollas et al., *FEBS Lett.* 532:432-436 (2002)).

| Protein | GenBank ID | GI Number | Organism |
| --- | --- | --- | --- |
| ispG | NP_417010.1 | 16130440 | *Escherichia coli* |
| gcpE | NP_681786.1 | 22298539 | *Thermosynechococcus elongatus* |
| gcpE | AAO21364.1 | 27802077 | *Thermus thermophilus* |
| gcpE | AAO15446.1 | 27462472 | *Arabidopsis thaliana* |

1-Hydroxy-2-Butenyl 4-Diphosphate Reductase (FIG. 3, Step F)

The concurrent dehydration and reduction of 1-hydroxy-2-butenyl 4-diphosphate is catalyzed by an enzyme with 1-hydroxy-2-butenyl 4-diphosphate reductase activity (FIG. 3, Step F). Such an enzyme will form a mixture of products, butenyl 4-diphosphate or 2-butenyl 4-diphosphate. An analogous reaction is catalyzed by 4-hydroxy-3-methylbut-2-enyl diphosphate reductase (EC 1.17.1.2) in the non-mevalonate pathway for isoprenoid biosynthesis. This enzyme is an iron-sulfur protein that utilizes reduced ferredoxin or flavodoxin as an electron donor. Maximal activity of 4-hydroxy-3-methylbut-2-enyl diphosphate reductase *E. coli*, encoded by ispH, requires both flavodoxin and flavodoxin reductase (Wolff et al., *FEBS Lett.* 541:115-120 (2003); Grawert et al., *J Am. Chem. Soc.* 126:12847-12855 (2004)). In the characterized catalytic system, reduced flavodoxin is regenerated by the NAD(P)+-dependent flavodoxin reductase. The enzyme from *Aquifex aeolicus*, encoded by lytB, was expressed as a His-tagged enzyme in *E. coli* and characterized (Altincicek et al., *FEBS Lett.* 532:437-440 (2002)). An analogous enzyme in plants is encoded by hdr of *Arabidopsis thaliana* (Botella-Pavia et al., *Plant J* 40:188-199 (2004)).

| Protein | GenBank ID | GI Number | Organism |
| --- | --- | --- | --- |
| ispH | AAL38655.1 | 18652795 | *Escherichia coli* |
| lytB | O67625.1 | 8928180 | *Aquifex aeolicus* |
| hdr | NP_567965.1 | 18418433 | *Arabidopsis thaliana* |

Altering the expression level of genes involved in iron-sulfur cluster formation can have an advantageous effect on the activities of iron-sulfur proteins in the proposed pathways (for example, enzymes required in Steps E and F of FIG. 3). In *E. coli*, it was demonstrated that overexpression of the iron-sulfur containing protein IspH (analogous to Step F of FIG. 3) is enhanced by coexpression of genes from the isc region involved in assembly of iron-sulfur clusters (Grawert et al., *J Am. Chem. Soc.* 126:12847-12855 (2004)). The gene cluster is composed of the genes icsS, icsU, icsA, hscB, hscA and fdx. Overexpression of these genes was shown to improve the synthetic capability of the iron-sulfur assembly pipeline, required for functional expression of iron-sulfur proteins. A similar approach can be applicable in the current application.

| Protein | GenBank ID | GI Number | Organism |
|---|---|---|---|
| iscS | AAT48142.1 | 48994898 | *Escherichia coli* |
| iscU | AAC75582.1 | 1788878 | *Escherichia coli* |
| iscA | AAC75581.1 | 1788877 | *Escherichia coli* |
| hscB | AAC75580.1 | 1788876 | *Escherichia coli* |
| hscA | AAC75579.1 | 1788875 | *Escherichia coli* |
| fdx | AAC75578.1 | 1788874 | *Escherichia coli* |

Butenyl 4-Diphosphate Isomerase (FIG. 3, Step G)

Butenyl 4-diphosphate isomerase catalyzes the reversible interconversion of 2-butenyl-4-diphosphate and butenyl-4-diphosphate. The following enzymes can naturally possess this activity or can be engineered to exhibit this activity. Useful genes include those that encode enzymes that interconvert isopenenyl diphosphate and dimethylallyl diphosphate. These include isopentenyl diphosphate isomerase enzymes from *Escherichia coli* (Rodríguez-Concepción et al., FEBS Lett, 473(3):328-332), *Saccharomyces cerevisiae* (Anderson et al., J Biol Chem, 1989, 264(32); 19169-75), and *Sulfolobus shibatae* (Yamashita et al, Eur J Biochem, 2004, 271(6); 1087-93). The reaction mechanism of isomerization, catalyzed by the Idi protein of *E. coli*, has been characterized in mechanistic detail (de Ruyck et al., *J Biol. Chem.* 281: 17864-17869 (2006)). Isopentenyl diphosphate isomerase enzymes from *Saccharomyces cerevisiae, Bacillus subtilis* and *Haematococcus pluvialis* have been heterologously expressed in *E. coli* (Laupitz et al., *Eur. J Biochem.* 271:2658-2669 (2004); Kajiwara et al., *Biochem. J* 324 (Pt 2):421-426 (1997)).

| Protein | GenBank ID | GI Number | Organism |
|---|---|---|---|
| Idi | NP_417365.1 | 16130791 | *Escherichia coli* |
| IDI1 | NP_015208.1 | 6325140 | *Saccharomyces cerevisiae* |
| Idi | BAC82424.1 | 34327946 | *Sulfolobus shibatae* |
| Idi | AAC32209.1 | 3421423 | *Haematococcus pluvialis* |
| Idi | BAB32625.1 | 12862826 | *Bacillus subtilis* |

Butadiene Synthase (FIG. 3, Step H)

Butadiene synthase catalyzes the conversion of 2-butenyl-4-diphosphate to 1,3-butadiene. The enzymes described below naturally possess such activity or can be engineered to exhibit this activity. Isoprene synthase naturally catalyzes the conversion of dimethylallyl diphosphate to isoprene, but can also catalyze the synthesis of 1,3-butadiene from 2-butenyl-4-diphosphate. Isoprene synthases can be found in several organisms including *Populus alba* (Sasaki et al., FEBS Letters, 579 (11), 2514-2518 (2005)), *Pueraria montana* (Lindberg et al., *Metabolic Eng,* 12(1):70-79 (2010); Sharkey et al., *Plant Physiol.,* 137(2):700-712 (2005)), and *Populus tremula×Populus alba* (Miller et al., *Planta,* 213(3):483-487 (2001)). Additional isoprene synthase enzymes are described in (Chotani et al., WO/2010/031079, Systems Using Cell Culture for Production of Isoprene; Cervin et al., US Patent Application 20100003716, Isoprene Synthase Variants for Improved Microbial Production of Isoprene).

| Protein | GenBank ID | GI Number | Organism |
|---|---|---|---|
| ispS | BAD98243.1 | 63108310 | *Populus alba* |
| ispS | AAQ84170.1 | 35187004 | *Pueraria montana* |
| ispS | CAC35696.1 | 13539551 | *Populus tremula* × *Populus alba* |

Erythrose-4-Phosphate Kinase (FIG. 3, Step I)

In Step I of the pathway, erythrose-4-phosphate is converted to erythrose by the erythrose-4-phosphate kinase. In industrial fermentative production of erythritol by yeasts, glucose was converted to erythrose-4-phosphate through the pentose phosphate pathway and erythrose-4-phosphate was dephosphorylated and reduced to produce erythritol (Moon et al., *Appl. Microbiol Biotechnol.* 86:1017-1025 (2010)). Thus, erythrose-4-phosphate kinase is present in many of these erythritol-producing yeasts, including *Trichosporonoides megachiliensis* SN-G42(Sawada et al., *J Biosci. Bioeng.* 108: 385-390 (2009)), *Candida magnolia* (Kohl et al., *Biotechnol. Lett.* 25:2103-2105 (2003)), and *Torula* sp. (HAJNY et al., *Appl. Microbiol* 12:240-246 (1964); Oh et al., *J Ind. Microbiol Biotechnol.* 26:248-252 (2001)). However, the erythrose-4-phosphate kinase genes were not identified yet. There are many polyol phosphotransferases with wide substrate range that can be applied to this step. An example is the triose kinase (EC 2.7.1.28) catalyzing the reversible conversion between glyceraldehydes and glyceraldehydes-3-phosphate, which are one carbon shorter comparing to Step I. Other examples include the xylulokinase (EC 2.7.1.17) or arabinokinase (EC 2.7.1.54) that catalyzes phosphorylation of 5C polyol aldehyde. The following genes can be used for Step I conversion:

| Protein | GenBank ID | GI Number | Organism |
|---|---|---|---|
| xylB | P09099.1 | 139849 | *Escherichia coli* strain K12 |
| xks1 | P42826.2 | 1723736 | *Saccharomyces cerevisiae* |
| xylB | P29444.1 | 267426 | *Klebsiella pneumoniae* |
| dak1 | Q9HFC5 | 74624685 | *Zygosaccharomyces rouxii* |

Erythrose Reductase (FIG. 3, Step J)

In Step J of the pathway, erythrose is converted to erythritol by the erythrose reductase. In industrial fermentative production of erythritol by yeasts, glucose was converted to erythrose-4-phosphate through the pentose phosphate pathway and erythrose-4-phosphate was dephosphorylated and reduced to produce erythritol (Moon et al., supra, (2010)). Thus, erythrose reductase is present in many of these erythritol-producing yeasts, including *Trichosporonoides megachiliensis* SN-G42 (Sawada et al., supra, (2009)), *Candida magnolia* (Kohl et al., supra, (2003)), and *Torula* sp. (HAJNY et al., supra, (1964); Oh et al., supra, (2001)). Erythrose reductase was characterized and purified from *Torula corallina* (Lee et al., *Biotechnol. Prog.* 19:495-500 (2003); Lee et al., *Appl. Environ. Microbiol* 68:4534-4538 (2002)), *Candida magnolia* (Lee et al., *Appl. Environ. Microbiol* 69:3710-3718 (2003)) and *Trichosporonoides megachiliensis* SN-G42 (Sawada et al., supra, (2009)). Several erythrose reductase genes were cloned and can be applied to Step J. The following genes can be used for Step J conversion:

| Protein | GenBank ID | GI Number | Organism |
| --- | --- | --- | --- |
| alr | ACT78580.1 | 254679867 | Candida magnoliae |
| er1 | BAD90687.1 | 60458781 | Trichosporonoides megachiliensis |
| er2 | BAD90688.1 | 60458783 | Trichosporonoides megachiliensis |
| er3 | BAD90689.1 | 60458785 | Trichosporonoides megachiliensis |

Erythritol Kinase (FIG. 3, Step K)

In Step K of the pathway, erythritol is converted to erythritol-4-phosphate by the erythritol kinase. Erythritol kinase (EC 2.7.1.27) catalyzes the phosphorylation of erythritol. Erythritol kinase was characterized in erythritol utilizing bacteria such as Brucella abortus (Sperry et al., J Bacteriol. 121:619-630 (1975)). The eryA gene of Brucella abortus has been functionally expressed in Escherichia coli and the resultant EryA was shown to catalyze the ATP-dependent conversion of erythritol to erythritol-4-phosphate (Lillo et al., Bioorg. Med. Chem. Lett. 13:737-739 (2003)). The following genes can be used for Step K conversion:

| Protein | GenBank ID | GI Number | Organism |
| --- | --- | --- | --- |
| eryA | Q8YCU8 | 81850596 | Brucella melitensis |
| eriA | Q92NH0 | 81774560 | Sinorhizobium meliloti |
| eryA | YP_001108625.1 | 134102964 | Saccharopolyspora erythraea NRRL 2338 |

Malonyl-CoA:Acetyl-CoA Acyltransferase (FIG. 4, Step A)

In Step A of the pathway described in FIG. 4, malonyl-CoA and acetyl-CoA are condensed to form 3-oxoglutaryl-CoA by malonyl-CoA:acetyl-CoA acyl transferase, a beta-keothiolase. Although no enzyme with activity on malonyl-CoA has been reported to date, a good candidate for this transformation is beta-ketoadipyl-CoA thiolase (EC 2.3.1.174), also called 3-oxoadipyl-CoA thiolase that converts beta-ketoadipyl-CoA to succinyl-CoA and acetyl-CoA, and is a key enzyme of the beta-ketoadipate pathway for aromatic compound degradation. The enzyme is widespread in soil bacteria and fungi including Pseudomonas putida (Harwood et al., J Bacteriol. 176:6479-6488 (1994)) and Acinetobacter calcoaceticus (Doten et al., J Bacteriol. 169:3168-3174 (1987)). The gene products encoded by pcaF in Pseudomonas strain B13 (Kaschabek et al., J Bacteriol. 184:207-215 (2002)), phaD in Pseudomonas putida U (Olivera et al., supra, (1998)), paaE in Pseudomonas fluorescens ST (Di Gennaro et al., Arch Microbiol. 88:117-125 (2007)), and paaJ from E. coli (Nogales et al., Microbiology, 153:357-365 (2007)) also catalyze this transformation. Several beta-ketothiolases exhibit significant and selective activities in the oxoadipyl-CoA forming direction including bkt from Pseudomonas putida, pcaF and bkt from Pseudomonas aeruginosa PAO1, bkt from Burkholderia ambifaria AMMD, paaJ from E. coli, and phaD from P. putida. These enzymes can also be employed for the synthesis of 3-oxoglutaryl-CoA, a compound structurally similar to 3-oxoadipyl-CoA.

| Protein | GenBank ID | GI Number | Organism |
| --- | --- | --- | --- |
| paaJ | NP_415915.1 | 16129358 | Escherichia coli |
| pcaF | AAL02407 | 17736947 | Pseudomonas knackmussii |
| | | | (B13) |
| phaD | AAC24332.1 | 3253200 | Pseudomonas putida |
| pcaF | AAA85138.1 | 506695 | Pseudomonas putida |
| pcaF | AAC37148.1 | 141777 | Acinetobacter calcoaceticus |
| paaE | ABF82237.1 | 106636097 | Pseudomonas fluorescens |
| bkt | YP_777652.1 | 115360515 | Burkholderia ambifaria AMMD |
| bkt | AAG06977.1 | 9949744 | Pseudomonas aeruginosa PAO1 |
| pcaF | AAG03617.1 | 9946065 | Pseudomonas aeruginosa PAO1 |

Another relevant beta-ketothiolase is oxopimeloyl-CoA:glutaryl-CoA acyltransferase (EC 2.3.1.16) that combines glutaryl-CoA and acetyl-CoA to form 3-oxopimeloyl-CoA. An enzyme catalyzing this transformation is found in Ralstonia eutropha (formerly known as Alcaligenes eutrophus), encoded by genes bktB and bktC (Slater et al., J. Bacteriol. 180:1979-1987 (1998); Haywood et al., FEMS Microbiology Letters 52:91-96 (1988)). The sequence of the BktB protein is known; however, the sequence of the BktC protein has not been reported. The pim operon of Rhodopseudomonas palustris also encodes a beta-ketothiolase, encoded by pimA, predicted to catalyze this transformation in the degradative direction during benzoyl-CoA degradation (Harrison et al., Microbiology 151:727-736 (2005)). A beta-ketothiolase enzyme candidate in S. aciditrophicus was identified by sequence homology to bktB (43% identity, evalue=1e-93).

| Protein | GenBank ID | GI Number | Organism |
| --- | --- | --- | --- |
| bktB | YP_725948 | 11386745 | Ralstonia eutropha |
| pimB | CAE29156 | 39650633 | Rhodopseudomonas palustris |
| syn_02642 | YP_462685.1 | 85860483 | Syntrophus aciditrophicus |

Beta-ketothiolase enzymes catalyzing the formation of beta-ketovaleryl-CoA from acetyl-CoA and propionyl-CoA can also be able to catalyze the formation of 3-oxoglutaryl-CoA. Zoogloea ramigera possesses two ketothiolases that can form β-ketovaleryl-CoA from propionyl-CoA and acetyl-CoA and R. eutropha has a β-oxidation ketothiolase that is also capable of catalyzing this transformation (Slater et al., J. Bacteriol, 180:1979-1987 (1998)). The sequences of these genes or their translated proteins have not been reported, but several candidates in R. eutropha, Z. ramigera, or other organisms can be identified based on sequence homology to bktB from R. eutropha. These include:

| Protein | GenBank ID | GI Number | Organism |
| --- | --- | --- | --- |
| phaA | YP_725941.1 | 113867452 | Ralstonia eutropha |
| h16_A1713 | YP_726205.1 | 113867716 | Ralstonia eutropha |
| pcaF | YP_728366.1 | 116694155 | Ralstonia eutropha |
| h16_B1369 | YP_840888.1 | 116695312 | Ralstonia eutropha |
| h16_A0170 | YP_724690.1 | 113866201 | Ralstonia eutropha |
| h16_A0462 | YP_724980.1 | 113866491 | Ralstonia eutropha |
| h16_A1528 | YP_726028.1 | 113867539 | Ralstonia eutropha |
| h16_B0381 | YP_728545.1 | 116694334 | Ralstonia eutropha |
| h16_B0662 | YP_728824.1 | 116694613 | Ralstonia eutropha |
| h16_B0759 | YP_728921.1 | 116694710 | Ralstonia eutropha |
| h16_B0668 | YP_728830.1 | 116694619 | Ralstonia eutropha |
| h16_A1720 | YP_726212.1 | 113867723 | Ralstonia eutropha |
| h16_A1887 | YP_726356.1 | 113867867 | Ralstonia eutropha |
| phbA | P07097.4 | 135759 | Zoogloea ramigera |
| bktB | YP_002005382.1 | 194289475 | Cupriavidus taiwanensis |
| Rmet_1362 | YP_583514.1 | 94310304 | Ralstonia metallidurans |
| Bphy_0975 | YP_001857210.1 | 186475740 | Burkholderia phymatum |

Additional candidates include beta-ketothiolases that are known to convert two molecules of acetyl-CoA into acetoacetyl-CoA (EC 2.1.3.9). Exemplary acetoacetyl-CoA thiolase enzymes include the gene products of atoB from *E. coli* (Martin et al., supra, (2003)), thlA and thlB from *C. acetobutylicum* (Hanai et al., supra, (2007); Winzer et al., supra, (2000)), and ERG10 from *S. cerevisiae* (Hiser et al., supra, (1994)).

| Protein | GenBank ID | GI Number | Organism |
|---|---|---|---|
| toB | NP_416728 | 16130161 | *Escherichia coli* |
| thlA | NP_349476.1 | 15896127 | *Clostridium acetobutylicum* |
| thlB | NP_149242.1 | 15004782 | *Clostridium acetobutylicum* |
| ERG10 | NP_015297 | 6325229 | *Saccharomyces cerevisiae* |

3-Oxoglutaryl-CoA Reductase (Ketone-Reducing) (FIG. 4, Step B)

This enzyme catalyzes the reduction of the 3-oxo group in 3-oxoglutaryl-CoA to the 3-hydroxy group in Step B of the pathway shown in FIG. 4.

3-Oxoacyl-CoA dehydrogenase enzymes convert 3-oxoacyl-CoA molecules into 3-hydroxyacyl-CoA molecules and are often involved in fatty acid beta-oxidation or phenylacetate catabolism. For example, subunits of two fatty acid oxidation complexes in *E. coli*, encoded by fadB and fadJ, function as 3-hydroxyacyl-CoA dehydrogenases (Binstock et al., *Methods Enzymol.* 71 Pt C:403-411 (1981)). Furthermore, the gene products encoded by phaC in *Pseudomonas putida* U (Olivera et al., supra, (1998)) and paaC in *Pseudomonas fluorescens* ST (Di et al., supra, (2007)) catalyze the reversible oxidation of 3-hydroxyadipyl-CoA to form 3-oxoadipyl-CoA, during the catabolism of phenylacetate or styrene. In addition, given the proximity in *E. coli* of paaH to other genes in the phenylacetate degradation operon (Nogales et al., supra, (2007)) and the fact that paaH mutants cannot grow on phenylacetate (Ismail et al., supra, (2003)), it is expected that the *E. coli* paaH gene encodes a 3-hydroxyacyl-CoA dehydrogenase.

| Protein | GenBank ID | GI Number | Organism |
|---|---|---|---|
| fadB | P21177.2 | 119811 | *Escherichia coli* |
| fadJ | P77399.1 | 3334437 | *Escherichia coli* |
| paaH | NP_415913.1 | 16129356 | *Escherichia coli* |
| phaC | NP_745425.1 | 26990000 | *Pseudomonas putida* |
| paaC | ABF82235.1 | 106636095 | *Pseudomonas fluorescens* |

3-Hydroxybutyryl-CoA dehydrogenase, also called acetoacetyl-CoA reductase, catalyzes the reversible NAD(P) H-dependent conversion of acetoacetyl-CoA to 3-hydroxybutyryl-CoA. This enzyme participates in the acetyl-CoA fermentation pathway to butyrate in several species of *Clostridia* and has been studied in detail (Jones and Woods, supra, (1986)). Enzyme candidates include hbd from *C. acetobutylicum* (Boynton et al., *J. Bacteriol.* 178:3015-3024 (1996)), hbd from *C. beijerinckii* (Colby et al., *Appl Environ. Microbiol* 58:3297-3302 (1992)), and a number of similar enzymes from *Metallosphaera sedula* (Berg et al., supra, (2007)). The enzyme from *Clostridium acetobutylicum*, encoded by hbd, has been cloned and functionally expressed in *E. coli* (Youngleson et al., supra, (1989)). Yet other genes demonstrated to reduce acetoacetyl-CoA to 3-hydroxybutyryl-CoA are phbB from *Zoogloea ramigera* (Ploux et al., supra, (1988)) and phaB from *Rhodobacter sphaeroides* (Alber et al., supra, (2006)). The former gene is NADPH-dependent, its nucleotide sequence has been determined (Peoples and Sinskey, supra, (1989)) and the gene has been expressed in *E. coli*. Additional genes include hbd1 (C-terminal domain) and hbd2 (N-terminal domain) in *Clostridium kluyveri* (Hillmer and Gottschalk, *Biochim. Biophys. Acta* 3334:12-23 (1974)) and HSD17B10 in *Bos taurus* (WAKIL et al., supra, (1954)).

| Protein | GenBank ID | GI Number | Organism |
|---|---|---|---|
| hbd | NP_349314.1 | 15895965 | *Clostridium acetobutylicum* |
| hbd | AAM14586.1 | 20162442 | *Clostridium beijerinckii* |
| Msed_1423 | YP_001191505 | 146304189 | *Metallosphaera sedula* |
| Msed_0399 | YP_001190500 | 146303184 | *Metallosphaera sedula* |
| Msed_0389 | YP_001190490 | 146303174 | *Metallosphaera sedula* |
| Msed_1993 | YP_001192057 | 146304741 | *Metallosphaera sedula* |
| hbd2 | EDK34807.1 | 146348271 | *Clostridium kluyveri* |
| hbd1 | EDK32512.1 | 146345976 | *Clostridium kluyveri* |
| HSD17B10 | O02691.3 | 3183024 | *Bos taurus* |
| phaB | YP_353825.1 | 77464321 | *Rhodobacter sphaeroides* |
| phbB | P23238.1 | 130017 | *Zoogloea ramigera* |

3-Hydroxyglutaryl-CoA Reductase (Aldehyde Forming) (FIG. 4, Step C)

3-hydroxyglutaryl-CoA reductase reduces 3-hydroxyglutaryl-CoA to 3-hydroxy-5-oxopentanoate. Several acyl-CoA dehydrogenases reduce an acyl-CoA to its corresponding aldehyde (EC 1.2.1). Exemplary genes that encode such enzymes include the *Acinetobacter calcoaceticus* acr1 encoding a fatty acyl-CoA reductase (Reiser and Somerville, supra, (1997)), the *Acinetobacter* sp. M-1 fatty acyl-CoA reductase (Ishige et al., supra, (2002)), and a CoA- and NADP-dependent succinate semialdehyde dehydrogenase encoded by the sucD gene in *Clostridium kluyveri* (Sohling and Gottschalk, supra, (1996); Sohling and Gottschalk, supra, (1996)). SucD of *P. gingivalis* is another succinate semialdehyde dehydrogenase (Takahashi et al., supra, (2000)). The enzyme acylating acetaldehyde dehydrogenase in *Pseudomonas* sp, encoded by bphG, is yet another as it has been demonstrated to oxidize and acylate acetaldehyde, propionaldehyde, butyraldehyde, isobutyraldehyde and formaldehyde (Powlowski et al., supra, (1993)). In addition to reducing acetyl-CoA to ethanol, the enzyme encoded by adhE in *Leuconostoc mesenteroides* has been shown to oxidize the branched chain compound isobutyraldehyde to isobutyryl-CoA (Koo et al., *Biotechnol Lett.* 27:505-510 (2005)). Butyraldehyde dehydrogenase catalyzes a similar reaction, conversion of butyryl-CoA to butyraldehyde, in solventogenic organisms such as *Clostridium saccharoperbutylacetonicum* (Kosaka et al., *Biosci. Biotechnol Biochem.* 71:58-68 (2007)).

| Protein | GenBank ID | GI Number | Organism |
|---|---|---|---|
| acr1 | YP_047869.1 | 50086359 | *Acinetobacter calcoaceticus* |
| acr1 | AAC45217 | 1684886 | *Acinetobacter baylyi* |
| acr1 | BAB85476.1 | 18857901 | *Acinetobacter* sp. Strain M-1 |
| sucD | P38947.1 | 172046062 | *Clostridium kluyveri* |
| sucD | NP_904963.1 | 34540484 | *Porphyromonas gingivalis* |
| bphG | BAA03892.1 | 425213 | *Pseudomonas* sp |
| adhE | AAV66076.1 | 55818563 | *Leuconostoc mesenteroides* |

| Protein | GenBank ID | GI Number | Organism |
|---|---|---|---|
| bld | AAP42563.1 | 31075383 | Clostridium saccharoperbutylacetonicum |

An additional enzyme type that converts an acyl-CoA to its corresponding aldehyde is malonyl-CoA reductase which transforms malonyl-CoA to malonic semialdehyde. Malonyl-CoA reductase is a key enzyme in autotrophic carbon fixation via the 3-hydroxypropionate cycle in thermoacidophilic archael bacteria (Berg et al., supra, (2007b); Thauer, supra, (2007)). The enzyme utilizes NADPH as a cofactor and has been characterized in *Metallosphaera* and *Sulfolobus* spp (Alber et al., supra, (2006); Hugler et al., supra, (2002)). The enzyme is encoded by Msed_0709 in *Metallosphaera sedula* (Alber et al., supra, (2006); Berg et al., supra, (2007b)). A gene encoding a malonyl-CoA reductase from *Sulfolobus tokodaii* was cloned and heterologously expressed in *E. coli* (Alber et al., supra, (2006)). This enzyme has also been shown to catalyze the conversion of methylmalonyl-CoA to its corresponding aldehyde (WO/2007/141208). Although the aldehyde dehydrogenase functionality of these enzymes is similar to the bifunctional dehydrogenase from *Chloroflexus aurantiacus*, there is little sequence similarity. Both malonyl-CoA reductase enzyme candidates have high sequence similarity to aspartate-semialdehyde dehydrogenase, an enzyme catalyzing the reduction and concurrent dephosphorylation of aspartyl-4-phosphate to aspartate semialdehyde. Additional gene candidates can be found by sequence homology to proteins in other organisms including *Sulfolobus solfataricus* and *Sulfolobus acidocaldarius*. Yet another acyl-CoA reductase (aldehyde forming) candidate is the ald gene from *Clostridium beijerinckii* (Toth et al., *Appl Environ. Microbiol* 65:4973-4980 (1999)). This enzyme has been reported to reduce acetyl-CoA and butyryl-CoA to their corresponding aldehydes. This gene is very similar to eutE that encodes acetaldehyde dehydrogenase of *Salmonella typhimurium* and *E. coli* (Toth et al., supra, (1999)).

| Protein | GenBank ID | GI Number | Organism |
|---|---|---|---|
| MSED_0709 | YP_001190808.1 | 146303492 | Metallosphaera sedula |
| mcr | NP_378167.1 | 15922498 | Sulfolobus tokodaii |
| asd-2 | NP_343563.1 | 15898958 | Sulfolobus solfataricus |
| Saci_2370 | YP_256941.1 | 70608071 | Sulfolobus acidocaldarius |
| Ald | AAT66436 | 9473535 | Clostridium beijerinckii |
| eutE | AAA80209 | 687645 | Salmonella typhimurium |
| eutE | P77445 | 2498347 | Escherichia coli |

3-Hydroxy-5-Oxopentanoate Reductase (FIG. 4, Step D)

This enzyme reduces the terminal aldehyde group in 3-hydroxy-5-oxopentanote to the alcohol group. Exemplary genes encoding enzymes that catalyze the conversion of an aldehyde to alcohol (i.e., alcohol dehydrogenase or equivalently aldehyde reductase, 1.1.1.a) include alrA encoding a medium-chain alcohol dehydrogenase for C2-C14 (Tani et al., supra, (2000)), ADH2 from *Saccharomyces cerevisiae* (Atsumi et al., supra, (2008)), yqhD from *E. coli* which has preference for molecules longer than C(3) (Sulzenbacher et al., supra, (2004)), and bdh I and bdh II from *C. acetobutyli-cum* which converts butyryaldehyde into butanol (Walter et al., supra, (1992)). The gene product of yqhD catalyzes the reduction of acetaldehyde, malondialdehyde, propionaldehyde, butyraldehyde, and acrolein using NADPH as the cofactor (Perez et al., 283:7346-7353 (2008); Perez et al., *J Biol. Chem.* 283:7346-7353 (2008)). The adhA gene product from *Zymomonas mobilis* has been demonstrated to have activity on a number of aldehydes including formaldehyde, acetaldehyde, propionaldehyde, butyraldehyde, and acrolein (Kinoshita et al., *Appl Microbiol Biotechnol* 22:249-254 (1985)).

| Protein | GenBank ID | GI Number | Organism |
|---|---|---|---|
| alrA | BAB12273.1 | 9967138 | Acinetobacter sp. Strain M-1 |
| ADH2 | NP_014032.1 | 6323961 | Saccharomyces cerevisiae |
| yqhD | NP_417484.1 | 16130909 | Escherichia coli |
| bdh I | NP_349892.1 | 15896543 | Clostridium acetobutylicum |
| bdh II | NP_349891.1 | 15896542 | Clostridium acetobutylicum |
| adhA | YP_162971.1 | 56552132 | Zymomonas mobilis |

Enzymes exhibiting 4-hydroxybutyrate dehydrogenase activity (EC 1.1.1.61) also fall into this category. Such enzymes have been characterized in *Ralstonia eutropha* (Bravo et al., supra, (2004)), *Clostridium kluyveri* (Wolff and Kenealy, supra, (1995)) and *Arabidopsis thaliana* (Breitkreuz et al., supra, (2003)). The *A. thaliana* enzyme was cloned and characterized in yeast [12882961]. Yet another gene is the alcohol dehydrogenase adhI from *Geobacillus thermoglucosidasius* (Jeon et al., *J Biotechnol* 135:127-133 (2008)).

| Protein | GenBank ID | GI Number | Organism |
|---|---|---|---|
| 4hbd | YP_726053.1 | 113867564 | Ralstonia eutropha H16 |
| 4hbd | EDK35022.1 | 146348486 | Clostridium kluyveri |
| 4hbd | Q94B07 | 75249805 | Arabidopsis thaliana |
| adhI | AAR91477.1 | 40795502 | Geobacillus thermoglucosidasius |

Another exemplary enzyme is 3-hydroxyisobutyrate dehydrogenase (EC 1.1.1.31) which catalyzes the reversible oxidation of 3-hydroxyisobutyrate to methylmalonate semialdehyde. This enzyme participates in valine, leucine and isoleucine degradation and has been identified in bacteria, eukaryotes, and mammals. The enzyme encoded by P84067 from *Thermus thermophilus* HB8 has been structurally characterized (Lokanath et al., *J Mol Biol* 352:905-17 (2005)). The reversibility of the huma 3-hydroxyisobutyrate dehydrogenase was demonstrated using isotopically-labeled substrate (Manning et al., *Biochem J* 231:481-4 (1985)). Additional genes encoding this enzyme include 3hidh in *Homo sapiens* (Hawes et al., *Methods Enzymol* 324:218-228 (2000)) and *Oryctolagus cuniculus* (Hawes et al., supra, (2000); Chowdhury et al., *Biosci. Biotechnol Biochem.* 60:2043-2047 (1996)), mmsb in *Pseudomonas aeruginosa*, and dhat in *Pseudomonas putida* (Aberhart et al., *J Chem. Soc.* [Perkin I] 6:1404-1406 (1979); Chowdhury et al., supra, (1996); Chowdhury et al., *Biosci. Biotechnol Biochem.* 67:438-441 (2003)).

| Protein | GenBank ID | GI Number | Organism |
|---|---|---|---|
| P84067 | P84067 | 75345323 | Thermus thermophilus |
| mmsb | P28811.1 | 127211 | Pseudomonas aeruginosa |
| dhat | Q59477.1 | 2842618 | Pseudomonas putida |
| 3hidh | P31937.2 | 12643395 | Homo sapiens |
| 3hidh | P32185.1 | 416872 | Oryctolagus cuniculus |

The conversion of malonic semialdehyde to 3-HP can also be accomplished by two other enzymes: NADH-dependent 3-hydroxypropionate dehydrogenase and NADPH-dependent malonate semialdehyde reductase. An NADH-dependent 3-hydroxypropionate dehydrogenase is thought to participate in beta-alanine biosynthesis pathways from propionate in bacteria and plants (Rathinasabapathi B., *Journal of Plant Pathology* 159:671-674 (2002); Stadtman, *J. Am. Chem. Soc.* 77:5765-5766 (1955)). This enzyme has not been associated with a gene in any organism to date. NADPH-dependent malonate semialdehyde reductase catalyzes the reverse reaction in autotrophic CO2-fixing bacteria. Although the enzyme activity has been detected in *Metallosphaera sedula*, the identity of the gene is not known (Alber et al., supra, (2006)).

3,5-Dihydroxypentanoate Kinase (FIG. 4, Step E)

This enzyme phosphorylates 3,5-dihydroxypentanotae in FIG. 4 (Step E) to form 3-hydroxy-5-phosphonatooxypentanoate (3H5PP). This transformation can be catalyzed by enzymes in the EC class 2.7.1 that enable the ATP-dependent transfer of a phosphate group to an alcohol.

A good candidate for this step is mevalonate kinase (EC 2.7.1.36) that phosphorylates the terminal hydroxyl group of the methyl analog, mevalonate, of 3,5-dihydroxypentanote. Some gene candidates for this step are erg12 from *S. cerevisiae*, mvk from *Methanocaldococcus jannaschi*, MVK from *Homo sapeins*, and mvk from *Arabidopsis thaliana* col.

| Protein | GenBank ID | GI Number | Organism |
|---|---|---|---|
| erg12 | CAA39359.1 | 3684 | *Sachharomyces cerevisiae* |
| mvk | Q58487.1 | 2497517 | *Methanocaldococcus jannaschii* |
| mvk | AAH16140.1 | 16359371 | *Homo sapiens* |
| M\mvk | NP_851084.1 | 30690651 | *Arabidopsis thaliana* |

Glycerol kinase also phosphorylates the terminal hydroxyl group in glycerol to form glycerol-3-phosphate. This reaction occurs in several species, including *Escherichia coli*, *Saccharomyces cerevisiae*, and *Thermotoga maritima*. The *E. coli* glycerol kinase has been shown to accept alternate substrates such as dihydroxyacetone and glyceraldehyde (Hayashi and Lin, supra, (1967)). T, maritime has two glycerol kinases (Nelson et al., supra, (1999)). Glycerol kinases have been shown to have a wide range of substrate specificity. Crans and Whiteside studied glycerol kinases from four different organisms (*Escherichia coli*, *S. cerevisiae*, *Bacillus stearothermophilus*, and *Candida mycoderma*) (Crans and Whitesides, supra, (2010); Nelson et al., supra, (1999)). They studied 66 different analogs of glycerol and concluded that the enzyme could accept a range of substituents in place of one terminal hydroxyl group and that the hydrogen atom at C2 could be replaced by a methyl group. Interestingly, the kinetic constants of the enzyme from all four organisms were very similar. The gene candidates are:

| Protein | GenBank ID | GI Number | Organism |
|---|---|---|---|
| glpK | AP_003883.1 | 89110103 | *Escherichia coli* K12 |
| glpK1 | NP_228760.1 | 15642775 | *Thermotoga maritime* MSB8 |
| glpK2 | NP_229230.1 | 15642775 | *Thermotoga maritime* MSB8 |
| Gut1 | NP_011831.1 | 82795252 | *Saccharomyces cerevisiae* |

Homoserine kinase is another possible candidate that can lead to the phosphorylation of 3,5-dihydroxypentanoate. This enzyme is also present in a number of organisms including *E. coli*, *Streptomyces* sp, and *S. cerevisiae*. Homoserine kinase from *E. coli* has been shown to have activity on numerous substrates, including, L-2-amino,1,4-butanediol, aspartate semialdehyde, and 2-amino-5-hydroxyvalerate (Huo and Viola, supra, (1996); Huo and Viola, supra, (1996)). This enzyme can act on substrates where the carboxyl group at the alpha position has been replaced by an ester or by a hydroxymethyl group. The gene candidates are:

| Protein | GenBank ID | GI Number | Organism |
|---|---|---|---|
| thrB | BAB96580.2 | 85674277 | *Escherichia coli* K12 |
| SACT1DRAFT_4809 | ZP_06280784.1 | 282871792 | *Streptomyces* sp. ACT-1 |
| Thr1 | AAA35154.1 | 172978 | *Saccharomyces serevisiae* |

3H5PP Kinase (FIG. 4, Step F)

Phosphorylation of 3H5PP to 3H5PDP is catalyzed by 3H5PP kinase (FIG. 4, Step F). Phosphomevalonate kinase (EC 2.7.4.2) catalyzes the analogous transformation in the mevalonate pathway. This enzyme is encoded by erg8 in *Saccharomyces cerevisiae* (Tsay et al., *Mol. Cell Biol.* 11:620-631 (1991)) and mvaK2 in *Streptococcus pneumoniae*, *Staphylococcus aureus* and *Enterococcus faecalis* (Doun et al., *Protein Sci.* 14:1134-1139 (2005); Wilding et al., *J Bacteriol.* 182:4319-4327 (2000)). The *Streptococcus pneumoniae* and *Enterococcus faecalis* enzymes were cloned and characterized in *E. coli* (Pilloff et al., *J Biol. Chem.* 278:4510-4515 (2003); Doun et al., *Protein Sci.* 14:1134-1139 (2005)).

| Protein | GenBank ID | GI Number | Organism |
|---|---|---|---|
| Erg8 | AAA34596.1 | 171479 | *Saccharomyces cerevisiae* |
| mvaK2 | AAG02426.1 | 9937366 | *Staphylococcus aureus* |
| mvaK2 | AAG02457.1 | 9937409 | *Streptococcus pneumoniae* |
| mvaK2 | AAG02442.1 | 9937388 | *Enterococcus faecalis* |

3H5PDP Decarboxylase (FIG. 4, Step G)

Butenyl 4-diphosphate is formed from the ATP-dependent decarboxylation of 3H5PDP by 3H5PDP decarboxylase (FIG. 4, Step G). Although an enzyme with this activity has not been characterized to date a similar reaction is catalyzed by mevalonate diphosphate decarboxylase (EC 4.1.1.33), an enzyme participating in the mevalonate pathway for isoprenoid biosynthesis. This reaction is catalyzed by MVD1 in *Saccharomyces cerevisiae*, MVD in *Homo sapiens* and MDD in *Staphylococcus aureus* and *Trypsonoma brucei* (Toth et al., *J Biol. Chem.* 271:7895-7898 (1996); Byres et al., *J Mol. Biol.* 371:540-553 (2007)).

| Protein | GenBank ID | GI Number | Organism |
|---|---|---|---|
| MVD1 | P32377.2 | 1706682 | *Saccharomyces cerevisiae* |
| MVD | NP_002452.1 | 4505289 | *Homo sapiens* |
| MDD | ABQ48418.1 | 147740120 | *Staphylococcus aureus* |
| MDD | EAN78728.1 | 70833224 | *Trypsonoma brucei* |

Butenyl 4-Diphosphate Isomerase (FIG. 4, Step H)

Butenyl 4-diphosphate isomerase catalyzes the reversible interconversion of 2-butenyl-4-diphosphate and butenyl-4-diphosphate. The following enzymes can naturally possess this activity or can be engineered to exhibit this activity. Useful genes include those that encode enzymes that interconvert isopenenyl diphosphate and dimethylallyl diphosphate. These include isopentenyl diphosphate isomerase enzymes from *Escherichia coli* (Rodríguez-Concepción et al., *FEBS Lett*, 473(3):328-332), *Saccharomyces cerevisiae* (Anderson et al., *J Biol Chem*, 1989, 264(32); 19169-75), and *Sulfolobus shibatae* (Yamashita et al, Eur J Biochem, 2004, 271(6); 1087-93). The reaction mechanism of isomerization, catalyzed by the Idi protein of *E. coli*, has been characterized in mechanistic detail (de Ruyck et al., *J Biol. Chem.* 281: 17864-17869 (2006)). Isopentenyl diphosphate isomerase enzymes from *Saccharomyces cerevisiae, Bacillus subtilis* and *Haematococcus pluvialis* have been heterologously expressed in *E. coli* (Laupitz et al., *Eur. J Biochem.* 271:2658-2669 (2004); Kajiwara et al., *Biochem. J* 324 (Pt 2):421-426 (1997)).

| Protein | GenBank ID | GI Number | Organism |
|---|---|---|---|
| Idi | NP_417365.1 | 16130791 | *Escherichia coli* |
| IDI1 | NP_015208.1 | 6325140 | *Saccharomyces cerevisiae* |
| Idi | BAC82424.1 | 34327946 | *Sulfolobus shibatae* |
| Idi | AAC32209.1 | 3421423 | *Haematococcus pluvialis* |
| Idi | BAB32625.1 | 12862826 | *Bacillus subtilis* |

Butadiene Synthase (FIG. 4, Step I)

Butadiene synthase catalyzes the conversion of 2-butenyl-4-diphosphate to 1,3-butadiene. The enzymes described below naturally possess such activity or can be engineered to exhibit this activity. Isoprene synthase naturally catalyzes the conversion of dimethylallyl diphosphate to isoprene, but can also catalyze the synthesis of 1,3-butadiene from 2-butenyl-4-diphosphate. Isoprene synthases can be found in several organisms including *Populus alba* (Sasaki et al., FEBS Letters, 2005, 579 (11), 2514-2518), *Pueraria montana* (Lindberg et al., *Metabolic Eng*, 12(1):70-79 (2010); Sharkey et al., *Plant Physiol.*, 137(2):700-712 (2005)), and *Populus tremula×Populus alba* (Miller et al., *Planta*, 213(3):483-487 (2001)). Additional isoprene synthase enzymes are described in (Chotani et al., WO/2010/031079, Systems Using Cell Culture for Production of Isoprene; Cervin et al., US Patent Application 20100003716, Isoprene Synthase Variants for Improved Microbial Production of Isoprene).

| Protein | GenBank ID | GI Number | Organism |
|---|---|---|---|
| ispS | BAD98243.1 | 63108310 | *Populus alba* |
| ispS | AAQ84170.1 | 35187004 | *Pueraria montana* |
| ispS | CAC35696.1 | 13539551 | *Populus tremula × Populus alba* |

3-Hydroxyglutaryl-CoA Reductase (Alcohol Forming) (FIG. 4, Step J)

This step catalyzes the reduction of the acyl-CoA group in 3-hydroxyglutaryl-CoA to the alcohol group. Exemplary bifunctional oxidoreductases that convert an acyl-CoA to alcohol include those that transform substrates such as acetyl-CoA to ethanol (e.g., adhE from *E. coli* (Kessler et al., supra, (1991)) and butyryl-CoA to butanol (e.g. adhE2 from *C. acetobutylicum* (Fontaine et al., supra, (2002)). In addition to reducing acetyl-CoA to ethanol, the enzyme encoded by adhE in *Leuconostoc mesenteroides* has been shown to oxide the branched chain compound isobutyraldehyde to isobutyryl-CoA (Kazahaya et al., supra, (1972); Koo et al., supra, (2005)).

Another exemplary enzyme can convert malonyl-CoA to 3-HP. An NADPH-dependent enzyme with this activity has characterized in *Chloroflexus aurantiacus* where it participates in the 3-hydroxypropionate cycle (Hugler et al., supra, (2002); Strauss and Fuchs, supra, (1993)). This enzyme, with a mass of 300 kDa, is highly substrate-specific and shows little sequence similarity to other known oxidoreductases (Hugler et al., supra, (2002)). No enzymes in other organisms have been shown to catalyze this specific reaction; however there is bioinformatic evidence that other organisms can have similar pathways (Klatt et al., supra, (2007)). Enzyme candidates in other organisms including *Roseiflexus castenholzii, Erythrobacter* sp. NAP1 and marine gamma proteobacterium HTCC2080 can be inferred by sequence similarity.

| Protein | GenBank ID | GI Number | Organism |
|---|---|---|---|
| adhE | NP_415757.1 | 16129202 | *Escherichia coli* |
| adhE2 | AAK09379.1 | 12958626 | *Clostridium acetobutylicum* |
| adhE | AAV66076.1 | 55818563 | *Leuconostoc mesenteroides* |
| mcr | AAS20429.1 | 42561982 | *Chloroflexus aurantiacus* |
| Rcas_2929 | YP_001433009.1 | 156742880 | *Roseiflexus castenholzii* |
| NAP1_02720 | ZP_01039179.1 | 85708113 | *Erythrobacter* sp. NAP1 |
| MGP2080_00535 | ZP_01626393.1 | 119504313 | marine gamma proteobacterium HTCC2080 |

Longer chain acyl-CoA molecules can be reduced to their corresponding alcohols by enzymes such as the jojoba (*Simmondsia chinensis*) FAR which encodes an alcohol-forming fatty acyl-CoA reductase. Its overexpression in *E. coli* resulted in FAR activity and the accumulation of fatty alcohol (Metz et al., *Plant Physiology* 122:635-644 (2000)).

| Protein | GenBank ID | GI Number | Organism |
|---|---|---|---|
| FAR | AAD38039.1 | 5020215 | *Simmondsia chinensis* |

Another candidate for catalyzing this step is 3-hydroxy-3-methylglutaryl-CoA reductase (or HMG-CoA reductase). This enzyme reduces the CoA group in 3-hydroxy-3-methylglutaryl-CoA to an alcohol forming mevalonate. Gene candidates for this step include:

| Protein | GenBank ID | GI Number | Organism |
|---|---|---|---|
| HMG1 | CAA86503.1 | 587536 | *Saccharomyces cerevisiae* |
| HMG2 | NP_013555 | 6323483 | *Saccharomyces cerevisiae* |
| HMG1 | CAA70691.1 | 1694976 | *Arabidopsis thaliana* |
| hmgA | AAC45370.1 | 2130564 | *Sulfolobus solfataricus* |

The hmgA gene of *Sulfolobus solfataricus*, encoding 3-hydroxy-3-methylglutaryl-CoA reductase, has been cloned, sequenced, and expressed in *E. coli* (Bochar et al., *J Bacteriol.*

179:3632-3638 (1997)). *S. cerevisiae* also has two HMG-CoA reductases in it (Basson et al., *Proc. Natl. Acad. Sci. U.S.A* 83:5563-5567 (1986)). The gene has also been isolated from *Arabidopsis thaliana* and has been shown to complement the HMG-COA reductase activity in *S. cerevisiae* (Learned et al., *Proc. Natl. Acad. Sci. U.S.A* 86:2779-2783 (1989)).

3-Oxoglutaryl-CoA Reductase (Aldehyde Forming) (FIG. 4, Step K)

Several acyl-CoA dehydrogenases are capable of reducing an acyl-CoA to its corresponding aldehyde. Thus they can naturally reduce 3-oxoglutaryl-CoA to 3,5-dioxopentanoate or can be engineered to do so. Exemplary genes that encode such enzymes were discussed in FIG. 4, Step C.

3,5-Dioxopentanoate Reductase (Ketone Reducing) (FIG. 4, Step L)

There exist several exemplary alcohol dehydrogenases that convert a ketone to a hydroxyl functional group. Two such enzymes from *E. coli* are encoded by malate dehydrogenase (mdh) and lactate dehydrogenase (ldhA). In addition, lactate dehydrogenase from *Ralstonia eutropha* has been shown to demonstrate high activities on 2-ketoacids of various chain lengths including lactate, 2-oxobutyrate, 2-oxopentanoate and 2-oxoglutarate (Steinbuchel et al., *Eur. J. Biochem.* 130:329-334 (1983)). Conversion of alpha-ketoadipate into alpha-hydroxyadipate can be catalyzed by 2-ketoadipate reductase, an enzyme reported to be found in rat and in human placenta (Suda et al., *Arch. Biochem. Biophys.* 176:610-620 (1976); Suda et al., *Biochem. Biophys. Res. Commun.* 77:586-591 (1977)). An additional candidate for this step is the mitochondrial 3-hydroxybutyrate dehydrogenase (bdh) from the human heart which has been cloned and characterized (Marks et al., *J. Biol. Chem.* 267:15459-15463 (1992)). This enzyme is a dehydrogenase that operates on a 3-hydroxyacid. Another exemplary alcohol dehydrogenase converts acetone to isopropanol as was shown in *C. beijerinckii* (Ismaiel et al., *J. Bacteriol.* 175:5097-5105 (1993)) and *T. brockii* (Lamed et al., *Biochem. J.* 195:183-190 (1981); Peretz et al., *Biochemistry.* 28:6549-6555 (1989)). Methyl ethyl ketone reductase, or alternatively, 2-butanol dehydrogenase, catalyzes the reduction of MEK to form 2-butanol. Exemplary enzymes can be found in *Rhodococcus ruber* (Kosjek et al., *Biotechnol Bioeng.* 86:55-62 (2004)) and *Pyrococcus furiosus* (van der et al., *Eur. J. Biochem.* 268:3062-3068 (2001)).

| Protein | GenBank ID | GI Number | Organism |
| --- | --- | --- | --- |
| mdh | AAC76268.1 | 1789632 | *Escherichia coli* |
| ldhA | NP_415898.1 | 16129341 | *Escherichia coli* |
| ldh | YP_725182.1 | 113866693 | *Ralstonia eutropha* |
| bdh | AAA58352.1 | 177198 | *Homo sapiens* |
| adh | AAA23199.2 | 60592974 | *Clostridium beijerinckii* NRRL B593 |
| adh | P14941.1 | 113443 | *Thermoanaerobacter brockii* HTD4 |
| adhA | AAC25556 | 3288810 | *Pyrococcus furiosus* |
| adh-A | CAD36475 | 21615553 | *Rhodococcus ruber* |

A number of organisms can catalyze the reduction of 4-hydroxy-2-butanone to 1,3-butanediol, including those belonging to the genus *Bacillus, Brevibacterium, Candida,* and *Klebsiella* among others, as described by Matsuyama et al. U.S. Pat. No. 5,413,922. A mutated *Rhodococcus* phenylacetaldehyde reductase (Sar268) and a Leifonia alcohol dehydrogenase have also been shown to catalyze this transformation at high yields (Itoh et al., *Appl. Microbiol. Biotechnol.* 75(6):1249-1256).

Homoserine dehydrogenase (EC 1.1.1.13) catalyzes the NAD(P)H-dependent reduction of aspartate semialdehyde to homoserine. In many organisms, including *E. coli*, homoserine dehydrogenase is a bifunctional enzyme that also catalyzes the ATP-dependent conversion of aspartate to aspartyl-4-phosphate (Starnes et al., *Biochemistry* 11:677-687 (1972)). The functional domains are catalytically independent and connected by a linker region (Sibilli et al., *J Biol Chem* 256:10228-10230 (1981)) and both domains are subject to allosteric inhibition by threonine. The homoserine dehydrogenase domain of the *E. coli* enzyme, encoded by thrA, was separated from the aspartate kinase domain, characterized, and found to exhibit high catalytic activity and reduced inhibition by threonine (James et al., *Biochemistry* 41:3720-3725 (2002)). This can be applied to other bifunctional threonine kinases including, for example, hom1 of *Lactobacillus plantarum* (Cahyanto et al., *Microbiology* 152:105-112 (2006)) and *Arabidopsis thaliana*. The monofunctional homoserine dehydrogenases encoded by hom6 in *S. cerevisiae* (Jacques et al., *Biochim Biophys Acta* 1544:28-41 (2001)) and hom2 in *Lactobacillus plantarum* (Cahyanto et al., supra, (2006)) have been functionally expressed and characterized in *E. coli*.

| Protein | GenBank ID | GI number | Organism |
| --- | --- | --- | --- |
| thrA | AAC73113.1 | 1786183 | *Escherichia coli* K12 |
| akthr2 | O81852 | 75100442 | *Arabidopsis thaliana* |
| hom6 | CAA89671 | 1015880 | *Saccharomyces cerevisiae* |
| hom1 | CAD64819 | 28271914 | *Lactobacillus plantarum* |
| hom2 | CAD63186 | 28270285 | *Lactobacillus plantarum* |

3,5-Dioxopentanoate Reductase (Aldehyde Reducing) (FIG. 4, Step M)

Several aldehyde reducing reductases are capable of reducing an aldehyde to its corresponding alcohol. Thus they can naturally reduce 3,5-dioxopentanoate to 5-hydroxy-3-oxopentanoate or can be engineered to do so. Exemplary genes that encode such enzymes were discussed in FIG. 4, Step D.

5-Hydroxy-3-Oxopentanoate Reductase (FIG. 4, Step N)

Several ketone reducing reductases are capable of reducing a ketone to its corresponding hydroxyl group. Thus they can naturally reduce 5-hydroxy-3-oxopentanoate to 3,5-dihydroxypentanoate or can be engineered to do so. Exemplary genes that encode such enzymes were discussed in FIG. 4, Step L.

3-Oxo-Glutaryl-CoA Reductase (CoA Reducing and Alcohol Forming) (FIG. 4, Step O)

3-oxo-glutaryl-CoA reductase (CoA reducing and alcohol forming) enzymes catalyze the 2 reduction steps required to form 5-hydroxy-3-oxopentanoate from 3-oxo-glutaryl-CoA. Exemplary 2-step oxidoreductases that convert an acyl-CoA to an alcohol were provided for FIG. 4, Step J. Such enzymes can naturally convert 3-oxo-glutaryl-CoA to 5-hydroxy-3-oxopentanoate or can be engineered to do so.

EXAMPLE II

Chemical Production of Butadiene from Crotyl Alcohol

In a typical process for converting crotyl alcohol into butadiene, crotyl alcohol is passed, either neat or in a solvent and either in presence or absence of steam, over a solid inorganic, organic or metal-containing dehydration catalyst heated to temperatures in the range 40-400° C. inside of the reaction vessel or tube, leading to elimination of water and release of butadiene as a gas, which is condensed (butadiene bp=−4.4° C.) and collected in a reservoir for further processing, storage, or use. Typical catalysts can include bismuth molybdate, phosphate-phosphoric acid, cerium oxide, kaolin-iron oxide, kaolin-phosphoric acid, silica-alumina, and alumina. Typical process throughputs are in the range of 0.1-20,000 kg/h. Typical solvents are toluene, heptane, octane, ethylbenzene, and xylene.

Throughout this application various publications have been referenced. The disclosures of these publications in their entireties, including GenBank and GI number publications, are hereby incorporated by reference in this application in order to more fully describe the state of the art to which this invention pertains. Although the invention has been described with reference to the examples provided above, it should be understood that various modifications can be made without departing from the spirit of the invention.

What is claimed is:

1. A process for the production of butadiene comprising:
   (a) culturing by fermentation in a sufficient amount of nutrients and media a non-naturally occurring microbial organism that produces crotyl alcohol thereby biosynthetically producing crotyl alcohol, wherein said microbial organism comprises a crotyl alcohol pathway comprising at least two exogenous nucleic acids encoding crotyl alcohol pathway enzymes expressed in a sufficient amount to produce crotyl alcohol, wherein said crotyl alcohol pathway comprises converting crotonyl-CoA to crotyl alcohol using at least one exogenous nucleic acid of said two exogenous nucleic acids, wherein said crotyl alcohol pathway enzymes are selected from the group consisting of:
   (i) a crotonyl-CoA reductase (aldehyde forming), and a crotonaldehyde reductase (alcohol forming);
   (ii) a crotonyl-CoA reductase (alcohol forming); and
   (iii) a crotonyl-CoA hydrolase, synthetase, or transferase, a crotonate reductase, and a crotonaldehyde reductase (alcohol forming), and
   wherein said crotyl alcohol pathway further comprises at least one exogenous nucleic acid of said two exogenous nucleic acids that encodes a crotyl alcohol pathway enzyme for converting:
   (i) acetyl-CoA to crotonyl-CoA using an acetyl-CoA:acetyl-CoA acyltransferase, an acetoacetyl-CoA reductase and a 3-hydroxybutyryl-CoA dehydratase;
   (ii) glutaconyl-CoA to crotonyl-CoA using a glutaconyl-CoA decarboxylase;
   (iii) glutaryl-CoA to crotonyl-CoA using a glutaryl-CoA dehydrogenase;
   (iv) 3-aminobutyryl-CoA to crotonyl-CoA using an 3-aminobutyryl-CoA deaminase; or
   (v) 4-hydroxybutyryl-CoA to crotonyl-CoA using a 4-hydroxybutyryl-CoA dehydratase; and
   (b) converting the crotyl alcohol produced by culturing said non-naturally occurring microbial organism in step (a) to butadiene using a chemical procedure.

2. The process of claim 1, wherein step (b) is performed by chemical dehydration in the presence of a catalyst.

3. The process of claim 1, wherein said microbial organism comprises two, three, four, five, or six exogenous nucleic acids each encoding a crotyl alcohol pathway enzyme.

4. The process of claim 1, wherein said crotyl alcohol pathway comprises an acetyl-CoA:acetyl-CoA acyltransferase, an acetoacetyl-CoA reductase, a 3-hydroxybutyryl-CoA dehydratase, a crotonyl-CoA reductase (aldehyde forming), and a crotonaldehyde reductase (alcohol forming).

5. The process of claim 1, wherein said at least one exogenous nucleic acid is a heterologous nucleic acid.

6. The process of claim 1, wherein said non-naturally occurring microbial organism is in a substantially anaerobic culture medium.

7. The process of claim 1, wherein said crotyl alcohol pathway comprises an acetyl-CoA:acetyl-CoA acyltransferase, an acetoacetyl-CoA reductase, a 3-hydroxybutyryl-CoA dehydratase, and a crotonyl-CoA reductase (alcohol forming).

8. The process of claim 1, wherein said crotyl alcohol pathway comprises an acetyl-CoA:acetyl-CoA acyltransferase, an acetoacetyl-CoA reductase, a 3-hydroxybutyryl-CoA dehydratase, a crotonaldehyde reductase (alcohol forming), a crotonyl-CoA hydrolase, synthetase or transferase, and a crotonate reductase.

9. The process of claim 1, wherein said crotyl alcohol pathway comprises a glutaconyl-CoA decarboxylase, a crotonyl-CoA reductase (aldehyde forming), and a crotonaldehyde reductase (alcohol forming).

10. The process of claim 1, wherein said crotyl alcohol pathway comprises a glutaconyl-CoA decarboxylase and a crotonyl-CoA reductase (alcohol forming).

11. The process of claim 1, wherein said crotyl alcohol pathway comprises a glutaconyl-CoA decarboxylase, a crotonaldehyde reductase (alcohol forming), a crotonyl-CoA hydrolase, synthetase, or transferase, and a crotonate reductase.

12. The process of claim 1, wherein said crotyl alcohol pathway comprises a glutaryl-CoA dehydrogenase, a crotonyl-CoA reductase (aldehyde forming), and a crotonaldehyde reductase (alcohol forming).

13. The process of claim 1, wherein said crotyl alcohol pathway comprises a glutaryl-CoA dehydrogenase and a crotonyl-CoA reductase (alcohol forming).

14. The process of claim 1, wherein said crotyl alcohol pathway comprises a glutaryl-CoA dehydrogenase, a crotonaldehyde reductase (alcohol forming), a crotonyl-CoA hydrolase, synthetase, or transferase, and a crotonate reductase.

15. The process of claim 1, wherein said crotyl alcohol pathway comprises a 3-aminobutyryl-CoA deaminase, a crotonyl-CoA reductase (aldehyde forming), and a crotonaldehyde reductase (alcohol forming).

16. The process of claim 1, wherein said crotyl alcohol pathway comprises a 3-aminobutyryl-CoA deaminase and a crotonyl-CoA reductase (alcohol forming).

17. The process of claim 1, wherein said crotyl alcohol pathway comprises a 3-aminobutyryl-CoA deaminase, a crotonaldehyde reductase (alcohol forming), a crotonyl-CoA hydrolase, synthetase or transferase and a crotonate reductase.

18. The process of claim 1, wherein said crotyl alcohol pathway comprises a 4-hydroxybutyryl-CoA dehydratase, a crotonyl-CoA reductase (aldehyde forming), and a crotonaldehyde reductase (alcohol forming).

19. The process of claim 1, wherein said crotyl alcohol pathway comprises a 4-hydroxybutyryl-CoA dehydratase and a crotonyl-CoA reductase (alcohol forming).

20. The process of claim 1, wherein said crotyl alcohol pathway comprises a 4-hydroxybutyryl-CoA dehydratase, a crotonaldehyde reductase (alcohol forming), a crotonyl-CoA hydrolase, synthetase or transferase, and a crotonate reductase.

* * * * *